US011352406B2

(12) United States Patent
Madsen et al.

(10) Patent No.: US 11,352,406 B2
(45) Date of Patent: Jun. 7, 2022

(54) INSULIN DERIVATIVES AND THE MEDICAL USES HEREOF

(71) Applicant: Novo Nordisk A/S, Bagsvaerd (DK)

(72) Inventors: Peter Madsen, Bagsvaerd (DK); Anthony Murray, Charlottenlund (DK); Martin Muenzel, Broenshoej (DK); Claudia Ulrich Hjoerringgaard, Glostrup (DK); Susanne Hostrup, Vaerloese (DK); Tine Glendorf, Hilleroed (DK); Mathias Norrman, Staffanstorp (SE); Christian Fledelius, Copenhagen (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 15/754,395

(22) PCT Filed: Aug. 24, 2016

(86) PCT No.: PCT/EP2016/069972
§ 371 (c)(1),
(2) Date: Feb. 22, 2018

(87) PCT Pub. No.: WO2017/032798
PCT Pub. Date: Mar. 2, 2017

(65) Prior Publication Data
US 2018/0305431 A1    Oct. 25, 2018

(30) Foreign Application Priority Data

Aug. 25, 2015 (EP) ..................................... 15182282

(51) Int. Cl.
*C07K 14/62* (2006.01)
*A61K 47/22* (2006.01)
*A61K 38/00* (2006.01)

(52) U.S. Cl.
CPC .............. *C07K 14/62* (2013.01); *A61K 47/22* (2013.01); *A61K 38/00* (2013.01)

(58) Field of Classification Search
None
See application file for complete search history.

(56) References Cited

U.S. PATENT DOCUMENTS

| 5,382,574 | A | * | 1/1995 | Jorgensen | A61K 38/28 |
| | | | | | 514/6.4 |
| 5,618,913 | A | | 4/1997 | Brange et al. | |
| 5,750,497 | A | | 5/1998 | Havelund et al. | |
| 5,922,678 | A | | 7/1999 | Stephens | |
| 6,960,561 | B2 | | 11/2005 | Boderke | |
| 9,068,013 | B2 | | 6/2015 | Lancaster et al. | |
| 2001/0036916 | A1 | | 11/2001 | Brader | |
| 2005/0085621 | A1 | | 4/2005 | Berchtold | |

| 2007/0129284 | A1 | 6/2007 | Kjeldsen et al. |
| 2014/0315797 | A1 | 10/2014 | Madsen et al. |
| 2021/0179685 | A1 | 6/2021 | Hubalek et al. |

FOREIGN PATENT DOCUMENTS

| CN | 105440125 | | 3/2016 |
| EP | 2784085 | | 10/2014 |
| JP | 2001521006 | A | 11/2001 |
| JP | 2008502313 | A | 1/2008 |
| JP | 2010535841 | A | 11/2010 |
| JP | 2013541500 | A | 11/2013 |
| WO | 98/42749 | A1 | 10/1998 |
| WO | 06097521 | A1 | 9/2006 |
| WO | 2007096431 | A1 | 8/2007 |
| WO | 2007104738 | A2 | 9/2007 |
| WO | 2009011005 | A1 | 1/2009 |
| WO | 09/022006 | A1 | 2/2009 |
| WO | 2009/022005 | A1 | 2/2009 |
| WO | 2009021955 | | 2/2009 |
| WO | 2009022013 | A1 | 2/2009 |
| WO | WO2009-022005 | * | 2/2009 |
| WO | 2009/112583 | A2 | 9/2009 |
| WO | WO2009-115469 | * | 9/2009 |
| WO | 2009/121884 | A1 | 10/2009 |
| WO | 2011/000823 | A1 | 1/2011 |
| WO | 2011051486 | A2 | 5/2011 |
| WO | 2011161124 | A1 | 12/2011 |
| WO | 2012/171994 | A1 | 12/2012 |
| WO | 2013/063572 | A1 | 5/2013 |
| WO | 14158900 | A1 | 10/2014 |
| WO | 15051052 | A2 | 4/2015 |

(Continued)

OTHER PUBLICATIONS

Encyclopedia Britannica (https://www.britannica.com/science/metabolic-disease; accessed Aug. 30, 2019.*
The Merck Manual (https://www.merckmanuals.com/professional/pediatrics/inherited-disorders-of-metabolism/phenylketonuria-pku copyright 2018).*
The Merck Manual (https://www.merckmanuals.com/professional/pediatrics/inherited-disorders-of-metabolism/urea-cycle-disorders?query=urea%20defects copyright 2018).*
Brange et al. "Chemical stability of insulin. 4. Mechanisms and kinetics of chemical transformations in pharmaceutical formulation." Acta Pharmaceutica Nordica 1992 vol. 4(4) pp. 209-222.
Brange, J et al. "Chemical Stability of Insulin 3. Influence of Excipients, formulation and pH." Acta Pharma Nordica 1992 vol. 4(3) pp. 149-158.
Hahr, A J et al. "Optimizing insulin therapy in patients with type 1 and type 2 diabetes mellitus: optimal dosing and timing in the outpatient setting." Disease-a-month 2010 vol. 56(3) pp. 148-162.

(Continued)

*Primary Examiner* — Julie Ha
*Assistant Examiner* — Tara L Martinez
(74) *Attorney, Agent, or Firm* — Rosemarie R. Wilk-Orescan

(57) ABSTRACT

The present invention is in the therapeutic fields of drugs for medical conditions relating to diabetes. More specifically the invention relates to novel acylated derivatives of human insulin analogues. The invention also provides pharmaceutical compositions comprising such insulin derivatives, and relates to the use of such derivatives for the treatment or prevention of medical conditions relating to diabetes.

8 Claims, 13 Drawing Sheets

Specification includes a Sequence Listing.

(56) References Cited

FOREIGN PATENT DOCUMENTS

| WO | 2015/128403 A2 | 9/2015 |
|---|---|---|
| WO | 2017032795 A1 | 3/2017 |
| WO | 2017032798 A1 | 3/2017 |
| WO | 19125879 | 6/2019 |

OTHER PUBLICATIONS

Huus K et al. "Chemical and thermal stability of insulin: effects of zinc and ligand binding to the insulin zinc-hexamer" Pharmaceutical Research 2006 vol. 23(11) pp. 2611-2620.
Epstein, Charles J., "Non-randomness of Amino-acid changes in teh evolution of homologous proteins." Nature, 1967, vol. 215, No. 5099, Tables 1-2, pp. 355-359.
Forbes et al., "Mechanisms of diabetic complications." Physiological reviews, 2013, vol. 93, No. 1, pp. 137-188.
Haberle et al.,"Suggested guidelines for the diagnosis and management of urea cycle disorders." Orghanet J. Rare Dis. 2012, vol. 7, No. 32, pp. 1-30.
Yao, Z-P., et al. "Structure of an insulin dimer in an orthorhombic crystal: the structure analysis of a human insulin mutant (B9 Ser-Glu)." Acta Crystallographica Section D: Biological Crystallography, Sep. 1999, vol. 55, No. 9, pp. 1524-1532.
Zoete et al.. "A comparison of the dynamic behavior of monomeric and dimeric insulin shows structural rearrangements in the active monomer." Journal of molecular biology, Sep. 2004, vol. 342, No. 3, pp. 913-929.
Brange et al. "Monomeric insulins and their experimental and clinical implications." Diabetes Care, Sep. 1990, vol. 13, No. 9, pp. 923-954.
DiMarchi et al. "Three chain insulin analogs demonstrate the importance of insulin secondary structure to bioactivity." Journal of Peptide Science, Mar. 2015, vol. 21, No. 3, pp. 223-230.
Hjorth et al., "Purification and identification of high molecular weight products formed during storage of neutral formulation of human insulin," Pharm. Res., 2015, vol. 32, No. 6, pp. 2072-2085.
Hjorth et al., "Structure, Aggregation, and Activity of a Covalent Insulin Dimer Formed During Storage of Neutral Formulation of Human Insulin," J. Pharm. Sci., 2016, vol. 105, No. 4, pp. 1376-1386.
Min et al., "Insulin related compounds and identification," J. Chromatogr. B, 2012, vol. 908, pp. 105-112.

\* cited by examiner

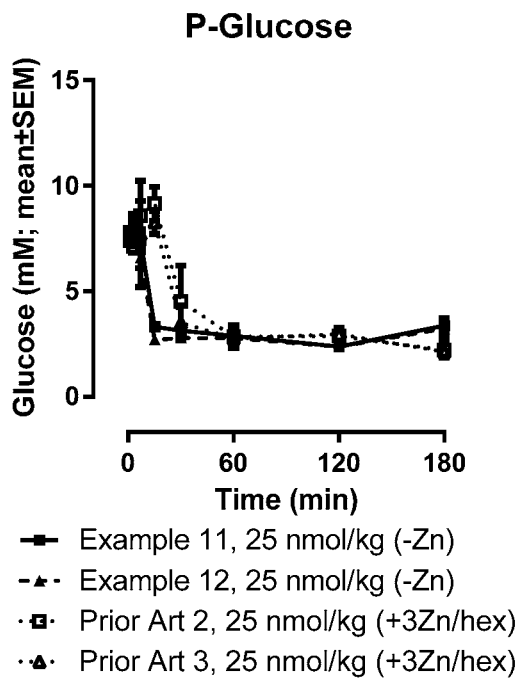
Fig. 2D1
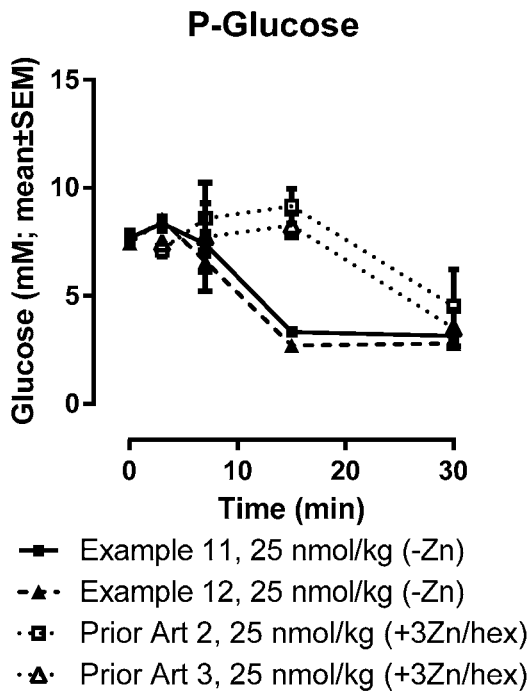
Fig. 2D2

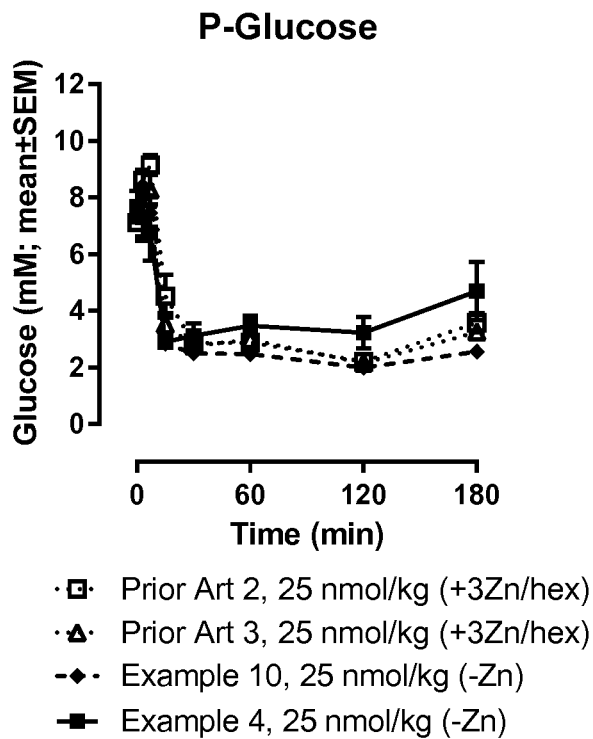
Fig. 2E1
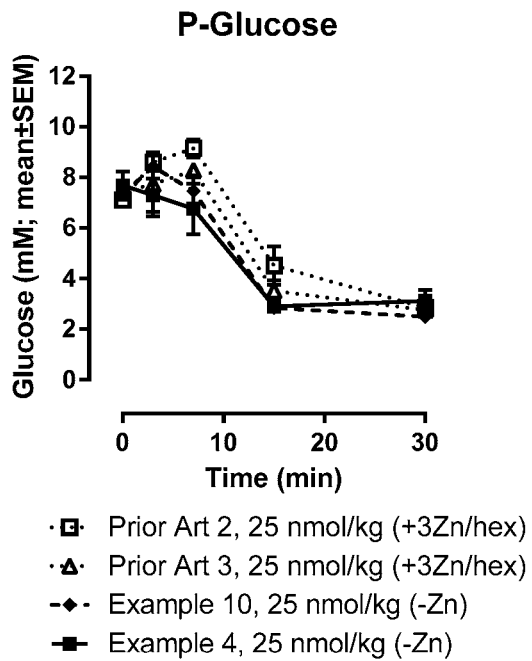
Fig. 2E2

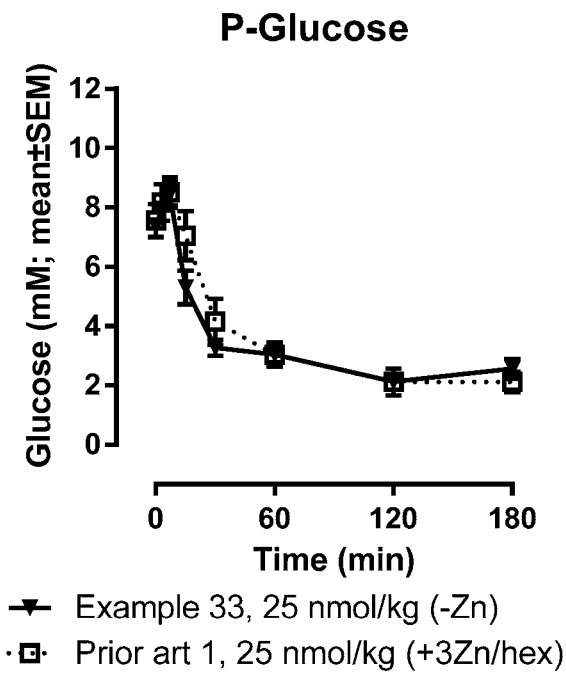
Fig. 2F1
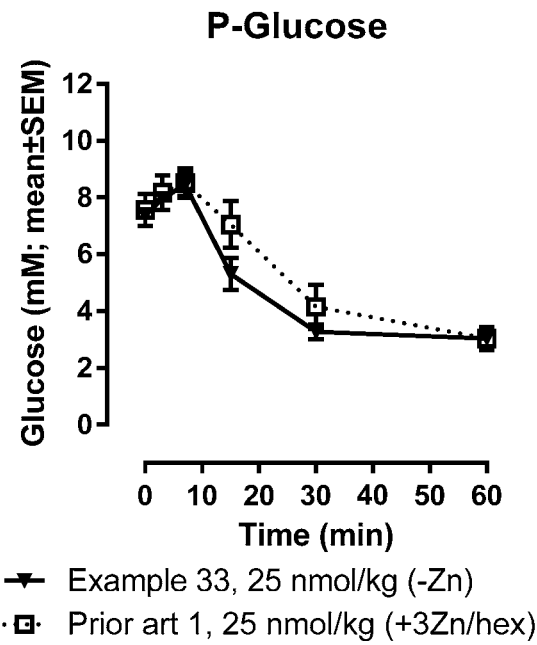
Fig. 2F2

SEQUENCE LISTING

<160> NUMBER OF SEQ ID NOS: 22

<210> SEQ ID NO 1
<211> LENGTH: 22
<212> TYPE: PRT
<213> ORGANISM: Artificial Sequence
<220> FEATURE:
<223> OTHER INFORMATION: A-chain of analogue [A8R, A22K] of human
      insulin
<220> FEATURE:
<221> NAME/KEY: MOD_RES
<222> LOCATION: (22)..(22)
<223> OTHER INFORMATION: ACETYLATION

<400> SEQUENCE: 1

Gly Ile Val Glu Gln Cys Cys Arg Ser Ile Cys Ser Leu Tyr Gln Leu
1               5                   10                  15

Glu Asn Tyr Cys Asn Lys
            20

<210> SEQ ID NO 2
<211> LENGTH: 22
<212> TYPE: PRT
<213> ORGANISM: Artificial Sequence
<220> FEATURE:
<223> OTHER INFORMATION: A-chain of analogue [A14E, A22K] of human
      insulin
<220> FEATURE:
<221> NAME/KEY: MOD_RES
<222> LOCATION: (22)..(22)
<223> OTHER INFORMATION: ACETYLATION

<400> SEQUENCE: 2

Gly Ile Val Glu Gln Cys Cys Thr Ser Ile Cys Ser Leu Glu Gln Leu
1               5                   10                  15

Glu Asn Tyr Cys Asn Lys
            20

<210> SEQ ID NO 3
<211> LENGTH: 22
<212> TYPE: PRT
<213> ORGANISM: Artificial Sequence
<220> FEATURE:
<223> OTHER INFORMATION: A-chain of analogue [A22K] of human insulin

```
<220> FEATURE:
<221> NAME/KEY: MOD_RES
<222> LOCATION: (22)..(22)
<223> OTHER INFORMATION: ACETYLATION

<400> SEQUENCE: 3

Gly Ile Val Glu Gln Cys Cys Thr Ser Ile Cys Ser Leu Tyr Gln Leu
1               5                   10                  15

Glu Asn Tyr Cys Asn Lys
            20

<210> SEQ ID NO 4
<211> LENGTH: 29
<212> TYPE: PRT
<213> ORGANISM: Artificial Sequence
<220> FEATURE:
<223> OTHER INFORMATION: B-chain of analogue [B3E, B26E, B27E, B28E,
      B29R, desB30] of human insulin

<400> SEQUENCE: 4

Phe Val Glu Gln His Leu Cys Gly Asp His Leu Val Glu Ala Leu Tyr
1               5                   10                  15

Leu Val Cys Gly Glu Arg Gly Phe Phe Glu Glu Glu Arg
            20                  25

<210> SEQ ID NO 5
<211> LENGTH: 28
<212> TYPE: PRT
<213> ORGANISM: Artificial Sequence
<220> FEATURE:
<223> OTHER INFORMATION: B-chain of analogue [B3E, B26E, B27E, B28R,
      desB29, desB30] of human insulin

<400> SEQUENCE: 5

Phe Val Glu Gln His Leu Cys Gly Asp His Leu Val Glu Ala Leu Tyr
1               5                   10                  15

Leu Val Cys Gly Glu Arg Gly Phe Phe Glu Glu Arg
            20                  25

<210> SEQ ID NO 6
<211> LENGTH: 30
<212> TYPE: PRT
<213> ORGANISM: Artificial Sequence
<220> FEATURE:
<223> OTHER INFORMATION: B-chain of analogue [B3E, B26E, B27E, B29P,
      B30R] of human insulin

<400> SEQUENCE: 6

Phe Val Glu Gln His Leu Cys Gly Asp His Leu Val Glu Ala Leu Tyr
1               5                   10                  15

Leu Val Cys Gly Glu Arg Gly Phe Phe Glu Glu Pro Pro Arg
            20                  25                  30

<210> SEQ ID NO 7
<211> LENGTH: 28
<212> TYPE: PRT
<213> ORGANISM: Artificial Sequence
<220> FEATURE:
<223> OTHER INFORMATION: B-chain of analogue [B3E, B26E, B27P, B28R,
      desB29, desB30] of human insulin

<400> SEQUENCE: 7

Phe Val Glu Gln His Leu Cys Gly Asp His Leu Val Glu Ala Leu Tyr
1               5                   10                  15

Leu Val Cys Gly Glu Arg Gly Phe Phe Glu Pro Arg
```

20                  25

<210> SEQ ID NO 8
<211> LENGTH: 29
<212> TYPE: PRT
<213> ORGANISM: Artificial Sequence
<220> FEATURE:
<223> OTHER INFORMATION: B-chain of analogue [B3E, B26E, B28D, B29R,
      desB30] of human insulin

<400> SEQUENCE: 8

Phe Val Glu Gln His Leu Cys Gly Asp His Leu Val Glu Ala Leu Tyr
1               5                   10                  15

Leu Val Cys Gly Glu Arg Gly Phe Phe Glu Thr Asp Arg
                    20                  25

<210> SEQ ID NO 9
<211> LENGTH: 30
<212> TYPE: PRT
<213> ORGANISM: Artificial Sequence
<220> FEATURE:
<223> OTHER INFORMATION: B-chain of analogue [B3E, B26E, B28E, B29P,
      B30R] of human insulin

<400> SEQUENCE: 9

Phe Val Glu Gln His Leu Cys Gly Asp His Leu Val Glu Ala Leu Tyr
1               5                   10                  15

Leu Val Cys Gly Glu Arg Gly Phe Phe Glu Thr Glu Pro Arg
                    20                  25                  30

<210> SEQ ID NO 10
<211> LENGTH: 29
<212> TYPE: PRT
<213> ORGANISM: Artificial Sequence
<220> FEATURE:
<223> OTHER INFORMATION: B-chain of analogue [B3E, B26E, B28E, B29R,
      desB30] of human insulin

<400> SEQUENCE: 10

Phe Val Glu Gln His Leu Cys Gly Asp His Leu Val Glu Ala Leu Tyr
1               5                   10                  15

Leu Val Cys Gly Glu Arg Gly Phe Phe Glu Thr Glu Arg
                    20                  25

<210> SEQ ID NO 11
<211> LENGTH: 29
<212> TYPE: PRT
<213> ORGANISM: Artificial Sequence
<220> FEATURE:
<223> OTHER INFORMATION: B-chain of analogue [B3E, B26E, B29R, desB30]
      of human insulin

<400> SEQUENCE: 11

Phe Val Glu Gln His Leu Cys Gly Asp His Leu Val Glu Ala Leu Tyr
1               5                   10                  15

Leu Val Cys Gly Glu Arg Gly Phe Phe Glu Thr Pro Arg
                    20                  25

<210> SEQ ID NO 12
<211> LENGTH: 29
<212> TYPE: PRT
<213> ORGANISM: Artificial Sequence
<220> FEATURE:
<223> OTHER INFORMATION: B-chain of analogue [B3Q, B26E, B29R, desB30]
      of human insulin -continued

```
<400> SEQUENCE: 12

Phe Val Gln Gln His Leu Cys Gly Asp His Leu Val Glu Ala Leu Tyr
1               5                   10                  15

Leu Val Cys Gly Glu Arg Gly Phe Phe Glu Thr Pro Arg
            20                  25

<210> SEQ ID NO 13
<211> LENGTH: 29
<212> TYPE: PRT
<213> ORGANISM: Artificial Sequence
<220> FEATURE:
<223> OTHER INFORMATION: B-chain of analogue [B3Q, B26E, B28E, B29R,
      desB30] of human insulin

<400> SEQUENCE: 13

Phe Val Gln Gln His Leu Cys Gly Asp His Leu Val Glu Ala Leu Tyr
1               5                   10                  15

Leu Val Cys Gly Glu Arg Gly Phe Phe Glu Thr Glu Arg
            20                  25

<210> SEQ ID NO 14
<211> LENGTH: 28
<212> TYPE: PRT
<213> ORGANISM: Artificial Sequence
<220> FEATURE:
<223> OTHER INFORMATION: B-chain of analogue [B3E, B27E, B28R, desB29,
      desB30] of human insulin

<400> SEQUENCE: 14

Phe Val Glu Gln His Leu Cys Gly Asp His Leu Val Glu Ala Leu Tyr
1               5                   10                  15

Leu Val Cys Gly Glu Arg Gly Phe Phe Tyr Glu Arg
            20                  25

<210> SEQ ID NO 15
<211> LENGTH: 30
<212> TYPE: PRT
<213> ORGANISM: Artificial Sequence
<220> FEATURE:
<223> OTHER INFORMATION: B-chain of analogue [B3E, B27E, B28E, B29P,
      B30R] of human insulin

<400> SEQUENCE: 15

Phe Val Glu Gln His Leu Cys Gly Asp His Leu Val Glu Ala Leu Tyr
1               5                   10                  15

Leu Val Cys Gly Glu Arg Gly Phe Phe Tyr Glu Glu Pro Arg
            20                  25                  30

<210> SEQ ID NO 16
<211> LENGTH: 29
<212> TYPE: PRT
<213> ORGANISM: Artificial Sequence
<220> FEATURE:
<223> OTHER INFORMATION: B-chain of analogue [B3E, B27E, B28E, B29R,
      desB30] of human insulin

<400> SEQUENCE: 16

Phe Val Glu Gln His Leu Cys Gly Asp His Leu Val Glu Ala Leu Tyr
1               5                   10                  15

Leu Val Cys Gly Glu Arg Gly Phe Phe Tyr Glu Glu Arg
            20                  25

<210> SEQ ID NO 17
<211> LENGTH: 29
```

```
<212> TYPE: PRT
<213> ORGANISM: Artificial Sequence
<220> FEATURE:
<223> OTHER INFORMATION: B-chain of analogue [B3E, B27P, B28E, B29R,
      desB30] of human insulin

<400> SEQUENCE: 17

Phe Val Glu Gln His Leu Cys Gly Asp His Leu Val Glu Ala Leu Tyr
1               5                   10                  15

Leu Val Cys Gly Glu Arg Gly Phe Phe Tyr Pro Glu Arg
            20                  25

<210> SEQ ID NO 18
<211> LENGTH: 29
<212> TYPE: PRT
<213> ORGANISM: Artificial Sequence
<220> FEATURE:
<223> OTHER INFORMATION: B-chain of analogue [B3E, B27E, B29R, desB30]
      of human insulin

<400> SEQUENCE: 18

Phe Val Glu Gln His Leu Cys Gly Asp His Leu Val Glu Ala Leu Tyr
1               5                   10                  15

Leu Val Cys Gly Glu Arg Gly Phe Phe Tyr Glu Pro Arg
            20                  25

<210> SEQ ID NO 19
<211> LENGTH: 29
<212> TYPE: PRT
<213> ORGANISM: Artificial Sequence
<220> FEATURE:
<223> OTHER INFORMATION: B-chain of analogue [B3Q, B27E, B28E, B29R,
      desB30] of human insulin

<400> SEQUENCE: 19

Phe Val Gln Gln His Leu Cys Gly Asp His Leu Val Glu Ala Leu Tyr
1               5                   10                  15

Leu Val Cys Gly Glu Arg Gly Phe Phe Tyr Glu Glu Arg
            20                  25

<210> SEQ ID NO 20
<211> LENGTH: 29
<212> TYPE: PRT
<213> ORGANISM: Artificial Sequence
<220> FEATURE:
<223> OTHER INFORMATION: B-chain of analogue [B3E, B28D, B29R, desB30]
      of human insulin

<400> SEQUENCE: 20

Phe Val Glu Gln His Leu Cys Gly Asp His Leu Val Glu Ala Leu Tyr
1               5                   10                  15

Leu Val Cys Gly Glu Arg Gly Phe Phe Tyr Thr Asp Arg
            20                  25

<210> SEQ ID NO 21
<211> LENGTH: 30
<212> TYPE: PRT
<213> ORGANISM: Artificial Sequence
<220> FEATURE:
<223> OTHER INFORMATION: B-chain of analogue [B3E, B28E, B29P, B30R] of
      human insulin

<400> SEQUENCE: 21

Phe Val Glu Gln His Leu Cys Gly Asp His Leu Val Glu Ala Leu Tyr
1               5                   10                  15
```

```
Leu Val Cys Gly Glu Arg Gly Phe Phe Tyr Thr Glu Pro Arg
            20                  25                  30

<210> SEQ ID NO 22
<211> LENGTH: 29
<212> TYPE: PRT
<213> ORGANISM: Artificial Sequence
<220> FEATURE:
<223> OTHER INFORMATION: B-chain of analogue [B3Q, B28D, B29R, desB30]
      of human insulin

<400> SEQUENCE: 22

Phe Val Gln Gln His Leu Cys Gly Asp His Leu Val Glu Ala Leu Tyr
1               5                   10                  15

Leu Val Cys Gly Glu Arg Gly Phe Phe Tyr Thr Asp Arg
            20                  25
```

INSULIN DERIVATIVES AND THE MEDICAL USES HEREOF

CROSS-REFERENCE TO RELATED APPLICATIONS

This application is a 35 U.S.C. § 371 National Stage application of International Application PCT/EP2016/069972 (WO 2017/032798), filed Aug. 24, 2016, which claims priority to European Patent Application 15182282.2, filed Aug. 25, 2015; the contents of which are incorporated herein by reference.

In accordance with 37 C.F.R. § 1.52(e)(5), Applicants enclose herewith the Sequence Listing for the above-captioned application entitled "150027US01_SeqList.txt", created on Jan. 24, 2018. The Sequence Listing is made up of 10 kilobytes, and the information contained in the attached "SEQUENCE LISTING" is identical to the information in the specification as originally filed. No new matter is added.

TECHNICAL FIELD

The present invention is in the therapeutic fields of drugs for medical conditions relating to diabetes. More specifically the invention relates to novel acylated derivatives of human insulin analogues. The invention also provides pharmaceutical compositions comprising such derivatized insulin analogues, and relates to the use of such derivatives for the treatment or prevention of medical conditions relating to diabetes.

BACKGROUND OF THE INVENTION

Insulin therapy for the treatment of diabetes has been used for decades. Insulin therapy usually involves administering several injections of insulin each day. Such therapy usually involves administration of a long-acting basal injection once or twice daily, and an injection of a fast-acting insulin at mealtime (i.e. prandial use). One of the key improvements in insulin therapy was the introduction of rapid-acting insulin analogues. However, even with the rapid-acting insulin analogues, peak insulin levels typically do not occur until 50 to 70 minutes following the injection.

Therefore insulin injections do not replicate the natural time-action profile of insulin. In particular, the natural spike of the first-phase insulin release in a person without diabetes results in blood insulin levels rising within several minutes of the entry into the blood of glucose from a meal. By contrast, injected insulin enters the blood only slowly, with peak insulin levels occurring within 80 to 100 minutes following the injection of regular human insulin.

Because the rapid-acting insulin analogues do not adequately mimic the first-phase insulin release, diabetics using insulin therapy continue to have inadequate levels of insulin present at the initiation of a meal, and too much insulin present between meals. This lag in insulin delivery can result in hyperglycemia early after meal onset.

Insulin possesses self-association properties, and its concentration represents a major factor of self-association. At high concentrations, especially in pharmaceutical formulations, insulin will self-associate into dimer, hexamer, dodecamer, and crystal. However, the physiologically active form of insulin is the monomer, which binds with the insulin receptor and triggers a biological response.

The rapidity of insulin action is dependent on how quickly the insulin is absorbed from the subcutaneous tissue. When regular human insulin is injected subcutaneously, the formulation is primarily composed of hexamers containing two zinc ions. Due to its size, the hexameric insulin has a lower rate of diffusion and consequently, the absorption rate is slower than for smaller species.

Located within the hexamer are two zinc atoms that stabilize the molecule towards chemical and physical degradation. Post injection, a concentration driven dynamic equilibrium occurs in the subcutaneous tissue, causing the hexamers to dissociate into dimers, and then to monomers. Historically, these regular human insulin formulations require approximately 120 minutes to reach maximum plasma concentration levels. Zinc-insulin preparations, that are more quickly absorbed than regular human insulin, have been commercialised, e.g. insulin aspart and insulin lispro.

Zinc-free insulin formulations would enable faster subcutaneous absorption, but for insulins in general, the chemical and physical stability of zinc-free formulations is a challenge.

Various insulin derivatives have been suggested for different uses:

WO 1998 042749 describes zinc-free insulin crystals for pulmonary administration.

U.S. Pat. No. 6,960,561 describes zinc-free and low-zinc insulin preparations having improved stability.

WO 2007/096431 describes certain human insulin derivatives, including analogues i.a. at position A22 holding an acylated lysine residue, in position B29 holding an arginine residue, and being desB30, which derivatives are soluble at physiological pH values and have a prolonged profile of action, and intended for use as long acting insulins.

WO 2009/022013 describes certain acylated insulin analogues, including analogues i.a. at position A22 holding an acylated lysine residue, in position B29 holding an arginine residue, and being desB30, possessing higher insulin receptor binding affinities, and intended for use as long acting insulins.

WO 2009/112583 describes certain insulin analogues, including analogues at position A22 holding a lysine residue, in position B29 holding an arginine residue, and being desB30, exhibiting improved protease stability.

WO 2011/161124 describes certain acylated insulin analogues containing additional disulfide bonds for improved stability, including analogues i.a. at position A22 holding a lysine residue, in position B29 holding an arginine residue, and being desB30.

WO 2012/171994 describes certain insulin derivative comprising two or more substitutions, including analogues i.a. at position A22 holding an acylated lysine residue, in position B29 holding an arginine residue, and being desB30, for prolonged in vivo activity.

WO 2013 063572 describes ultra-concentrated rapid-acting insulin analogue formulations optionally devoid of zinc.

Moreover, acylation of peptides and proteins with albumin binding moieties have been used to prolong the duration of action of the peptides and proteins.

However, the insulin derivatives according to the present invention have not been reported, and their use as fast acting insulin derivatives for prandial use has never been suggested.

OBJECTS OF THE INVENTION

It is an object of the invention to provide insulin analogues that have a prandial profile following subcutaneous administration.

Another object of the invention is to provide insulin analogues that are chemically stable in formulation.

A third object of the invention is to provide insulin analogues that are chemically stable in formulation without added zinc.

A fourth object of the invention is to provide insulin analogues that are physically stable in formulation.

A fifth object of the invention is to provide insulin analogues that are physically stable in formulation without added zinc.

A sixth object of the invention is to provide insulin analogues that are chemically and physically stable in formulation.

A seventh object of the invention is to provide insulin analogues that are chemically and physically stable in formulation without added zinc.

An eight object of the invention is to provide insulin analogues that are hepatopreferential relative to currently marketed prandial insulins following subcutaneous administration.

A ninth object of the invention is to provide insulin analogues that are hepatoselective relative to currently marketed prandial insulins following subcutaneous administration.

A tenth object of the invention is to provide insulin analogues that are less prone to induce hypoglycaemia relative to currently marketed prandial insulins following prandial subcutaneous administration.

An eleventh object of the invention is to provide insulin analogues that are less prone to induce weight gain relative to currently marketed prandial insulins following prandial subcutaneous administration.

A twelfth object of the invention is to provide insulin analogues that are less prone to induce hypoglycaemia and weight gain relative to currently marketed prandial insulins following prandial subcutaneous administration.

A thirteenth object of the invention is to provide insulin analogues that have less action in muscle and/or fat tissue relative to currently marketed prandial insulins following subcutaneous administration.

Further objects of this invention are drawn to combinations of one or more of the objects mentioned above, and in particular the provision of insulin analogues that show a prandial profile following subcutaneous administration, while being chemically stable in formulations, and in particular in formulations without added zinc.

SUMMARY OF THE INVENTION

We have discovered that the A22K acylated insulin derivatives of the present invention have significantly improved properties relative to similar insulin derivatives of the prior art. We have in particular discovered that the insulin derivatives of the invention, in formulations containing no added zinc ions, and when compared to similar derivatives of the prior art, are associated with a smaller size of the molecular aggregates. Smaller species are known to diffuse more rapidly than larger species, and faster absorption is consequently to be expected. The size of these molecular aggregates can e.g. be measured as described herein by Small Angle X-ray Scattering (SAXS) as described in the examples section.

We have also discovered that the insulin derivatives of the invention, relative to similar derivatives of the prior art, in formulations containing no added zinc ions, are absorbed more rapidly after subcutaneous administration to pigs and/or rats, thereby demonstrating a potential clinical utility as insulins for prandial use. We have discovered that the insulin derivatives of the invention, relative to similar derivatives of the prior art, in formulations containing no added zinc ions are associated with less "tailing" following subcutaneous administration to pigs. By less tailing is meant that the subcutaneous depot of injected insulin is absorbed more rapidly than for similar analogues of the prior art, so that the mean residence time (MRT) following subcutaneous administration is shorter for the insulin derivatives of the invention when compared to similar acylated derivatives of the prior art.

Zinc-free formulations enable faster subcutaneous absorption, but for insulins in general, chemical and physical stability of zinc-free formulations is a challenge, and has until now only been shown to be possible with insulin glulisine (Apidra®; B3K, B29E human insulin), and only in the presence of surfactants when dispensed in vials.

We have now discovered that the A22K acylated insulin derivatives of the invention, with substitutions in position B3, very unexpectedly and unprecedented are both chemically and physically stable in formulations with no added zinc-ions and no added surfactants.

The rate of absorption of insulin following subcutaneous administration is to a large extent correlated by the rate of diffusion. Thus, smaller species have faster diffusion rates and concomitant faster rates of absorption than larger species.

Insulin preparations containing zinc are absorbed more slowly than zinc-free formulations since the zinc-hexamers of the formulation needs to dissociate to dimers and/or monomers before absorption can take place.

Chemical and physical stability of insulin formulations require presence of zinc, and absence of zinc is required for fast absorption. A solution to this problem is provided in the present invention.

Since insulin needs to be stable in formulation in order to be clinically useful, the property of the insulins of the invention being stable in zinc-free formulation results in pharmacokinetic and pharmacodynamic properties superior to those of the insulins of the prior art. This is because that the insulins of the prior art need to be formulated with zinc ions in order to be stable in formulation. The proper comparison regarding pharmacokinetic and pharmacodynamic properties is thus to compare stable formulations and, consequently, to compare stable zinc-free formulations of insulins of the invention with zinc-containing formulations of insulins of the prior art.

An advantage by using acylated insulin derivatives as prandial insulin therapy is to achieve higher plasma insulin concentrations than those achieved with treatment with un-acylated prandial insulins, like insulin aspart, insulin lispro or insulin glulisine.

The A22K acylated insulin derivatives according to the invention have a prandial-like time-action profile following subcutaneous administration.

The A22K acylated insulin derivatives with tetradecanedioic acid, pentadecanedioic acid, or hexadecanedioic acid based albumin binders according to the invention have shown to confer very high insulin receptor binding affinities, affinities that are reduced in the presence of 1.5% human serum albumin (HSA).

The A22K acylated insulin derivatives according to the invention do not have reduced solubility at physiological salt concentrations.

Accordingly, in its first aspect, the invention provides an acylated analogue of human insulin, which analogue is [A22Lys, B3aar$^1$] relative to human insulin; wherein aar¹ represents Glu (E), Gln (Q), Asp (D), Ser (S) or Thr (T); and one, two or three of the amino acid residues located in positions B26, B27 and/or B28 are substituted as follows:

the amino acid residue located in position B26 is substituted for Glu (E) or Asp (D); and/or the amino acid residue located in position B27 is substituted for Glu (E) Asp (D), or Pro (P); and/or the amino acid residue located in position B28 is substituted for Glu (E), Asp (D) or Arg (R); provided, however;

if the amino acid residue located in position B27 is substituted for Pro (P); then the amino acid residue located in position B28 is substituted for Glu (E), Asp (D) or Arg (R); and if the amino acid residue located in position B28 is not substituted, then the amino acid residue located in position B29 is substituted for B29Arg (R), or if the amino acid residue located in position B28 is substituted for Glu (E) or Asp (D), then the amino acid residue located in position B29 is substituted for B29Pro (P) or B29Arg (R), and if the amino acid residue located in position B29 is Pro (P), then the amino acid residue located in position B30 is substituted for B30Arg (R); and if the amino acid residue located in position B28 is substituted for Arg (R), then the amino acid residues located in positions B29 and B30 have been deleted (i.e. desB29, desB30); and if the amino acid residue located in position B29 is substituted for Arg (R), then the amino acid residue located in position B30 has been deleted (i.e. desB30); and which analogue may additionally comprise an A8Arg (R) and/or an A14Glu (E) substitution; and which insulin analogue is derivatized by acylation of the epsilon amino group of the lysine residue at the A22 position with a group of Formula II

[Acyl]-[Linker]- wherein the Linker group is an amino acid chain composed of from 1 to 10 amino acid residues selected from gGlu and/or OEG; wherein gGlu represents a gamma glutamic acid residue;

OEG represents a residue of 8-amino-3,6-dioxaoctanoic acid (i.e. a group of the formula —NH—(CH$_2$)$_2$—O—(CH$_2$)$_2$—O—CH$_2$—CO—);

which amino acid residues may be present in any order; and which amino acid chain comprises at least one gGlu residue; and wherein the Acyl group is a residue of an α,ω-di-carboxylic acid selected from 1,14-tetradecanedioic acid; 1,15-pentadecanedioic acid; and 1,16-hexadecanedioic acid.

In another aspect, the invention provides pharmaceutical compositions comprising the insulin derivative of the invention, and one or more pharmaceutically acceptable excipients.

In a further aspect, the invention relates to use of the insulin derivative of the invention as a medicament.

In a yet further aspect the invention provides methods for the treatment, prevention or alleviation of diseases, disorders or conditions relating to diabetes, Type 1 diabetes, Type 2 diabetes, impaired glucose tolerance, hyperglycemia, dyslipidemia, obesity, metabolic syndrome (metabolic syndrome X, insulin resistance syndrome), hypertension, cognitive disorders, atherosclerosis, myocardial infarction, stroke, cardiovascular disorders, coronary heart disease, inflammatory bowel syndrome, dyspepsia, or gastric ulcers, which method comprises administration to a subject in need thereof a therapeutically effective amount of the insulin derivative of the invention.

Other objects of the invention will be apparent to the person skilled in the art from the following detailed description and examples.

DETAILED DESCRIPTION OF THE INVENTION

Insulin Derivatives

In its first aspect the present invention provides novel insulin derivatives, which insulin derivative are acylated analogues of human insulin.

The insulin derivative of the invention may in particular be characterised as an acylated analogue of human insulin, which analogue is [A22Lys, B3aar¹] relative to human insulin; and wherein aar¹ represents Glu (E), Gln (Q), Asp (D), Ser (S) or Thr (T); and one, two or three of the amino acid residues located in positions B26, B27 and/or B28 are substituted as follows:

the amino acid residue (i.e. Tyr) located in position B26 is substituted for Glu (E) or Asp (D); and/or the amino acid residue (i.e. Thr) located in position B27 is substituted for Glu (E) Asp (D), or Pro (P); and/or the amino acid residue (i.e. Pro) located in position B28 is substituted for Glu (E), Asp (D) or Arg (R); provided, however;

if the amino acid residue (i.e. Thr) located in position B27 is substituted for Pro (P); then the amino acid residue (i.e. Pro) located in position B28 is substituted for Glu (E), Asp (D) or Arg (R); and if the amino acid residue (i.e. Pro) located in position B28 is not substituted, then the amino acid residue located in position B29 is substituted for B29Arg (R), or if the amino acid residue (i.e. Pro) located in position B28 is substituted for Glu (E) or Asp (D), then the amino acid residue (i.e. Lys) located in position B29 is substituted for B29Pro (P) or B29Arg (R), and if the amino acid residue (i.e. Lys) located in position B29 is Pro (P), then the amino acid residue (i.e. Thr) located in position B30 is substituted for B30Arg (R); and if the amino acid residue (i.e. Pro) located in position B28 is substituted for Arg (R), then the amino acid residues (i.e. Lys and Thr) located in positions B29 and B30 have been deleted (i.e. desB29, desB30); and if the amino acid residue (i.e. Lys) located in position B29 is substituted for Arg (R), then the amino acid residue (i.e. Thr) located in position B30 has been deleted (i.e. desB30); and which analogue may additionally comprise an A8Arg (R) and/or an A14Glu (E) substitution; and which insulin analogue is derivatized by acylation of the epsilon amino group of the lysine residue at the A22 position with a group of Formula II

[Acyl]-[Linker]- wherein the Linker group is an amino acid chain composed of from 1 to 10 amino acid residues selected from gGlu and/or OEG; wherein gGlu represents a gamma glutamic acid residue;

OEG represents a residue of 8-amino-3,6-dioxaoctanoic acid (i.e. a group of the formula —NH—(CH$_2$)$_2$—O—(CH$_2$)$_2$—O—CH$_2$—CO—);

which amino acid residues may be present in any order; and which amino acid chain comprises at least one gGlu residue; and wherein the Acyl group is a residue of an α,ω-di-carboxylic acid selected from 1,14-tetradecanedioic acid; 1,15-pentadecanedioic acid; and 1,16-hexadecanedioic acid.

PREFERRED FEATURES OF THE INVENTION

The acylated analogue of human insulin of the invention may be further characterised by reference to one or more of the following clauses:

1. An acylated analogue of human insulin, which analogue is [A22Lys; B3aar$^1$; B29Arg; desB30] relative to human insulin; wherein
   aar$^1$ represents Glu (E), Gln (Q), Asp (D), Ser (S) or Thr (T); and
   one, two or three of the amino acid residues located in positions B26, B27 and/or B28 are substituted with Glu (E) or Asp (D).

2. An acylated analogue of the invention, wherein aar$^1$ represents Glu (E), Gln (Q), Asp (D), Gly (G), Ser (S) or Thr (T).

3. An acylated analogue of the invention, wherein aar$^1$ represents Glu (E) or Gln (Q).

4. An acylated analogue of human insulin, which analogue is [A22Lys; B3aar$^1$; B26aar$^2$; B29Arg; desB30] relative to human insulin; wherein aar$^1$ represents Glu (E), Gln (Q), Asp (D), Ser (S) or Thr (T); and aar$^2$ represents Glu (E) or Asp (D).

5. An acylated analogue of human insulin, which analogue is [A22Lys; B3aar$^1$; B26aar$^2$; B29Arg; desB30] relative to human insulin; wherein aar$^1$ represents Glu (E) or Gln (Q); and aar$^2$ represents Glu (E).

6. An acylated analogue of human insulin, which analogue is [A22Lys; B3aar$^1$; B26aar$^2$; B29Arg; desB30] relative to human insulin; wherein aar$^1$ represents Glu (E); and aar$^2$ represents Glu (E).

7. The acylated analogue of clause 4, wherein the [A22Lys; B3aar$^1$; B26aar$^2$; B29Arg; desB30] analogue is
   A22K(N(eps)tetradecanedioyl-4×gGlu), B3E, B26E, B29R, desB30 human insulin;
   A22K(N(eps)tetradecanedioyl-4×gGlu), B3Q, B26E, B29R, desB30 human insulin;
   A22K(N(eps)hexadecanedioyl-4×gGlu), B3E, B26E, B29R, desB30 human insulin;
   A22K(N(eps)hexadecanedioyl-gGlu-2×OEG), B3E, B26E, B29R, desB30 human insulin;
   A22K(N(eps)hexadecanedioyl-gGlu-4×OEG), B3E, B26E, B29R, desB30 human insulin;
   A22K(N(eps)hexadecanedioyl-gGlu-6×OEG), B3E, B26E, B29R, desB30 human insulin;
   A22K(N(eps)hexadecanedioyl-4×gGlu-2×OEG), B3E, B26E, B29R, desB30 human insulin;
   A22K(N(eps)hexadecanedioyl-4×gGlu), B3Q, B26E, B29R, desB30 human insulin.

8. An acylated analogue of human insulin, which analogue is [A22Lys; B3aar$^1$; B27aar$^3$; B29Arg; desB30] relative to human insulin; wherein aar$^1$ represents Glu (E), Gln (Q), Asp (D), Ser (S) or Thr (T); and aar$^3$ represents Glu (E) or Asp (D).

9. An acylated analogue of human insulin, which analogue is [A22Lys; B3aar$^1$; B27aar$^3$; B29Arg; desB30] relative to human insulin; wherein aar$^1$ represents Glu (E); and aar$^3$ represents Glu (E).

10. The acylated analogue of clause 8, wherein the [A22Lys; B3aar$^1$; B27aar$^3$; B29Arg; desB30] analogue is
    A22K(N(eps)tetradecanedioyl-4×gGlu), B3E, B27E, B29R, desB30 human insulin;
    A22K(N(eps)hexadecanedioyl-gGlu-2×OEG), B3E, B27E, B29R, desB30 human insulin; or
    A22K(N(eps)hexadecanedioyl-4×gGlu), B3E, B27E, B29R, desB30 human insulin.

11. An acylated analogue of human insulin, which analogue is [A22Lys; B3aar$^1$; B27Pro; B28aar$^4$; B29Pro; B30Arg] relative to human insulin; wherein aar$^1$ represents Glu (E), Gln (Q), Asp (D), Ser (S) or Thr (T); and aar$^4$ represents Glu (E) or Asp (D).

12. An acylated analogue of human insulin, which analogue is [A22Lys; B3aar$^1$; B27Pro; B28aar$^4$; B29Arg; desB30] relative to human insulin; wherein aar$^1$ represents Glu (E), Gln (Q), Asp (D), Ser (S) or Thr (T); and aar$^4$ represents Glu (E) or Asp (D).

13. An acylated analogue of human insulin, which analogue is [A22Lys; B3aar$^1$; B27Pro; B28aar$^4$; B29Arg; desB30] relative to human insulin; wherein aar$^1$ represents Glu (E); and aar$^4$ represents Glu (E).

14. The acylated analogue of clause 12, wherein the [A22Lys; B3aar$^1$; B27Pro; B28aar$^4$; B29Arg; desB30] analogue is
    A22K(N(eps)tetradecanedioyl-gGlu-2×OEG), B3E, B27P, B28E, B29R, desB30 human insulin;
    A22K(N(eps)tetradecanedioyl-4×gGlu), B3E, B27P, B28E, B29R, desB30 human insulin;
    A22K(N(eps)hexadecanedioyl-gGlu-2×OEG), B3E, B27P, B28E, B29R, desB30 human insulin; or
    A22K(N(eps)hexadecanedioyl-4×gGlu), B3E, B27P, B28E, B29R, desB30 human insulin.

15. An acylated analogue of human insulin, which analogue is [A22Lys; B3aar$^1$; B27Pro; B28Arg; desB29; desB30] relative to human insulin; wherein aar$^1$ represents Glu (E), Gln (Q), Asp (D), Ser (S) or Thr (T).

16. An acylated analogue of human insulin, which analogue is [A22Lys; B3aar$^1$; B28aar$^4$; B29Arg; desB30] relative to human insulin; wherein aar$^1$ represents Glu (E), Gln (Q), Asp (D), Ser (S) or Thr (T); and aar$^4$ represents Glu (E) or Asp (D).

17. An acylated analogue of human insulin, which analogue is [A22Lys; B3aar$^1$; B28aar$^4$; B29Arg; desB30] relative to human insulin; wherein aar$^1$ represents Glu (E); and aar$^4$ represents Asp (D).

18. The acylated analogue of clause 16, wherein the [A22Lys; B3aar$^1$; B28aar$^4$; B29Arg; desB30] analogue is
    A22K(N(eps)tetradecanedioyl-gGlu-2×OEG), B3E, B28D, B29R, desB30 human insulin;
    A22K(N(eps)tetradecanedioyl-4×gGlu), B3E, B28D, B29R, desB30 human insulin;
    A22K(N(eps)hexadecanedioyl-gGlu-2×OEG), B3E, B28D, B29R, desB30 human insulin; or
    A22K(N(eps)hexadecanedioyl-4×gGlu), B3E, B28D, B29R, desB30 human insulin.

19. An acylated analogue of human insulin, which analogue is [A22Lys; B3aar$^1$; B28aar$^4$; B29Pro; B30Arg] relative to human insulin; wherein aar$^1$ represents Glu (E), Gln (Q), Asp (D), Ser (S) or Thr (T); and aar$^4$ represents Glu (E) or Asp (D).

20. An acylated analogue of human insulin, which analogue is [A22Lys; B3aar$^1$; B28aar$^4$; B29Pro; B30Arg] relative to human insulin; wherein aar$^1$ represents Glu (E); and aar$^4$ represents Glu (E).

21. The acylated analogue of clause 19, wherein the [A22Lys; B3aar$^1$; B28aar$^4$; B29Pro; B30Arg] analogue is
    A22K(N(eps)tetradecanedioyl-4×gGlu), B3E, B28E, B29P, B30R human insulin.

22. An acylated analogue of human insulin, which analogue is [A22Lys; B3aar¹; B28Arg; desB29; desB30] relative to human insulin; wherein aar¹ represents Glu (E), Gln (Q), Asp (D), Ser (S) or Thr (T).

23. An acylated analogue of human insulin, which analogue is [A22Lys; B3aar¹; B26aar²; B27aar³; B29Arg; desB30] relative to human insulin; wherein aar¹ represents Glu (E), Gln (Q), Asp (D), Ser (S) or Thr (T); aar² represents Glu (E) or Asp (D); and aar³ represents Glu (E) or Asp (D).

24. An acylated analogue of human insulin, which analogue is [A22Lys; B3aar¹; B26aar²; B27Pro; B28aar⁴; B29Pro; B30Arg] relative to human insulin; wherein aar¹ represents Glu (E), Gln (Q), Asp (D), Ser (S) or Thr (T); aar² represents Glu (E) or Asp (D); and aar⁴ represents Glu (E) or Asp (D).

25. An acylated analogue of human insulin, which analogue is [A22Lys; B3aar¹; B26aar²; B27Pro; B28aar⁴; B29Arg; desB30] relative to human insulin; wherein aar¹ represents Glu (E), Gln (Q), Asp (D), Ser (S) or Thr (T); aar² represents Glu (E) or Asp (D); and aar⁴ represents Glu (E) or Asp (D).

26. An acylated analogue of human insulin, which analogue is [A22Lys; B3aar¹; B26aar²; B27Pro; B28Arg; desB29; desB30] relative to human insulin; wherein aar¹ represents Glu (E), Gln (Q), Asp (D), Ser (S) or Thr (T); and aar² represents Glu (E) or Asp (D).

27. An acylated analogue of human insulin, which analogue is [A22Lys; B3aar¹; B26aar²; B27Pro; B28Arg; desB29; desB30] relative to human insulin; wherein aar¹ represents Glu (E); and aar² represents Glu (E).

28. The acylated analogue of clause 26, wherein the [A22Lys; B3aar¹; B26aar²; B27Pro; B28Arg; desB29; desB30] analogue is
A22K(N(eps)tetradecanedioyl-4×gGlu), B3E, B26E, B27P, B28R, desB29, desB30 human insulin.

29. An acylated analogue of human insulin, which analogue is [A22Lys; B3aar¹; B26aar²; B28aar⁴; B29Arg; desB30] relative to human insulin; wherein aar¹ represents Glu (E), Gln (Q), Asp (D), Ser (S) or Thr (T); aar² represents Glu (E) or Asp (D); and aar⁴ represents Glu (E) or Asp (D).

30. An acylated analogue of human insulin, which analogue is [A22Lys; B3aar¹; B26aar²; B28aar⁴; B29Arg; desB30] relative to human insulin; wherein aar¹ represents Glu (E) or Gln (Q); aar² represents Glu (E); and aar⁴ represents Glu (E) or Asp (D).

31. An acylated analogue of human insulin, which analogue is [A22Lys; B3aar¹; B26aar²; B28aar⁴; B29Arg; desB30] relative to human insulin; wherein aar¹ represents Glu (E); aar² represents Glu (E); and aar⁴ represents Glu (E) or Asp (D).

32. The acylated analogue of clause 29, wherein the [A22Lys; B3aar¹; B26aar²; B28aar⁴; B29Arg; desB30] analogue is
A22K(N(eps)tetradecanedioyl-4×gGlu), B3E, B26E, B28E, B29R, desB30 human insulin;
A22K(N(eps)tetradecanedioyl-4×gGlu), B3E, B26E, B28D, B29R, desB30 human insulin; or
A22K(N(eps)tetradecanedioyl-4×gGlu), B3Q, B26E, B28E, B29R, desB30 human insulin.

33. An acylated analogue of human insulin, which analogue is [A22Lys; B3aar¹; B26aar²; B28aar⁴; B29Pro; B30Arg] relative to human insulin; wherein aar¹ represents Glu (E), Gln (Q), Asp (D), Ser (S) or Thr (T); aar² represents Glu (E) or Asp (D); and aar⁴ represents Glu (E) or Asp (D).

34. An acylated analogue of human insulin, which analogue is [A22Lys; B3aar¹; B26aar²; B28aar⁴; B29Pro; B30Arg] relative to human insulin; wherein aar¹ represents Glu (E); aar² represents Glu (E); and aar⁴ represents Glu (E).

35. The acylated analogue of clause 33, wherein the [A22Lys; B3aar¹; B26aar²; B28aar⁴; B29Pro; B30Arg] analogue is
A22K(N(eps)tetradecanedioyl-4×gGlu), B3E, B26E, B28E, B29P, B30R human insulin.

36. An acylated analogue of human insulin, which analogue is [A22Lys; B3aar¹; B26aar²; B28Arg; desB29; desB30] relative to human insulin; wherein aar¹ represents Glu (E), Gln (Q), Asp (D), Ser (S) or Thr (T); and aar² represents Glu (E) or Asp (D).

37. An acylated analogue of human insulin, which analogue is [A22Lys; B3aar¹; B27aar³; B28aar⁴; B29Arg; desB30] relative to human insulin; wherein aar¹ represents Glu (E), Gln (Q), Asp (D), Ser (S) or Thr (T); aar³ represents Glu (E) or Asp (D); and aar⁴ represents Glu (E) or Asp (D).

38. An acylated analogue of human insulin, which analogue is [A22Lys; B3aar¹; B27aar³; B28aar⁴; B29Arg; desB30] relative to human insulin; wherein aar¹ represents Glu (E); aar³ represents Glu (E); and aar⁴ represents Glu (E).

39. The acylated analogue of clause 37, wherein the [A22Lys; B3aar¹; B27aar³; B28aar⁴; B29Arg; desB30] analogue is
A22K(N(eps)tetradecanedioyl-gGlu-2×OEG), B3E, B27E, B28E, B29R, desB30 human insulin;
A22K(N(eps)tetradecanedioyl-4×gGlu), B3E, B27E, B28E, B29R, desB30 human insulin;
A22K(N(eps)hexadecanedioyl-4×gGlu), B3E, B27E, B28E, B29R, desB30 human insulin; or
A22K(N(eps)hexadecanedioyl-gGlu-2×OEG), B3E, B27E, B28E, B29R, desB30 human insulin.

40. An acylated analogue of human insulin, which analogue is [A22Lys; B3aar¹; B27aar³; B28aar⁴; B29Pro; B30Arg] relative to human insulin; wherein aar¹ represents Glu (E), Gln (Q), Asp (D), Ser (S) or Thr (T); aar³ represents Glu (E) or Asp (D); and aar⁴ represents Glu (E) or Asp (D).

41. An acylated analogue of human insulin, which analogue is [A22Lys; B3aar¹; B27aar³; B28aar⁴; B29Pro; B30Arg] relative to human insulin; wherein aar¹ represents Glu (E); aar³ represents Glu (E); and aar⁴ represents Glu (E).

42. The acylated analogue of clause 40, wherein the [A22Lys; B3aar¹; B27aar³; B28aar⁴; B29Pro; B30Arg] analogue is
A22K(N(eps)tetradecanedioyl-4×gGlu), B3E, B27E, B28E, B29P, B30R human insulin.

43. An acylated analogue of human insulin, which analogue is [A22Lys; B3aar¹; B27aar³; B28Arg; desB29; desB30] relative to human insulin; wherein aar¹ represents Glu (E), Gln (Q), Asp (D), Ser (S) or Thr (T); and aar³ represents Glu (E) or Asp (D).

44. An acylated analogue of human insulin, which analogue is [A22Lys; B3aar¹; B27aar³; B28Arg; desB29; desB30] relative to human insulin; wherein aar¹ represents Glu (E); and aar³ represents Glu (E).

45. The acylated analogue of clause 43, wherein the [A22Lys; B3aar¹; B27aar³; B28Arg; desB29; desB30] analogue is
A22K(N(eps)tetradecanedioyl-4×gGlu), B3E, B27E, B28R, desB29, desB30 human insulin.

46. An acylated analogue of human insulin, which analogue is [A22Lys; B3aar¹; B27Pro; B28aar⁴; B29Arg; desB30] relative to human insulin; wherein aar¹ represents Glu (E), Gln (Q), Asp (D), Ser (S) or Thr (T); and aar⁴ represents Glu (E) or Asp (D).

47. An acylated analogue of human insulin, which analogue is [A22Lys; B3aar¹; B27Pro; B28aar⁴; B29Pro;

B30Arg] relative to human insulin; wherein aar¹ represents Glu (E), Gln (Q), Asp (D), Ser (S) or Thr (T); and aar⁴ represents Glu (E) or Asp (D).

48. An acylated analogue of human insulin, which analogue is [A22Lys; B3aar¹; B27Pro; B28Arg; desB29; desB30] relative to human insulin; wherein aar¹ represents Glu (E), Gln (Q), Asp (D), Ser (S) or Thr (T).

49. An acylated analogue of human insulin, which analogue is [A22Lys; B3aar¹; B26aar²; B27aar³; B28aar⁴; B29Arg; desB30] relative to human insulin; wherein aar¹ represents Glu (E), Gln (Q), Asp (D), Ser (S) or Thr (T); aar² represents Glu (E) or Asp (D); aar³ represents Glu (E) or Asp (D); and aar⁴ represents Glu (E) or Asp (D).

50. An acylated analogue of human insulin, which analogue is [A22Lys; B3aar¹; B26aar²; B27aar³; B28aar⁴; B29Arg; desB30] relative to human insulin; wherein aar¹ represents Glu (E); aar² represents Glu (E); aar³ represents Glu (E); and aar⁴ represents Glu (E).

51. The acylated analogue of clause 49, wherein the [A22Lys; B3aar¹; B26aar²; B27aar³; B28aar⁴; B29Arg; desB30] insulin analogue is
A22K(N(eps)tetradecanedioyl-4×gGlu), B3E, B26E, B27E, B28E, B29R, desB30 human insulin.

52. An acylated analogue of human insulin, which analogue is [A22Lys; B3aar¹; B26aar²; B27aar³; B28Arg; desB29; desB30] relative to human insulin; wherein aar¹ represents Glu (E), Gln (Q), Asp (D), Ser (S) or Thr (T); aar² represents Glu (E) or Asp (D); and aar³ represents Glu (E) or Asp (D).

53. An acylated analogue of human insulin, which analogue is [A22Lys; B3aar¹; B26aar²; B27aar³; B28Arg; desB29; desB30] relative to human insulin; wherein aar¹ represents Glu (E); aar² represents Glu (E); and aar³ represents Glu (E).

54. The acylated analogue of clause 52, wherein the [A22Lys; B3aar¹; B26aar²; B27aar³; B28Arg; desB29; desB30] analogue is
A22K(N(eps)tetradecanedioyl-4×gGlu), B3E, B26E, B27E, B28R, desB29, desB30 human insulin.

55. An acylated analogue of human insulin, which analogue is [A22Lys; B3aar¹; B26aar²; B27Pro; B28aar⁴; B29Arg; desB30] relative to human insulin; wherein aar¹ represents Glu (E), Gln (Q), Asp (D), Ser (S) or Thr (T); aar² represents Glu (E) or Asp (D); and aar⁴ represents Glu (E) or Asp (D).

56. An acylated analogue of human insulin, which analogue is [A22Lys; B3aar¹; B26aar²; B27Pro; B28aar⁴; B29Pro; B30Arg] relative to human insulin; wherein aar¹ represents Glu (E), Gln (Q), Asp (D), Ser (S) or Thr (T); aar² represents Glu (E) or Asp (D); and aar⁴ represents Glu (E) or Asp (D).

57. An acylated analogue of human insulin, which analogue is [A22Lys; B3aar¹; B26aar²; B27aar³; B29Pro; B30Arg] relative to human insulin; wherein aar¹ represents Glu (E), Gln (Q), Asp (D), Ser (S) or Thr (T); aar² represents Glu (E) or Asp (D); and aar³ represents Glu (E) or Asp (D).

58. An acylated analogue of human insulin, which analogue is [A22Lys; B3aar¹; B26aar²; B27aar³; B29Pro; B30Arg] relative to human insulin; wherein aar¹ represents Glu (E); aar² represents Glu (E); and aar³ represents Glu (E).

59. The acylated analogue of clause 57, wherein the [A22Lys; B3aar¹; B26aar²; B27aar³; B29Pro; B30Arg] analogue is
A22K(N(eps)tetradecanedioyl-4×gGlu), B3E, B26E, B27E, B29P, B30R human insulin.

60. An acylated analogue of human insulin, which analogue is [A8Arg; A22Lys; B3aar¹; B26aar²; B29Arg; desB30] relative to human insulin; wherein aar¹ represents Glu (E), Gln (Q), Asp (D), Ser (S) or Thr (T); and aar² represents Glu (E) or Asp (D).

61. An acylated analogue of human insulin, which analogue is [A8Arg; A22Lys; B3aar¹; B26aar²; B29Arg; desB30] relative to human insulin; wherein aar¹ represents Glu (E); and aar² represents Glu (E).

62. The acylated analogue of clause 60, wherein the [A8Arg; A22Lys; B3aar¹; B26aar²; B29Arg; desB30] analogue is
A8R, A22K(N(eps)tetradecanedioyl-4×gGlu), B3E, B26E, B29R, desB30 human insulin.

63. An acylated analogue of human insulin, which analogue is [A8Arg; A22Lys; B3aar¹; B27aar³; B29Arg; desB30] relative to human insulin; wherein aar¹ represents Glu (E), Gln (Q), Asp (D), Ser (S) or Thr (T); and aar³ represents Glu (E) or Asp (D).

64. An acylated analogue of human insulin, which analogue is [A8Arg; A22Lys; B3aar¹; B27Pro; B28aar⁴; B29Pro; B30Arg] relative to human insulin; wherein aar¹ represents Glu (E), Gln (Q), Asp (D), Ser (S) or Thr (T); and aar⁴ represents Glu (E) or Asp (D).

65. An acylated analogue of human insulin, which analogue is [A8Arg; A22Lys; B3aar¹; B27Pro; B28aar⁴; B29Arg; desB30] relative to human insulin; wherein aar¹ represents Glu (E), Gln (Q), Asp (D), Ser (S) or Thr (T); and aar⁴ represents Glu (E) or Asp (D).

66. An acylated analogue of human insulin, which analogue is [A8Arg; A22Lys; B3aar¹; B27Pro; B28Arg; desB29; desB30] relative to human insulin; wherein aar¹ represents Glu (E), Gln (Q), Asp (D), Ser (S) or Thr (T).

67. An acylated analogue of human insulin, which analogue is [A8Arg; A22Lys; B3aar¹; B28aar⁴; B29Arg; desB30] relative to human insulin; wherein aar¹ represents Glu (E), Gln (Q), Asp (D), Ser (S) or Thr (T); and aar⁴ represents Glu (E) or Asp (D).

68. An acylated analogue of human insulin, which analogue is [A8Arg; A22Lys; B3aar¹; B28aar⁴; B29Pro; B30Arg] relative to human insulin; wherein aar¹ represents Glu (E), Gln (Q), Asp (D), Ser (S) or Thr (T); and aar⁴ represents Glu (E) or Asp (D).

69. An acylated analogue of human insulin, which analogue is [A8Arg; A22Lys; B3aar¹; B28Arg; desB29; desB30] relative to human insulin; wherein aar¹ represents Glu (E), Gln (Q), Asp (D), Ser (S) or Thr (T).

70. An acylated analogue of human insulin, which analogue is [A8Arg; A22Lys; B3aar¹; B26aar²; B27aar³; B29Arg; desB30] relative to human insulin; wherein aar¹ represents Glu (E), Gln (Q), Asp (D), Ser (S) or Thr (T); aar² represents Glu (E) or Asp (D); and aar³ represents Glu (E) or Asp (D).

71. An acylated analogue of human insulin, which analogue is [A8Arg; A22Lys; B3aar¹; B26aar²; B27Pro; B28aar⁴; B29Pro; B30Arg] relative to human insulin; wherein aar¹ represents Glu (E), Gln (Q), Asp (D), Ser (S) or Thr (T); aar² represents Glu (E) or Asp (D); and aar⁴ represents Glu (E) or Asp (D).

72. An acylated analogue of human insulin, which analogue is [A8Arg; A22Lys; B3aar¹; B26aar²; B27Pro; B28aar⁴; B29Arg; desB30] relative to human insulin; wherein aar¹ represents Glu (E), Gln (Q), Asp (D), Ser (S) or Thr (T); aar² represents Glu (E) or Asp (D); and aar⁴ represents Glu (E) or Asp (D).

73. An acylated analogue of human insulin, which analogue is [A8Arg; A22Lys; B3aar¹; B26aar²; B27Pro; B28Arg; desB29; desB30] relative to human insulin;

wherein aar¹ represents Glu (E), Gln (Q), Asp (D), Ser (S) or Thr (T); and aar² represents Glu (E) or Asp (D).

74. An acylated analogue of human insulin, which analogue is [A8Arg; A22Lys; B3aar¹; B26aar²; B27Pro; B28Arg; desB29; desB30] relative to human insulin; wherein aar¹ represents Glu (E); and aar² represents Glu (E).

75. The acylated analogue of clause 73, wherein the [A8Arg; A22Lys; B3aar¹; B26aar²; B27Pro; B28Arg; desB29; desB30] analogue is
A8R, A22K(N(eps)tetradecanedioyl-4×gGlu), B3E, B26E, B27P, B28R, desB29, desB30 human insulin.

76. An acylated analogue of human insulin, which analogue is [A8Arg; A22Lys; B3aar¹; B26aar²; B28aar⁴; B29Arg; desB30] relative to human insulin; wherein aar¹ represents Glu (E), Gln (Q), Asp (D), Ser (S) or Thr (T); aar² represents Glu (E) or Asp (D); and aar⁴ represents Glu (E) or Asp (D).

77. An acylated analogue of human insulin, which analogue is [A8Arg; A22Lys; B3aar¹; B26aar²; B28aar⁴; B29Arg; desB30] relative to human insulin; wherein aar¹ represents Glu (E); aar² represents Glu (E); and aar⁴ represents Glu (E).

78. The acylated analogue of clause 76, wherein the [A8Arg; A22Lys; B3aar¹; B26aar²; B28aar⁴; B29Arg; desB30] analogue is
A8R, A22K(N(eps)tetradecanedioyl-4×gGlu), B3E, B26E, B28E, B29R, desB30 human insulin.

79. An acylated analogue of human insulin, which analogue is [A8Arg; A22Lys; B3aar¹; B26aar²; B28aar⁴; B29Pro; B30Arg] relative to human insulin; wherein aar¹ represents Glu (E), Gln (Q), Asp (D), Ser (S) or Thr (T); aar² represents Glu (E) or Asp (D); and aar⁴ represents Glu (E) or Asp (D).

80. An acylated analogue of human insulin, which analogue is [A8Arg; A22Lys; B3aar¹; B26aar²; B28Arg; desB29; desB30] relative to human insulin; wherein aar¹ represents Glu (E), Gln (Q), Asp (D), Ser (S) or Thr (T); and aar² represents Glu (E) or Asp (D).

81. An acylated analogue of human insulin, which analogue is [A8Arg; A22Lys; B3aar¹; B27aar³; B28aar⁴; B29Arg; desB30] relative to human insulin; wherein aar¹ represents Glu (E), Gln (Q), Asp (D), Ser (S) or Thr (T); aar³ represents Glu (E) or Asp (D); and aar⁴ represents Glu (E) or Asp (D).

82. An acylated analogue of human insulin, which analogue is [A8Arg; A22Lys; B3aar¹; B27aar³; B28aar⁴; B29Arg; desB30] relative to human insulin; wherein aar¹ represents Glu (E); aar³ represents Glu (E); and aar⁴ represents Glu (E).

83. The acylated analogue of clause 81, wherein the [A8Arg; A22Lys; B3aar¹; B27aar³; B28aar⁴; B29Arg; desB30] analogue is
A8R, A22K(N(eps)tetradecanedioyl-4×gGlu), B3E, B27E, B28E, B29R, desB30 human insulin.

84. An acylated analogue of human insulin, which analogue is [A8Arg; A22Lys; B3aar¹; B27aar³; B28aar⁴; B29Pro; B30Arg] relative to human insulin; wherein aar¹ represents Glu (E), Gln (Q), Asp (D), Ser (S) or Thr (T); aar³ represents Glu (E) or Asp (D); and aar⁴ represents Glu (E) or Asp (D).

85. An acylated analogue of human insulin, which analogue is [A8Arg; A22Lys; B3aar¹; B27aar³; B28Arg; desB29; desB30] relative to human insulin; wherein aar¹ represents Glu (E), Gln (Q), Asp (D), Ser (S) or Thr (T); and aar³ represents Glu (E) or Asp (D).

86. An acylated analogue of human insulin, which analogue is [A8Arg; A22Lys; B3aar¹; B27aar³; B28Arg; desB29; desB30] relative to human insulin; wherein aar¹ represents Glu (E); and aar³ represents Glu (E).

87. The acylated analogue of clause 85, wherein the [A8Arg; A22Lys; B3aar¹; B27aar³; B28Arg; desB29; desB30] analogue is
A8R, A22K(N(eps)tetradecanedioyl-4×gGlu), B3E, B27E, B28R, desB29, desB30 human insulin.

88. An acylated analogue of human insulin, which analogue is [A8Arg; A22Lys; B3aar¹; B27Pro; B28aar⁴; B29Arg; desB30] relative to human insulin; wherein aar¹ represents Glu (E), Gln (Q), Asp (D), Ser (S) or Thr (T); and aar⁴ represents Glu (E) or Asp (D).

89. An acylated analogue of human insulin, which analogue is [A8Arg; A22Lys; B3aar¹; B27Pro; B28aar⁴; B29Pro; B30Arg] relative to human insulin; wherein aar¹ represents Glu (E), Gln (Q), Asp (D), Ser (S) or Thr (T); and aar⁴ represents Glu (E) or Asp (D).

90. An acylated analogue of human insulin, which analogue is [A8Arg; A22Lys; B3aar¹; B27Pro; B28Arg; desB29; desB30] relative to human insulin; wherein aar¹ represents Glu (E), Gln (Q), Asp (D), Ser (S) or Thr (T).

91. An acylated analogue of human insulin, which analogue is [A8Arg; A22Lys; B3aar¹; B26aar²; B27aar³; B28aar⁴; B29Arg; desB30] relative to human insulin; wherein aar¹ represents Glu (E), Gln (Q), Asp (D), Ser (S) or Thr (T); aar² represents Glu (E) or Asp (D); aar³ represents Glu (E) or Asp (D); and aar⁴ represents Glu (E) or Asp (D).

92. An acylated analogue of human insulin, which analogue is [A8Arg; A22Lys; B3aar¹; B26aar²; B27aar³; B28Arg; desB29; desB30] relative to human insulin; wherein aar¹ represents Glu (E), Gln (Q), Asp (D), Ser (S) or Thr (T); aar² represents Glu (E) or Asp (D); and aar³ represents Glu (E) or Asp (D).

93. An acylated analogue of human insulin, which analogue is [A8Arg; A22Lys; B3aar¹; B26aar²; B27aar³; B28Arg; desB29; desB30] relative to human insulin; wherein aar¹ represents Glu (E); aar² represents Glu (E); and aar³ represents Glu (E).

94. The acylated analogue of clause 92, wherein the [A8Arg; A22Lys; B3aar¹; B26aar²; B27aar³; B28Arg; desB29; desB30] analogue is
A8R, A22K(N(eps)tetradecanedioyl-4×gGlu), B3E, B26E, B27E, B28R, desB29, desB30 human insulin.

95. An acylated analogue of human insulin, which analogue is [A8Arg; A22Lys; B3aar¹; B26aar²; B27Pro; B28aar⁴; B29Arg; desB30] relative to human insulin; wherein aar¹ represents Glu (E), Gln (Q), Asp (D), Ser (S) or Thr (T); aar² represents Glu (E) or Asp (D); and aar⁴ represents Glu (E) or Asp (D).

96. An acylated analogue of human insulin, which analogue is [A8Arg; A22Lys; B3aar¹; B26aar²; B27Pro; B28aar⁴; B29Pro; B30Arg] relative to human insulin; wherein aar¹ represents Glu (E), Gln (Q), Asp (D), Ser (S) or Thr (T); aar² represents Glu (E) or Asp (D); and aar⁴ represents Glu (E) or Asp (D).

97. An acylated analogue of human insulin, which analogue is [A14Glu; A22Lys; B3aar¹; B26aar²; B29Arg; desB30] relative to human insulin; wherein aar¹ represents Glu (E), Gln (Q), Asp (D), Ser (S) or Thr (T); and aar² represents Glu (E) or Asp (D).

98. An acylated analogue of human insulin, which analogue is [A14Glu; A22Lys; B3aar¹; B27aar³; B29Arg; desB30] relative to human insulin; wherein aar¹ represents Glu (E), Gln (Q), Asp (D), Ser (S) or Thr (T); and aar³ represents Glu (E) or Asp (D).

99. An acylated analogue of human insulin, which analogue is [A14Glu; A22Lys; B3aar$^1$; B27Pro; B28aar$^4$; B29Pro; B30Arg] relative to human insulin; wherein aar$^1$ represents Glu (E), Gln (Q), Asp (D), Ser (S) or Thr (T); and aar$^4$ represents Glu (E) or Asp (D).

100. An acylated analogue of human insulin, which analogue is [A14Glu; A22Lys; B3aar$^1$; B27Pro; B28aar$^4$; B29Arg; desB30] relative to human insulin; wherein aar$^1$ represents Glu (E), Gln (Q), Asp (D), Ser (S) or Thr (T); and aar$^4$ represents Glu (E) or Asp (D).

101. An acylated analogue of human insulin, which analogue is [A14Glu; A22Lys; B3aar$^1$; B27Pro; B28Arg; desB29; desB30] relative to human insulin; wherein aar$^1$ represents Glu (E), Gln (Q), Asp (D), Ser (S) or Thr (T).

102. An acylated analogue of human insulin, which analogue is [A14Glu; A22Lys; B3aar$^1$; B28aar$^4$; B29Arg; desB30] relative to human insulin; wherein aar$^1$ represents Glu (E), Gln (Q), Asp (D), Ser (S) or Thr (T); and aar$^4$ represents Glu (E) or Asp (D).

103. An acylated analogue of human insulin, which analogue is [A14Glu; A22Lys; B3aar$^1$; B28aar$^4$; B29Arg; desB30] relative to human insulin; wherein aar$^1$ represents Gln (Q); and aar$^4$ represents Asp (D).

104. The acylated analogue of clause 102, wherein the [A14Glu; A22Lys; B3aar$^1$; B28aar$^4$; B29Arg; desB30] analogue is
A14E, A22K(N(eps)tetradecanedioyl-4×gGlu), B3Q, B28D, B29R, desB30 human insulin.

105. An acylated analogue of human insulin, which analogue is [A14Glu; A22Lys; B3aar$^1$; B28aar$^4$; B29Pro; B30Arg] relative to human insulin; wherein aar$^1$ represents Glu (E), Gln (Q), Asp (D), Ser (S) or Thr (T); and aar$^4$ represents Glu (E) or Asp (D).

106. An acylated analogue of human insulin, which analogue is [A14Glu; A22Lys; B3aar$^1$; B28Arg; desB29; desB30] relative to human insulin; wherein aar$^1$ represents Glu (E), Gln (Q), Asp (D), Ser (S) or Thr (T).

107. An acylated analogue of human insulin, which analogue is [A14Glu; A22Lys; B3aar$^1$; B26aar$^2$; B27aar$^3$; B29Arg; desB30] relative to human insulin; wherein aar$^1$ represents Glu (E), Gln (Q), Asp (D), Ser (S) or Thr (T); aar$^2$ represents Glu (E) or Asp (D); and aar$^3$ represents Glu (E) or Asp (D).

108. An acylated analogue of human insulin, which analogue is [A14Glu; A22Lys; B3aar$^1$; B26aar$^2$; B27Pro; B28aar$^4$; B29Pro; B30Arg] relative to human insulin; wherein aar$^1$ represents Glu (E), Gln (Q), Asp (D), Ser (S) or Thr (T); aar$^2$ represents Glu (E) or Asp (D); and aar$^4$ represents Glu (E) or Asp (D).

109. An acylated analogue of human insulin, which analogue is [A14Glu; A22Lys; B3aar$^1$; B26aar$^2$; B27Pro; B28aar$^4$; B29Arg; desB30] relative to human insulin; wherein aar$^1$ represents Glu (E), Gln (Q), Asp (D), Ser (S) or Thr (T); aar$^2$ represents Glu (E) or Asp (D); and aar$^4$ represents Glu (E) or Asp (D).

110. An acylated analogue of human insulin, which analogue is [A14Glu; A22Lys; B3aar$^1$; B26aar$^2$; B27Pro; B28Arg; desB29; desB30] relative to human insulin; wherein aar$^1$ represents Glu (E), Gln (Q), Asp (D), Ser (S) or Thr (T); and aar$^2$ represents Glu (E) or Asp (D).

111. An acylated analogue of human insulin, which analogue is [A14Glu; A22Lys; B3aar$^1$; B26aar$^2$; B28aar$^4$; B29Arg; desB30] relative to human insulin; wherein aar$^1$ represents Glu (E), Gln (Q), Asp (D), Ser (S) or Thr (T); aar$^2$ represents Glu (E) or Asp (D); and aar$^4$ represents Glu (E) or Asp (D).

112. An acylated analogue of human insulin, which analogue is [A14Glu; A22Lys; B3aar$^1$; B26aar$^2$; B28aar$^4$; B29Pro; B30Arg] relative to human insulin; wherein aar$^1$ represents Glu (E), Gln (Q), Asp (D), Ser (S) or Thr (T); aar$^2$ represents Glu (E) or Asp (D); and aar$^4$ represents Glu (E) or Asp (D).

113. An acylated analogue of human insulin, which analogue is [A14Glu; A22Lys; B3aar$^1$; B26aar$^2$; B28Arg; desB29; desB30] relative to human insulin; wherein aar$^1$ represents Glu (E), Gln (Q), Asp (D), Ser (S) or Thr (T); and aar$^2$ represents Glu (E) or Asp (D).

114. An acylated analogue of human insulin, which analogue is [A14Glu; A22Lys; B3aar$^1$; B27aar$^3$; B28aar$^4$; B29Arg; desB30] relative to human insulin; wherein aar$^1$ represents Glu (E), Gln (Q), Asp (D), Ser (S) or Thr (T); aar$^3$ represents Glu (E) or Asp (D); and aar$^4$ represents Glu (E) or Asp (D).

115. An acylated analogue of human insulin, which analogue is [A14Glu; A22Lys; B3aar$^1$; B27aar$^3$; B28aar$^4$; B29Arg; desB30] relative to human insulin; wherein aar$^1$ represents Glu (E) or Gln (Q); aar$^3$ represents Glu (E); and aar$^4$ represents Glu (E).

116. The acylated analogue of clause 114, wherein the [A14Glu; A22Lys; B3aar$^1$; B27aar$^3$; B28aar$^4$; B29Arg; desB30] analogue is
A14E, A22K(N(eps)tetradecanedioyl-gGlu-2×OEG), B3E, B27E, B28E, B29R, desB30 human insulin;
A14E, A22K(N(eps)tetradecanedioyl-4×gGlu), B3E, B27E, B28E, B29R, desB30 human insulin;
A14E, A22K(N(eps)hexadecanedioyl-gGlu-2×OEG), B3E, B27E, B28E, B29R, desB30 human insulin;
A14E, A22K(N(eps)hexadecanedioyl-4×gGlu), B3E, B27E, B28E, B29R, desB30 human insulin; or
A14E, A22K(N(eps)tetradecanedioyl-4×gGlu), B3Q, B27E, B28E, B29R, desB30 human insulin.

117. An acylated analogue of human insulin, which analogue is [A14Glu; A22Lys; B3aar$^1$; B27aar$^3$; B28aar$^4$; B29Pro; B30Arg] relative to human insulin; wherein aar$^1$ represents Glu (E), Gln (Q), Asp (D), Ser (S) or Thr (T); aar$^3$ represents Glu (E) or Asp (D); and aar$^4$ represents Glu (E) or Asp (D).

118. An acylated analogue of human insulin, which analogue is [A14Glu; A22Lys; B3aar$^1$; B27aar$^3$; B28Arg; desB29; desB30] relative to human insulin; wherein aar$^1$ represents Glu (E), Gln (Q), Asp (D), Ser (S) or Thr (T); and aar$^3$ represents Glu (E) or Asp (D).

119. An acylated analogue of human insulin, which analogue is [A14Glu; A22Lys; B3aar$^1$; B27Pro; B28aar$^4$; B29Arg; desB30] relative to human insulin; wherein aar$^1$ represents Glu (E), Gln (Q), Asp (D), Ser (S) or Thr (T); and aar$^4$ represents Glu (E) or Asp (D).

120. An acylated analogue of human insulin, which analogue is [A14Glu; A22Lys; B3aar$^1$; B27Pro; B28aar$^4$; B29Pro; B30Arg] relative to human insulin; wherein aar$^1$ represents Glu (E), Gln (Q), Asp (D), Ser (S) or Thr (T); and aar$^4$ represents Glu (E) or Asp (D).

121. An acylated analogue of human insulin, which analogue is [A14Glu; A22Lys; B3aar$^1$; B27Pro; B28Arg; desB29; desB30] relative to human insulin; wherein aar$^1$ represents Glu (E), Gln (Q), Asp (D), Ser (S) or Thr (T).

122. An acylated analogue of human insulin, which analogue is [A14Glu; A22Lys; B3aar$^1$; B26aar$^2$; B27aar$^3$; B28aar$^4$; B29Arg; desB30] relative to human insulin; wherein aar$^1$ represents Glu (E), Gln (Q), Asp (D), Ser (S) or Thr (T); aar$^2$ represents Glu (E) or Asp (D); aar$^3$ represents Glu (E) or Asp (D); and aar$^4$ represents Glu (E) or Asp (D).

123. An acylated analogue of human insulin, which analogue is [A14Glu; A22Lys; B3aar¹; B26aar²; B27aar³; B28Arg; desB29; desB30] relative to human insulin; wherein aar¹ represents Glu (E), Gln (Q), Asp (D), Ser (S) or Thr (T); aar² represents Glu (E) or Asp (D); and aar³ represents Glu (E) or Asp (D).

124. An acylated analogue of human insulin, which analogue is [A14Glu; A22Lys; B3aar¹; B26aar²; B27Pro; B28aar⁴; B29Arg; desB30] relative to human insulin; wherein aar¹ represents Glu (E), Gln (Q), Asp (D), Ser (S) or Thr (T); aar² represents Glu (E) or Asp (D); and aar⁴ represents Glu (E) or Asp (D).

125. An acylated analogue of human insulin, which analogue is [A14Glu; A22Lys; B3aar¹; B26aar²; B27Pro; B28aar⁴; B29Pro; B30Arg] relative to human insulin; wherein aar¹ represents Glu (E), Gln (Q), Asp (D), Ser (S) or Thr (T); aar² represents Glu (E) or Asp (D); and aar⁴ represents Glu (E) or Asp (D).

126. An acylated analogue of human insulin, which analogue is [A8Arg; A14Glu; A22Lys; B3aar¹; B26aar²; B29Arg; desB30] relative to human insulin; wherein aar¹ represents Glu (E), Gln (Q), Asp (D), Ser (S) or Thr (T); and aar² represents Glu (E) or Asp (D).

127. An acylated analogue of human insulin, which analogue is [A8Arg; A14Glu; A22Lys; B3aar¹; B27aar³; B29Arg; desB30] relative to human insulin; wherein aar¹ represents Glu (E), Gln (Q), Asp (D), Ser (S) or Thr (T); and aar³ represents Glu (E) or Asp (D).

128. An acylated analogue of human insulin, which analogue is [A8Arg; A14Glu; A22Lys; B3aar¹; B27Pro; B28aar⁴; B29Pro; B30Arg] relative to human insulin; wherein aar¹ represents Glu (E), Gln (Q), Asp (D), Ser (S) or Thr (T); and aar⁴ represents Glu (E) or Asp (D).

129. An acylated analogue of human insulin, which analogue is [A8Arg; A14Glu; A22Lys; B3aar¹; B27Pro; B28aar⁴; B29Arg; desB30] relative to human insulin; wherein aar¹ represents Glu (E), Gln (Q), Asp (D), Ser (S) or Thr (T); and aar⁴ represents Glu (E) or Asp (D).

130. An acylated analogue of human insulin, which analogue is [A8Arg; A14Glu; A22Lys; B3aar¹; B27Pro; B28Arg; desB29; desB30] relative to human insulin; wherein aar¹ represents Glu (E), Gln (Q), Asp (D), Ser (S) or Thr (T).

131. An acylated analogue of human insulin, which analogue is [A8Arg; A14Glu; A22Lys; B3aar¹; B28aar⁴; B29Arg; desB30] relative to human insulin; wherein aar¹ represents Glu (E), Gln (Q), Asp (D), Ser (S) or Thr (T); and aar⁴ represents Glu (E) or Asp (D).

132. An acylated analogue of human insulin, which analogue is [A8Arg; A14Glu; A22Lys; B3aar¹; B28aar⁴; B29Pro; B30Arg] relative to human insulin; wherein aar¹ represents Glu (E), Gln (Q), Asp (D), Ser (S) or Thr (T); and aar⁴ represents Glu (E) or Asp (D).

133. An acylated analogue of human insulin, which analogue is [A8Arg; A14Glu; A22Lys; B3aar¹; B28Arg; desB29; desB30] relative to human insulin; wherein aar¹ represents Glu (E), Gln (Q), Asp (D), Ser (S) or Thr (T).

134. An acylated analogue of human insulin, which analogue is [A8Arg; A14Glu; A22Lys; B3aar¹; B26aar²; B27aar³; B29Arg; desB30] relative to human insulin; wherein aar¹ represents Glu (E), Gln (Q), Asp (D), Ser (S) or Thr (T); aar² represents Glu (E) or Asp (D); and aar³ represents Glu (E) or Asp (D).

135. An acylated analogue of human insulin, which analogue is [A8Arg; A14Glu; A22Lys; B3aar¹; B26aar²; B27Pro; B28aar⁴; B29Pro; B30Arg] relative to human insulin; wherein aar¹ represents Glu (E), Gln (Q), Asp (D), Ser (S) or Thr (T); aar² represents Glu (E) or Asp (D); and aar⁴ represents Glu (E) or Asp (D).

136. An acylated analogue of human insulin, which analogue is [A8Arg; A14Glu; A22Lys; B3aar¹; B26aar²; B27Pro; B28aar⁴; B29Arg; desB30] relative to human insulin; wherein aar¹ represents Glu (E), Gln (Q), Asp (D), Ser (S) or Thr (T); aar² represents Glu (E) or Asp (D); and aar⁴ represents Glu (E) or Asp (D).

137. An acylated analogue of human insulin, which analogue is [A8Arg; A14Glu; A22Lys; B3aar¹; B26aar²; B27Pro; B28Arg; desB29; desB30] relative to human insulin; wherein aar¹ represents Glu (E), Gln (Q), Asp (D), Ser (S) or Thr (T); and aar² represents Glu (E) or Asp (D).

138. An acylated analogue of human insulin, which analogue is [A8Arg; A14Glu; A22Lys; B3aar¹; B26aar²; B28aar⁴; B29Arg; desB30] relative to human insulin; wherein aar¹ represents Glu (E), Gln (Q), Asp (D), Ser (S) or Thr (T); aar² represents Glu (E) or Asp (D); and aar⁴ represents Glu (E) or Asp (D).

139. An acylated analogue of human insulin, which analogue is [A8Arg; A14Glu; A22Lys; B3aar¹; B26aar²; B28aar⁴; B29Pro; B30Arg] relative to human insulin; wherein aar¹ represents Glu (E), Gln (Q), Asp (D), Ser (S) or Thr (T); aar² represents Glu (E) or Asp (D); and aar⁴ represents Glu (E) or Asp (D).

140. An acylated analogue of human insulin, which analogue is [A8Arg; A14Glu; A22Lys; B3aar¹; B26aar²; B28Arg; desB29; desB30] relative to human insulin; wherein aar¹ represents Glu (E), Gln (Q), Asp (D), Ser (S) or Thr (T); and aar² represents Glu (E) or Asp (D).

141. An acylated analogue of human insulin, which analogue is [A8Arg; A14Glu; A22Lys; B3aar¹; B27aar³; B28aar⁴; B29Arg; desB30] relative to human insulin; wherein aar¹ represents Glu (E), Gln (Q), Asp (D), Ser (S) or Thr (T); aar³ represents Glu (E) or Asp (D); and aar⁴ represents Glu (E) or Asp (D).

142. An acylated analogue of human insulin, which analogue is [A8Arg; A14Glu; A22Lys; B3aar¹; B27aar³; B28aar⁴; B29Pro; B30Arg] relative to human insulin; wherein aar¹ represents Glu (E), Gln (Q), Asp (D), Ser (S) or Thr (T); aar³ represents Glu (E) or Asp (D); and aar⁴ represents Glu (E) or Asp (D).

143. An acylated analogue of human insulin, which analogue is [A8Arg; A14Glu; A22Lys; B3aar¹; B27aar³; B28Arg; desB29; desB30] relative to human insulin; wherein aar¹ represents Glu (E), Gln (Q), Asp (D), Ser (S) or Thr (T); and aar³ represents Glu (E) or Asp (D).

144. An acylated analogue of human insulin, which analogue is [A8Arg; A14Glu; A22Lys; B3aar¹; B27Pro; B28aar⁴; B29Arg; desB30] relative to human insulin; wherein aar¹ represents Glu (E), Gln (Q), Asp (D), Ser (S) or Thr (T); and aar⁴ represents Glu (E) or Asp (D).

145. An acylated analogue of human insulin, which analogue is [A8Arg; A14Glu; A22Lys; B3aar¹; B27Pro; B28aar⁴; B29Pro; B30Arg] relative to human insulin; wherein aar¹ represents Glu (E), Gln (Q), Asp (D), Ser (S) or Thr (T); and aar⁴ represents Glu (E) or Asp (D).

146. An acylated analogue of human insulin, which analogue is [A8Arg; A14Glu; A22Lys; B3aar¹; B27Pro; B28Arg; desB29; desB30] relative to human insulin; wherein aar¹ represents Glu (E), Gln (Q), Asp (D), Ser (S) or Thr (T).

147. An acylated analogue of human insulin, which analogue is [A8Arg; A14Glu; A22Lys; B3aar¹; B26aar²; B27aar³; B28aar⁴; B29Arg; desB30] relative to human insulin; wherein aar¹ represents Glu (E), Gln (Q), Asp (D), Ser (S) or Thr (T); aar² represents Glu (E) or Asp (D); aar³ represents Glu (E) or Asp (D); and aar⁴ represents Glu (E) or Asp (D).

148. An acylated analogue of human insulin, which analogue is [A8Arg; A14Glu; A22Lys; B3aar¹; B26aar²; B27aar³; B28Arg; desB29; desB30] relative to human insulin; wherein aar¹ represents Glu (E), Gln (Q), Asp (D), Ser (S) or Thr (T); aar² represents Glu (E) or Asp (D); and aar³ represents Glu (E) or Asp (D).

149. An acylated analogue of human insulin, which analogue is [A8Arg; A14Glu; A22Lys; B3aar¹; B26aar²; B27Pro; B28aar⁴; B29Arg; desB30] relative to human insulin; wherein aar¹ represents Glu (E), Gln (Q), Asp (D), Ser (S) or Thr (T); aar² represents Glu (E) or Asp (D); and aar⁴ represents Glu (E) or Asp (D).

150. An acylated analogue of human insulin, which analogue is [A8Arg; A14Glu; A22Lys; B3aar¹; B26aar²; B27Pro; B28aar⁴; B29Pro; B30Arg] relative to human insulin; wherein aar¹ represents Glu (E), Gln (Q), Asp (D), Ser (S) or Thr (T); aar² represents Glu (E) or Asp (D); and aar⁴ represents Glu (E) or Asp (D).

151. An acylated analogue of human insulin, which analogue is

[A8R, A22K, B3E, B26E, B27E, B28R, desB29, desB30];
[A8R, A22K, B3E, B26E, B27P, B28R, desB29, desB30];
[A8R, A22K, B3E, B26E, B28E, B29R, desB30];
[A8R, A22K, B3E, B26E, B29R, desB30];
[A8R, A22K, B3E, B27E, B28E, B29R, desB30];
[A8R, A22K, B3E, B27E, B28R, desB29, desB30];
[A14E, A22K, B3E, B27E, B28E, B29R, desB30];
[A14E, A22K, B3Q, B27E, B28E, B29R, desB30];
[A14E, A22K, B3Q, B28D, B29R, desB30];
[A22K, B3E, B26E, B27E, B28E, B29R, desB30];
[A22K, B3E, B26E, B27E, B28R, desB29, desB30];
[A22K, B3E, B26E, B27E, B29P, B30R];
[A22K, B3E, B26E, B27P, B28R, desB29, desB30];
[A22K, B3E, B26E, B28E, B29P, B30R];
[A22K, B3E, B26E, B28E, B29R, desB30];
[A22K, B3E, B26E, B28D, B29R, desB30];
[A22K, B3E, B26E, B29R, desB30];
[A22K, B3E, B27E, B28E, B29P, B30R];
[A22K, B3E, B27E, B28E, B29R, desB30];
[A22K, B3E, B27E, B28R, desB29, desB30];
[A22K, B3E, B27E, B29R, desB30];
[A22K, B3E, B27P, B28E, B29R, desB30];
[A22K, B3E, B28D, B29R, desB30];
[A22K, B3E, B28E, B29P, B30R];
[A22K, B3Q, B26E, B28E, B29R, desB30]; or
[A22K, B3Q, B26E, B29R, desB30];

relative to human insulin.

The insulin analogue of the invention is derivatized by acylation of the epsilon amino group of the lysine residue at the A22 position with a group of Formula II

[Acyl]-[Linker]- wherein the Linker group is an amino acid chain composed of from 1 to 10 amino acid residues selected from gGlu and/or OEG; wherein gGlu represents a gamma glutamic acid residue;
OEG represents a residue of 8-amino-3,6-dioxaoctanoic acid (i.e. a group of the formula —NH—(CH₂)₂—O—(CH₂)₂—O—CH₂—CO—);
which amino acid residues may be present in any order; and
which amino acid chain comprises at least one gGlu residue; and wherein the Acyl group is a residue of an α,ω-di-carboxylic acid selected from 1,14-tetradecanedioic acid; 1,15-pentadecanedioic acid; and 1,16-hexadecanedioic acid.

152. An acylated analogue of human insulin, wherein the Linker group is an amino acid chain composed of from 1 to 10 amino acid residues selected from gGlu and/or OEG.

153. An acylated analogue of human insulin, wherein the Linker group is an amino acid chain composed of from 1 to 6 amino acid residues.

154. An acylated analogue of human insulin, wherein the Linker group is an amino acid chain composed of from 1 to 5 amino acid residues.

155. An acylated analogue of human insulin, wherein the Linker group is an amino acid chain composed of from 1 to 4 amino acid residues.

156. An acylated analogue of human insulin, wherein the Linker group is an amino acid chain composed of from 2 to 6 amino acid residues.

157. An acylated analogue of human insulin, wherein the Linker group is an amino acid chain composed of 2, 3, 4 or 5 amino acid residues.

158. An acylated analogue of human insulin, wherein the Linker group is an amino acid chain composed of 3 or 4 amino acid residues.

159. An acylated analogue of human insulin, wherein acylated insulin analogue of the invention comprises at least one gGlu residue.

160. An acylated analogue of human insulin, wherein the acylated insulin analogue of the invention comprises of from 1 to 10 gGlu residues.

161. An acylated analogue of human insulin, wherein the acylated insulin analogue of the invention comprises of from 1 to 8 gGlu residues.

162. An acylated analogue of human insulin, wherein the acylated insulin analogue of the invention comprises of from 1 to 6 gGlu residues.

163. An acylated analogue of human insulin, wherein the acylated insulin analogue of the invention comprises of from 1, 2, 3, 4 or 5 gGlu residues.

164. An acylated analogue of human insulin, wherein the Acyl group of acylated insulin analogue of the invention is a residue of an α,ω-di-carboxylic acid selected from 1,14-tetradecanedioic acid; 1,15-pentadecanedioic acid; and 1,16-hexadecanedioic acid.

165. An acylated analogue of human insulin, wherein the Acyl group of acylated insulin analogue of the invention is a residue of 1,14-tetradecanedioic acid.

166. An acylated analogue of human insulin, wherein the Acyl group of acylated insulin analogue of the invention is a residue of 1,15-pentadecanedioic acid.

167. An acylated analogue of human insulin, wherein the Acyl group of acylated insulin analogue of the invention is a residue of 1,16-hexadecanedioic acid.

168. An acylated analogue of human insulin, wherein the group of Formula II is
tetradecanedioyl-4×gGlu;
tetradecanedioyl-gGlu-2×OEG;
hexadecanedioyl-4×gGlu;
hexadecanedioyl-4×gGlu-2×OEG;
hexadecanedioyl-gGlu-2×OEG;
hexadecanedioyl-gGlu-4×OEG; or
hexadecanedioyl-gGlu-6×OEG.

169. An acylated analogue of human insulin, wherein the group of Formula II is
tetradecanedioyl-4×gGlu;
tetradecanedioyl-gGlu-2×OEG;
hexadecanedioyl-4×gGlu; or
hexadecanedioyl-gGlu-2×OEG.

170. An acylated analogue of human insulin, wherein the group of Formula II is tetradecanedioyl-4×gGlu.

171. An acylated analogue of human insulin, wherein the group of Formula II is tetradecanedioyl-gGlu-2×OEG.

172. An acylated analogue of human insulin, wherein the group of Formula II is hexadecanedioyl-4×gGlu.

173. An acylated analogue of human insulin, wherein the group of Formula II is hexadecanedioyl-4×gGlu-2×OEG.

174. An acylated analogue of human insulin, wherein the group of Formula II is hexadecanedioyl-gGlu-2×OEG.

175. An acylated analogue of human insulin, wherein the group of Formula II is hexadecanedioyl-gGlu-4×OEG.

176. An acylated analogue of human insulin, wherein the group of Formula II is hexadecanedioyl-gGlu-6×OEG.

177. An acylated analogue of human insulin, which is
A22K(N(eps)tetradecanedioyl-gGlu-2×OEG), B3E, B27E, B28E, B29R, desB30 human insulin;
A14E, A22K(N(eps)tetradecanedioyl-gGlu-2×OEG), B3E, B27E, B28E, B29R, desB30 human insulin;
A22K(N(eps)tetradecanedioyl-4×gGlu), B3E, B27E, B28E, B29R, desB30 human insulin;
A14E, A22K(N(eps)tetradecanedioyl-4×gGlu), B3E, B27E, B28E, B29R, desB30 human insulin;
A22K(N(eps)tetradecanedioyl-gGlu-2×OEG), B3E, B27P, B28E, B29R, desB30 human insulin;
A22K(N(eps)tetradecanedioyl-4×gGlu), B3E, B27E, B29R, desB30 human insulin;
A22K(N(eps)tetradecanedioyl-gGlu-2×OEG), B3E, B28D, B29R, desB30 human insulin;
A14E, A22K(N(eps)tetradecanedioyl-4×gGlu), B3Q, B28D, B29R, desB30 human insulin;
A14E, A22K(N(eps)tetradecanedioyl-4×gGlu), B3Q, B27E, B28E, B29R, desB30 human insulin;
A22K(N(eps)tetradecanedioyl-4×gGlu), B3E, B28D, B29R, desB30 human insulin;
A22K(N(eps)tetradecanedioyl-4×gGlu), B3E, B26E, B28E, B29R, desB30 human insulin;
A22K(N(eps)tetradecanedioyl-4×gGlu), B3E, B26E, B29R, desB30 human insulin;
A22K(N(eps)tetradecanedioyl-4×gGlu), B3E, B26E, B27P, B28R, desB29, desB30 human insulin;
A22K(N(eps)tetradecanedioyl-4×gGlu), B3E, B27E, B28R, desB29, desB30 human insulin;
A8R, A22K(N(eps)tetradecanedioyl-4×gGlu), B3E, B26E, B29R, desB30 human insulin;
A8R, A22K(N(eps)tetradecanedioyl-4×gGlu), B3E, B26E, B27P, B28R, desB29, desB30 human insulin;
A8R, A22K(N(eps)tetradecanedioyl-4×gGlu), B3E, B27E, B28R, desB29, desB30 human insulin;
A22K(N(eps)tetradecanedioyl-4×gGlu), B3E, B26E, B27E, B28R, desB29, desB30 human insulin;
A8R, A22K(N(eps)tetradecanedioyl-4×gGlu), B3E, B26E, B27E, B28R, desB29, desB30 human insulin;
A22K(N(eps)tetradecanedioyl-4×gGlu), B3E, B28E, B29P, B30R human insulin;
A22K(N(eps)tetradecanedioyl-4×gGlu), B3E, B26E, B28E, B29P, B30R human insulin;
A22K(N(eps)tetradecanedioyl-4×gGlu), B3E, B27E, B28E, B29P, B30R human insulin;
A8R, A22K(N(eps)tetradecanedioyl-4×gGlu), B3E, B26E, B28E, B29R, desB30 human insulin;
A8R, A22K(N(eps)tetradecanedioyl-4×gGlu), B3E, B27E, B28E, B29R, desB30 human insulin;
A22K(N(eps)Hexadecanedioyl-gGlu-2×OEG), B3E, B27E, B29R, desB30 human insulin;
A14E, A22K(N(eps)hexadecanedioyl-gGlu-2×OEG), B3E, B27E, B28E, B29R, desB30 human insulin;
A14E, A22K(N(eps)hexadecanedioyl-4×gGlu), B3E, B27E, B28E, B29R, desB30 human insulin;
A22K(N(eps)hexadecanedioyl-4×gGlu), B3E, B27E, B28E, B29R, desB30 human insulin;
A22K(N(eps)hexadecanedioyl-gGlu-2×OEG), B3E, B27P, B28E, B29R, desB30 human insulin;
A22K(N(eps)hexadecanedioyl-4×gGlu), B3E, B27P, B28E, B29R, desB30 human insulin;
A22K(N(eps)hexadecanedioyl-gGlu-2×OEG), B3E, B27E, B28E, B29R, desB30 human insulin;
A22K(N(eps)hexadecanedioyl-4×gGlu), B3E, B27E, B29R, desB30 human insulin;
A22K(N(eps)hexadecanedioyl-gGlu-2×OEG), B3E, B28D, B29R, desB30 human insulin;
A22K(N(eps)tetradecanedioyl-4×gGlu), B3E, B26E, B28D, B29R, desB30 human insulin;
A22K(N(eps)tetradecanedioyl-4×gGlu), B3E, B26E, B27E, B29P, B30R human insulin;
A22K(N(eps)tetradecanedioyl-4×gGlu), B3E, B26E, B27E, B28E, B29R, desB30 human insulin;
A22K(N(eps)hexadecanedioyl-4×gGlu), B3E, B28D, B29R, desB30 human insulin;
A22K(N(eps)tetradecanedioyl-4×gGlu), B3E, B27P, B28E, B29R, desB30 human insulin;
A22K(N(eps)tetradecanedioyl-4×gGlu), B3Q, B26E, B29R, desB30 human insulin;
A22K(N(eps)tetradecanedioyl-4×gGlu), B3Q, B26E, B28E, B29R, desB30 human insulin;
A22K(N(eps)hexadecanedioyl-4×gGlu), B3E, B26E, B29R, desB30 human insulin;
A22K(N(eps)hexadecanedioyl-gGlu-2×OEG), B3E, B26E, B29R, desB30 human insulin;
A22K(N(eps)hexadecanedioyl-gGlu-4×OEG), B3E, B26E, B29R, desB30 human insulin;
A22K(N(eps)hexadecanedioyl-gGlu-6×OEG), B3E, B26E, B29R, desB30 human insulin;
A22K(N(eps)hexadecanedioyl-4×gGlu-2×OEG), B3E, B26E, B29R, desB30 human insulin; or
A22K(N(eps)hexadecanedioyl-4×gGlu), B3Q, B26E, B29R, desB30 human insulin.

Any combination of two or more of the embodiments described herein is considered within the scope of the present invention.

Definitions

Nomenclature

Herein, the naming of the insulins is done according to the following principles:

The term "analogue" is frequently used for the insulin protein or peptide in question before it undergoes further chemical modification (derivatisation), and in particular acylation. The product resulting from such a chemical modification (derivatisation) is usually called a "derivative" or "acylated analogue". However, in the context of this application, the term "analogue" designates analogues of human insulin as well as (the acylated) derivatives of such human insulin analogues.

The names are given as analogues, derivatives and modifications (acylations) relative to human insulin. For the naming of the acyl moiety (i.e. the [Acyl]-[Linker]- group of formula II), in some instances the naming is done according to IUPAC nomenclature, and in other instances the naming is done as peptide nomenclature.

As an example, the acyl moiety of the following structure (Chem. 1):

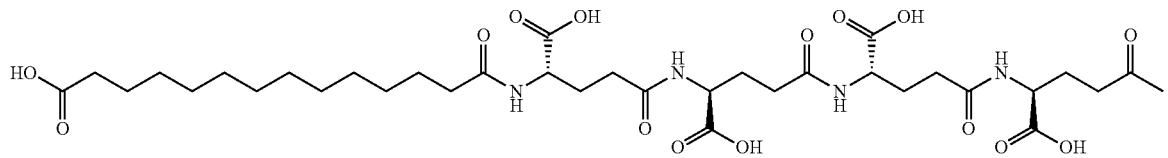 [SMILES: CC(=O)CC[C@H](NC(=O)CC[C@H](NC(=O)CC[C@H](NC(=O)CC[C@H](NC(=O)CCCCCCCCCCCCC(=O)O)C(=O)O)C(=O)O)C(=O)O)C(=O)O]

may be named "tetradecanedioyl-4×gGlu", "tetradecanedioyl-4×γGlu" or, "1,14-tetradecanedioyl-4×gGlu" or the like, wherein γGlu (and gGlu) is short hand notation for the amino acid gamma glutamic acid in the L-configuration, and "4×" means that the residue following is repeated 4 times.

Similarly, the acyl moiety of the following structure (Chem. 2):

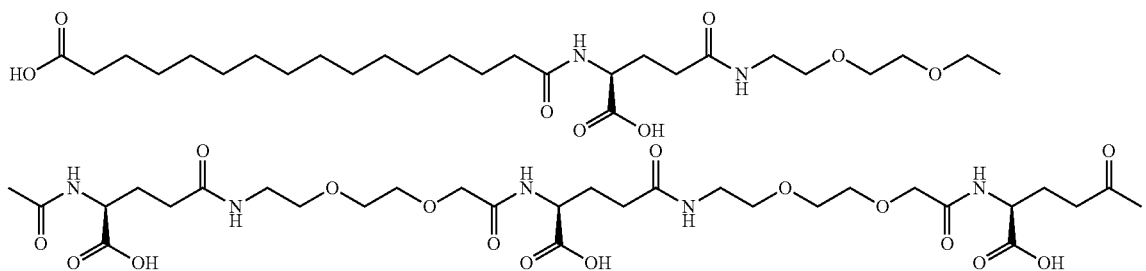

can for example be named "hexadecanedioyl-(gGlu-OEG)₃-gGlu)", "hexadecanedioyl-(gGlu-OEG)₃-gGlu)", "hexadecanedioyl-3×(gGlu-OEG)-gGlu)", "1,16-hexadecanedioyl-(gGlu-OEG)₃-gGlu)", "1,16-hexadecanedioyl-(gGlu-OEG)₃-gGlu)", "1,16-hexadecanedioyl-3×(gGlu-OEG)-gGlu)", "hexadecanedioyl-(γGlu-OEG)₃-γGlu)", "hexadecanedioyl-(γGlu-OEG)₃-γGlu)", or "hexadecanedioyl-3×(γGlu-OEG)-γGlu)";

wherein the moiety of the following structure (Chem. 3):

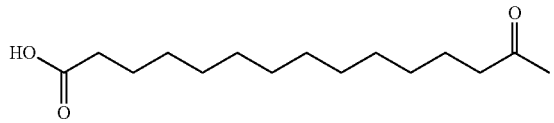 [SMILES: CC(=O)CCCCCCCCCCCCC(=O)O]

can for example be named tetradecanedioyl, 1,14-tetradecanedioyl or (short hand notation) C14 diacid. Similar notations apply for similar residues with 15 and 16 carbon atoms, pentadecanedioyl, C15 diacid, and hexadecanedioyl, C16 diacid, respectively.

γGlu (and gGlu) is short hand notation for the amino acid gamma glutamic acid, $H_2N-CH(CO_2H)-CH_2CH_2-CO_2H$ (connected via the alpha amino group and via the gamma (side chain) carboxy group), in the L-configuration.

OEG is short hand notation for the amino acid residue 8-amino-3,6-dioxaoctanoic acid, $NH_2(CH_2)_2O(CH_2)_2OCH_2CO_2H$.

"2×" and "3×" means that the residues following is repeated 2, respectively, 3 times.

For example, the insulin derivative of Example 1 is named "A22K(N(eps)tetra-decanedioyl-gGlu-2×OEG), B3E, B27E, B28E, B29R, desB30 human insulin" to indicate that the A-chain, that contains 21 amino acid residues in human insulin, has been extended by 1 amino acid (position A22), with a lysine (K), that further is modified by acylation on the epsilon nitrogen in the lysine residue of A22, denoted $N^\varepsilon$ (or N(eps)) by the moiety tetradecanedioyl-gGlu-2×OEG, the amino acid in position B3, N in human insulin, has been substituted with E (glutamic acid), the amino acid in position B27, T in human insulin, has been substituted with E (glutamic acid), the amino acid in position B28, P in human insulin, has been substituted with E, glutamic acid, the amino acid in position B29, K in human insulin, has been substituted with R, arginine, the amino acid in position B30, threonine, T, in human insulin, has been deleted. Asterisks in the formulae below indicate that the residue in question is different (i.e. substituted) as compared to human insulin.

Throughout this application, both formulas and names of preferred insulins of the invention are given.

In addition, the insulins of the invention are also named according to IUPAC nomenclature (OpenEye, IUPAC style). According to this nomenclature, the insulin derivative of Example 1 is assigned the following name: N{Alpha}([Glu B3,GluB27,GluB28,ArgB29],des-ThrB30-Insulin(human)-(A)-peptidyl)-N{Epsilon}[2-[2-[2-[[2-[2-[2-[[(4S)-4-carboxy-4-(13-carboxytridecanoylamino)-butanoyl]amino]ethoxy]ethoxy]acetyl]amino]ethoxy]ethoxy]acetyl]Lys,(B)-peptide.

It should be noted that formulas can be written with the lysine residue (that is modified by acylation) either is drawn with the lysine residue expanded (as shown e.g. in Example 8) or drawn with the lysine residue contracted (as shown e.g. in Example 1). In all cases the acyl group is attached to the epsilon nitrogen of the lysine residue.

Physical Stability

The term "physical stability" of the insulin preparation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein preparations is evaluated by means of visual inspection and/or turbidity measurements after exposing the preparation filled in suitable containers (e.g. cartridges or vials) to mechanical/physical stress (e.g. agitation) at different temperatures for various time periods. Visual inspection of the preparations is performed in a sharp focused light with a dark background. A preparation is classified physically unstable with respect to protein aggregation, when it shows visual turbidity in daylight. Alternatively, the turbidity of the preparation can be evaluated by simple turbidity measurements well-known to the skilled person. Physical stability of the aqueous protein preparations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Chemical Stability

The term "chemical stability" of the protein preparation as used herein refers to changes in the covalent protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Increasing amounts of chemical degradation products are often seen during storage and use of the protein preparation. Most proteins are prone to deamidation, a process in which the side chain amide group in glutaminyl or asparaginyl residues is hydrolysed to form a free carboxylic acid or asparaginyl residues to form an isoAsp derivative. Other degradations pathways involves formation of high molecular weight products where two or more protein molecules are covalently bound to each other through transamidation and/or disulfide interactions leading to formation of covalently bound dimer, oligomer and polymer degradation products (Stability of Protein Pharmaceuticals, Ahern T J & Manning M G, Plenum Press, New York 1992). Oxidation (of for instance methionine residues) can be mentioned as another variant of chemical degradation. The chemical stability of the protein preparation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size, hydrofobicity, and/or charge using various chromatography techniques (e.g. SEC-HPLC and/or RP-HPLC). Since HMWP products are potentially immunogenic and not biologically active, low levels of HMWP are advantageous.

Methods of Synthesis

The insulin derivatives of the invention may be obtained by conventional methods for the preparation of insulin, insulin analogues and insulin derivatives, and in particular the methods described in the working examples.

Biological Activity

In another aspect the invention provides novel insulin derivatives for use as medicaments, or for use in the manufacture of medicaments or pharmaceutical compositions.

The insulin derivatives of the invention are found to be short and fast acting insulin derivatives that are considered well suited for prandial use.

The insulin derivatives of the invention all possess insulin receptor affinities adequate for activating the insulin receptor in order to give the glycaemic response needed, i.e. being able to lower blood glucose in animals and humans. As a measure of functional (agonistic) activity of the insulins of the invention, lipogenesis activity in primary rat adipocytes are demonstrated.

The insulin derivatives of the invention are found to have a balanced insulin receptor (IR) to insulin-like growth factor 1 receptor (IGF-1R) affinity ratio (IR/IGF-1R).

In one aspect, the A22K acylated insulin of the invention has an IR/IGF-1R ratio of above 0.3; of above 0.4; of above 0.5; of above 0.6; of above 0.7; of above 0.8; of above 0.9; of above 1; of above 1.5; or of above 2.

In another aspect, the A22K acylated insulin analogue is a compound of the invention, wherein the Acyl group of Formula II is derived from 1,14-tetradecanedioic acid, and which acylated insulin analogue has a mean residence time (MRT) of less than 250 minutes; of less than 200 minutes; of less than 175 minutes; of less than 150 minutes; of less than 125 minutes; of less than 100 minutes; following subcutaneous injection of a 600 µM (approx.) formulation of the acylated insulin analogue of the invention, containing 1.6% (w/vol, approx.) glycerol and 30 mM phenol/m-cresol, pH 7.4, to pigs.

In another aspect, the A22K acylated insulin analogue is a compound of the invention, wherein the Acyl group of Formula II is derived from 1,16-hexadecanedioic acid, and which acylated insulin analogue has a mean residence time (MRT) of less than 700 minutes; of less than 600 minutes; of less than 500 minutes; of less than 400 minutes; of less than 300 minutes; of less than 250 minutes; following subcutaneous injection of a 600 µM (approx.) formulation of the acylated insulin analogue of the invention, containing 1.6% (w/vol, approx.) glycerol and 30 mM phenol/m-cresol, pH 7.4, to pigs.

In a further aspect, the invention relates to the medical use of the acylated insulin analogue of the invention, and in particular to the use of such insulin derivatives for the treatment, prevention or alleviation of diseases, disorders or conditions relating to diabetes, Type 1 diabetes, Type 2 diabetes, impaired glucose tolerance, hyperglycemia, dyslipidemia, obesity, metabolic syndrome (metabolic syndrome X, insulin resistance syndrome), hypertension, cognitive disorders, atherosclerosis, myocardial infarction, stroke, cardiovascular disorders, coronary heart disease, inflammatory bowel syndrome, dyspepsia, or gastric ulcers, which method comprises administration to a subject in need thereof a therapeutically effective amount of the insulin derivative of the invention.

In another embodiment, the invention relates to the use of such insulin derivatives for the treatment, prevention or alleviation of diseases, disorders or conditions relating to diabetes, Type 1 diabetes, Type 2 diabetes, or impaired glucose tolerance, which method comprises administration to a subject in need thereof a therapeutically effective amount of the insulin derivative of the invention.

In a third embodiment, the invention relates to the use of such insulin derivatives for the treatment, prevention or alleviation of diseases, disorders or conditions relating to diabetes, and in particular Type 1 diabetes or Type 2 diabetes.

Pharmaceutical Compositions

The present invention relates to acylated insulin analogues useful as medicaments, or for the manufacture of a pharmaceutical composition/medicament.

Therefore, in another aspect, the invention provides novel pharmaceutical compositions comprising a therapeutically effective amount of an insulin derivative according to the present invention.

The pharmaceutical composition according to the invention optionally comprises one or more pharmaceutically acceptable carriers and/or diluents.

The pharmaceutical composition of the present invention may further comprise other excipients commonly used in pharmaceutical compositions e.g. preservatives, chelating agents, tonicity agents, absorption enhancers, stabilizers, antioxidants, polymers, surfactants, metal ions, oleaginous vehicles and proteins (e.g., human serum albumin, gelatine or proteins).

In one embodiment of the invention the pharmaceutical composition of the invention is an aqueous preparation, i.e. preparation comprising water. Such preparation is typically a solution or a suspension. In a further embodiment of the invention the pharmaceutical composition is an aqueous solution.

The term "aqueous preparation" is defined as a preparation comprising at least 50% w/w water. Likewise, the term "aqueous solution" is defined as a solution comprising at least 50% w/w water, and the term "aqueous suspension" is defined as a suspension comprising at least 50% w/w water. Aqueous suspensions may contain the active compounds in admixture with excipients suitable for the manufacture of aqueous suspensions.

In one embodiment of the invention the insulin preparation comprises an aqueous solution of an insulin derivative of the present invention, wherein said insulin compound is present in a concentration from about 0.1 mM to about 20.0 mM; more particularly of from about 0.2 mM to about 4.0 mM; of from about 0.3 mM to about 2.5 mM; of from about 0.5 mM to about 2.5 mM; of from about 0.6 mM to about 2.0 mM; or of from about 0.6 mM to about 1.2 mM.

In another embodiment of the invention the insulin preparation comprises an aqueous solution of an insulin derivative of the present invention, wherein said insulin compound is present in a concentration of about 0.1 mM, of about 0.3 mM, of about 0.4 mM, of about 0.6 mM, of about 0.9 mM, of about 1.2 mM, of about 1.5 mM, or of about 1.8 mM The pharmaceutical composition of the present invention may further comprise a buffer system. The buffer may be selected from the group consisting of, but not limited to, sodium acetate, sodium carbonate, sodium dihydrogen phosphate, disodium hydrogen phosphate, sodium phosphate, and tris(hydroxymethyl)-aminomethan, bicine, tricine, malic acid, glycyl-glycine, ethylene diamine, succinic acid, maleic acid, fumaric acid, tartaric acid, aspartic acid or mixtures thereof. Each one of these specific buffers constitutes an alternative embodiment of the invention.

In one embodiment the buffer is a phosphate buffer. In yet another embodiment, the concentration of said phosphate buffer is in the range from about 0.1 mM to 20 mM, In yet another embodiment the concentration of said phosphate buffer is in the range from 0.1 mM to about 10 mM, or from about 0.1 mM to about 8 mM, from about 1 mM to about 8 mM, or from about 2 mM to about 8 mM, or from 6 mM to 8 mM.

The pH of the injectable pharmaceutical composition of the invention is in the range of from 3 to 8.5. Preferably, the injectable pharmaceutical composition according to the invention has a pH in the range from about 6.8 to about 7.8.

In one embodiment the pH is in the range from about 7.0 to about 7.8, or from 7.2 to 7.6.

The insulin preparations of the present invention may further comprise a tonicity agent. The tonicity agent may be selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. Each one of these specific tonicity agents or mixtures hereof constitutes an alternative embodiment of the invention.

In a one embodiment of the invention, glycerol and/or mannitol and/or sodium chloride may be present in an amount corresponding to a concentration of from 0 to 250 mM, from 0 to 200 mM, or from 0 to 100 mM.

The insulin preparations of the present invention may further comprise a pharmaceutically acceptable preservative. The preservative may be present in an amount sufficient to obtain a preserving effect. The amount of preservative in a pharmaceutical composition of the invention may be determined from e.g. literature in the field and/or the known amount(s) of preservative in e.g. commercial products. Each one of these specific preservatives or mixtures hereof constitutes an alternative embodiment of the invention. The use of a preservative in pharmaceutical preparations is described, for example in Remington: *The Science and Practice of Pharmacy,* $19^{th}$ edition, 1995.

In one embodiment, the injectable pharmaceutical composition comprises at least one phenolic compound as preservative agent.

In another embodiment the phenolic compound for use according to the invention may be present in up to about 6 mg/mL of final injectable pharmaceutical composition, in particular of up to about 4 mg/mL of final injectable pharmaceutical composition.

In another embodiment the phenolic compound for use according to the invention may be present in an amount of up to about 4.0 mg/mL of final injectable pharmaceutical composition; in particular of from about 0.5 mg/mL to about 4.0 mg/mL; or of from about 0.6 mg/mL to about 4.0 mg/mL.

In another embodiment the preservative is phenol.

In another embodiment, the injectable pharmaceutical composition comprises a mixture of phenol and m-cresol as preservative agent.

In another embodiment, the injectable pharmaceutical composition comprises about 16 mM phenol (1.5 mg/mL) and about 16 mM m-cresol (1.72 mg/mL).

The pharmaceutical composition of the present invention may further comprise a chelating agent. The use of a chelating agent in pharmaceutical preparations is well-known to the skilled person. For convenience reference is made to Remington: *The Science and Practice of Pharmacy*, 19$^{th}$ edition, 1995.

The pharmaceutical composition of the present invention may further comprise a absorption enhancer. The group of absorption enhancers may include but is not limited to nicotinic compounds. The term nicotinic compound includes nicotinamide, nicotinic acid, niacin, niacin amide and vitamin B3 and/or salts thereof and/or any combination thereof.

In one embodiment, the nicotinic compound is nicotinamide, and/or nicotinic acid, and/or a salt thereof. In another embodiment the nicotinic compound is nicotinamide. The nicotinic compound for use according to the invention may in particular be N-methyl nicotinamide, N,N-diethylnicotinamide, N-ethylnicotinamide, N,N-dimethylnicotinamide, N-propyl nicotinamide or N-butyl nicotinamide.

In another embodiment, the nicotinic compound is present in the amount of from about 5 mM to about 200 mM; in particular in the amount of from about 20 mM to about 200 mM; in the amount of from about 100 mM to about 170 mM; or in the amount of from about 130 mM to about 170 mM, such as about 130 mM, about 140 mM, about 150 mM, about 160 mM or about 170 mM.

The pharmaceutical composition of the present invention may further comprise a stabilizer. The term "stabilizer" as used herein refers to chemicals added to polypeptide containing pharmaceutical preparations in order to stabilize the peptide, i.e. to increase the shelf life and/or in-use time of such preparations. For convenience reference is made to Remington: *The Science and Practice of Pharmacy*, 19$^{th}$ edition, 1995.

The pharmaceutical composition of the invention may further comprise an amount of an amino acid base sufficient to decrease aggregate formation by the polypeptide or protein during storage of the composition. The term "amino acid base" refers to an amino acid or a combination of amino acids, where any given amino acid is present either in its free base form or in its salt form. The amino acids may in particular be arginine, lysine, aspartic acid, glutamic acid, aminoguanidine, ornithine or N-monoethyl L-arginine, ethionine or buthionine, or S-methyl-L cysteine. In one embodiment of the invention the amino acid base may be present in an amount corresponding to a concentration of from 1 to 100 mM; of from 1 to 50 mM; or of from 1 to 30 mM.

In one embodiment, the pharmaceutical composition of the present invention may further comprise a surfactant. The term "surfactant" as used herein refers to any molecules or ions that are comprised of a water-soluble (hydrophilic) part, the head, and a fat-soluble (lipophilic) segment. Surfactants accumulate preferably at interfaces, which the hydrophilic part is orientated towards the water (hydrophilic phase) and the lipophilic part towards the oil- or hydrophobic phase (i.e. glass, air, oil etc.). The concentration at which surfactants begin to form micelles is known as the critical micelle concentration or CMC. Furthermore, surfactants lower the surface tension of a liquid. Surfactants are also known as amphipathic compounds. The use of a surfactant in pharmaceutical preparations is well-known to the skilled person. For convenience reference is made to Remington: *The Science and Practice of Pharmacy*, 19$^{th}$ edition, 1995.

The invention further relates to a method for the preparation of such insulin preparations. The insulin preparations of this invention can be prepared by using any of a number of recognized methods. For example, the preparations can be prepared by mixing an aqueous solution of excipients with an aqueous solution of the insulin derivative, after which the pH is adjusted to a desired level and the mixture is made up to the final volume with water followed by sterile filtration.

Zinc-Free Pharmaceutical Compositions

Insulin preparations traditionally comprise zinc added as e.g. the chloride or acetate salt to obtain an acceptable stability of the pharmaceutical preparation. However, it has surprisingly been found that the insulin derivatives of the invention, while maintaining a sufficient chemical and physical stability, may be formulated into pharmaceutical compositions without the addition of zinc, thereby giving a faster onset of action than comparable insulin analogues that need $Zn^{2+}$ ions for maintaining sufficient chemical and physical stability. The zinc-free formulations are faster absorbed from the subcutaneous tissue, and thus allowing for prandial use.

In this respect it needs mentioning, that a zinc-free insulin pharmaceutical composition is indeed difficult to obtain, as traces of zinc, to a more or less extent, may be present in the excipients conventionally used for the manufacture of pharmaceutical compositions, and in particular in the rubber materials used in medical containers.

Therefore, in one aspect, the invention provides pharmaceutical compositions comprising an insulin derivative of the invention, formulated as a low-zinc composition, with no added zinc ions. Such pharmaceutical compositions are usually referred to as "zinc-free compositions", although they may in fact be considered "low-zinc compositions".

However, provided zinc-free excipients can be provided, the insulin derivatives of the present invention in fact allows for the preparation of zinc-free pharmaceutical compositions. Therefore, in another aspect, the invention provides zinc-free pharmaceutical compositions comprising an insulin derivative of the invention, and one or more pharmaceutically acceptable carriers or diluents, devoid of any zinc.

We have moreover discovered that the A22K acylated insulin derivatives of the invention, holding a substitution in position B3, that adds to both the chemical and physical stability of pharmaceutical compositions formulated without addition of zinc-ions and with no added surfactants. Therefore, in a further aspect, the invention provides a low-zinc or zinc-free pharmaceutical composition as described above, comprising an insulin derivative of the invention comprising an additional substitution in position B3 (i.e. B3E or B3Q), and one or more pharmaceutically acceptable carriers or diluents, in which pharmaceutical composition, however, no surfactant has been added.

In one embodiment, the invention provides a low-zinc pharmaceutical composition as described above, wherein the zinc ions may be present in an amount corresponding to a concentration of less than 0.2 $Zn^{2+}$ ions per 6 insulin molecules; of less than 0.15 $Zn^{2+}$ ions per 6 insulin molecules; of less than 0.12 $Zn^{2+}$ ions per 6 insulin molecules; 0.1 $Zn^{2+}$ ions per 6 insulin molecules; of less than 0.09 $Zn^{2+}$ ions per 6 insulin molecules; of less than 0.08 $Zn^{2+}$ ions per 6 insulin molecules; of less than 0.07 $Zn^{2+}$ ions per 6 insulin molecules; of less than 0.06 $Zn^{2+}$ ions per 6 insulin molecules; of less than 0.05 $Zn^{2+}$ ions per 6 insulin molecules; of less than 0.04 $Zn^{2+}$ ions per 6 insulin molecules; of less than 0.03 $Zn^{2+}$ ions per 6 insulin molecules; of less than 0.02 $Zn^{2+}$ ions per 6 insulin molecules; or of less than 0.01 $Zn^2$ ions per 6 insulin molecules.

In another embodiment, the invention provides a pharmaceutical composition formulated as a low-zinc composition, with no added zinc ions, comprising an insulin derivative and one or more pharmaceutically acceptable carriers or diluents.

In a further embodiment, the invention provides a pharmaceutical composition formulated as a low-zinc composition as described above, and wherein no surfactant has been added.

In an even further embodiment, the invention provides a pharmaceutical composition formulated as a low-zinc composition as described above, and wherein no surfactant has been added, and comprising a nicotinic compound, and in particular nicotinamide, as described above.

Methods of Administration

The pharmaceutical composition of the invention may be administered by conventional methods.

Parenteral administration may be performed by subcutaneous, intramuscular, intraperitoneal or intravenous injection by means of a syringe, optionally a pen-like syringe. Alternatively, parenteral administration can be performed by means of an infusion pump. As a further option, the insulin preparations containing the insulin compound of the invention can also be adapted to transdermal administration, e.g. by needle-free injection or from a microneedle patch, optionally an iontophoretic patch, or transmucosal, e.g. buccal, administration.

The pharmaceutical composition of the invention may be administered to a patient in need of such treatment at several sites, e.g. at topical sites, skin or mucosal sites, at sites which bypass absorption such as administration in an artery, in a vein, or in the heart, and at sites which involve absorption, e.g. administration in the skin, under the skin, in a muscle or in the abdomen.

The pharmaceutical composition of the invention may be used in the treatment of diabetes by parenteral administration. The actual dosage depends on the nature and severity of the disease being treated, and is within the discretion of the physician, and may be varied by titration of the dosage to the particular circumstances of this invention to produce the desired therapeutic effect.

However, it is currently contemplated that the insulin derivative according to the invention shall be present in the final pharmaceutical composition in an amount of from about 0.1 mM to about 20.0 mM; more particularly of from about 0.2 mM to about 4.0 mM; of from about 0.3 mM to about 2.5 mM; of from about 0.5 mM to about 2.5 mM; of from about 0.6 mM to about 2.0 mM; or of from about 0.6 mM to about 1.2 mM.

The pharmaceutical compositions of the invention may also be prepared for use in various medical devices normally used for the administration of insulin, including pen-like devices used for insulin therapy by injection, continuous subcutaneous insulin infusion therapy by use of pumps, and/or for application in basal insulin therapy.

In one embodiment the pharmaceutical composition of the invention is formulated into a pen-like device for use for insulin therapy by injection.

In another embodiment the pharmaceutical composition of the invention is formulated into an external pump for insulin administration.

Methods of Therapy

The present invention relates to drugs for therapeutic use. More specifically the invention relates to the use of the acylated derivatives of human insulin analogues of the invention for the treatment or prevention of medical conditions relating to diabetes.

Therefore, in another aspect, the invention provides a method for the treatment or alleviation of a disease or disorder or condition of a living animal body, including a human, which disease, disorder or condition may be selected from a disease, disorder or condition relating to diabetes, Type 1 diabetes, Type 2 diabetes, impaired glucose tolerance, hyperglycemia, dyslipidemia, obesity, metabolic syndrome (metabolic syndrome X, insulin resistance syndrome), hypertension, cognitive disorders, atherosclerosis, myocardial infarction, stroke, cardiovascular disorders, coronary heart disease, inflammatory bowel syndrome, dyspepsia, or gastric ulcers, which method comprises the step of administering to a subject in need thereof a therapeutically effective amount of the acylated analogue of human insulin of the invention.

In another embodiment the invention provides a method for the treatment or alleviation of a disease or disorder or condition of a living animal body, including a human, which disease, disorder or condition may be selected from a disease, disorder or condition relating to diabetes, Type 1 diabetes, Type 2 diabetes, impaired glucose tolerance, hyperglycemia, dyslipidemia, obesity, metabolic syndrome (metabolic syndrome X, insulin resistance syndrome), hypertension, cognitive disorders, atherosclerosis, myocardial infarction, stroke, cardiovascular disorders, coronary heart disease, inflammatory bowel syndrome, dyspepsia, or gastric ulcers, which method comprises administration to a subject in need thereof a therapeutically effective amount of the acylated analogue of human insulin of the invention.

In a third embodiment the invention provides a method for the treatment or alleviation of a disease or disorder or condition of a living animal body, including a human, which disease, disorder or condition may be selected from a disease, disorder or condition relating to diabetes, Type 1 diabetes, Type 2 diabetes, impaired glucose tolerance, hyperglycemia, dyslipidemia, obesity, or metabolic syndrome (metabolic syndrome X, insulin resistance syndrome).

In a fourth embodiment the invention provides a method for the treatment or alleviation of a disease or disorder or condition of a living animal body, including a human, which disease, disorder or condition may be selected from a disease, disorder or condition relating to diabetes, in particular Type 1 diabetes, or Type 2 diabetes.

BRIEF DESCRIPTION OF THE DRAWINGS

The present invention is further illustrated by reference to the accompanying drawing, in which:

FIGS. 2D1 (0-180 minutes), 2D2 (0-30 minutes), 2E1 (0-180 minutes) and 2E2 (0-30 minutes) show PD profiles (resulting from PK profiles shown in FIGS. 2A and 2B) of C14 diacid based analogues of the invention and of C14 diacid based analogues of the prior art following subcutaneous injection to Sprague Dawley rats;

FIGS. 2F1 (0-180 minutes) and 2F2 (0-60 minutes) show PD profiles (resulting from PK profiles shown in FIG. 2C) of C16 diacid based analogues of the invention and of C16 diacid based analogues of the prior art following subcutaneous injection to Sprague Dawley rats;

Figure 3A:
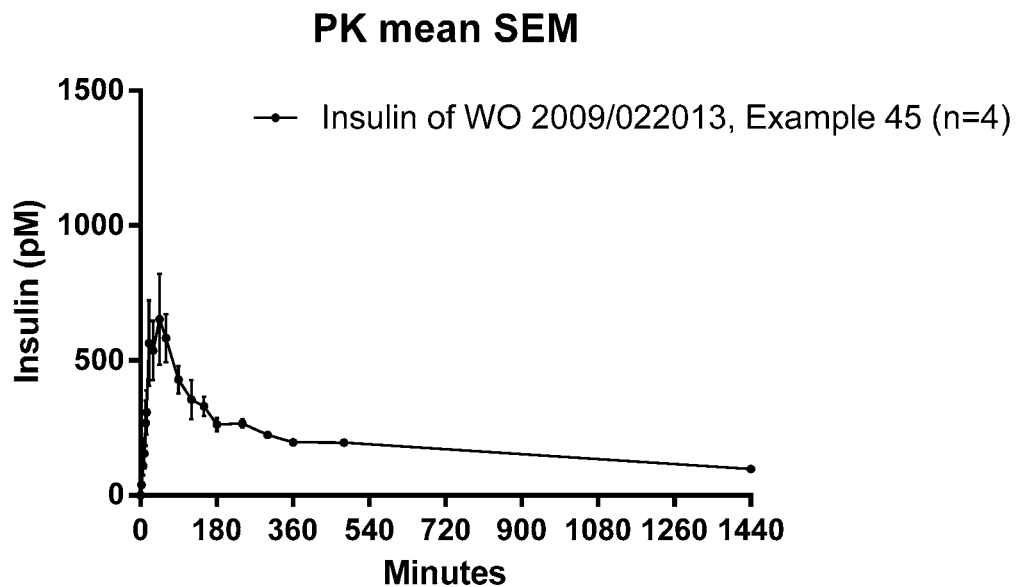
Figure 3B:
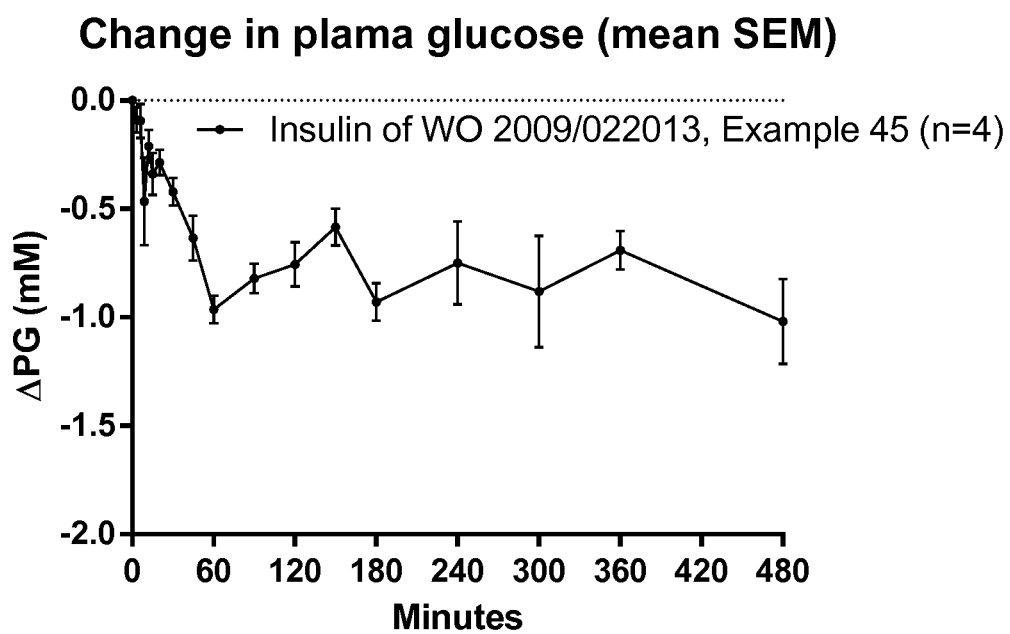
Figure 4A:
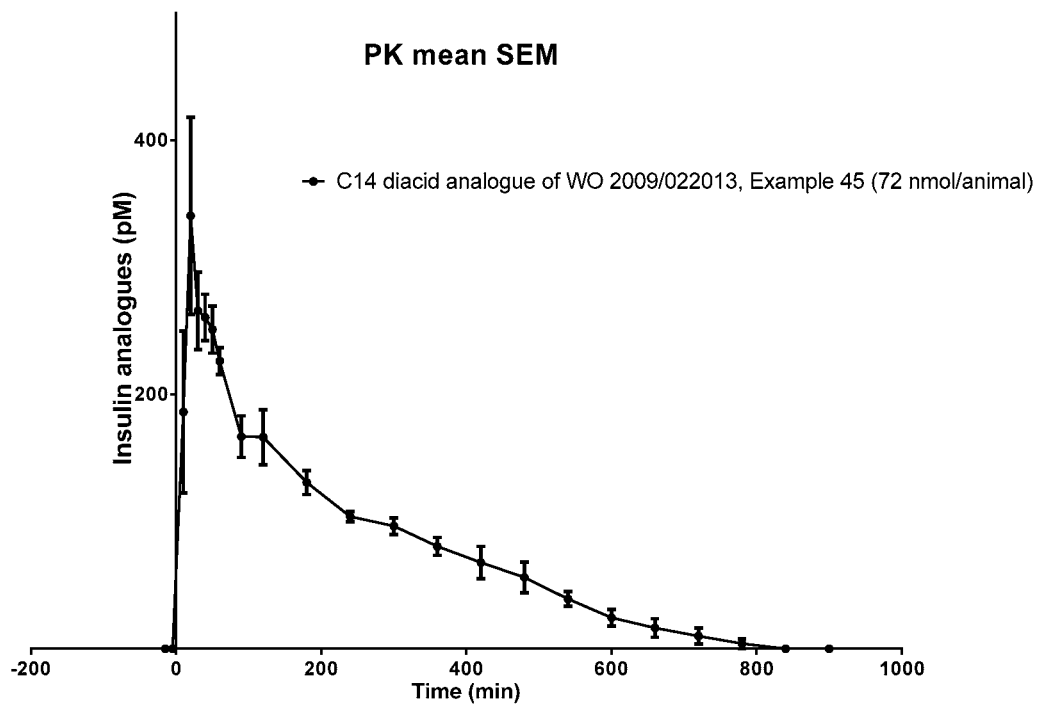
Figure 4B:
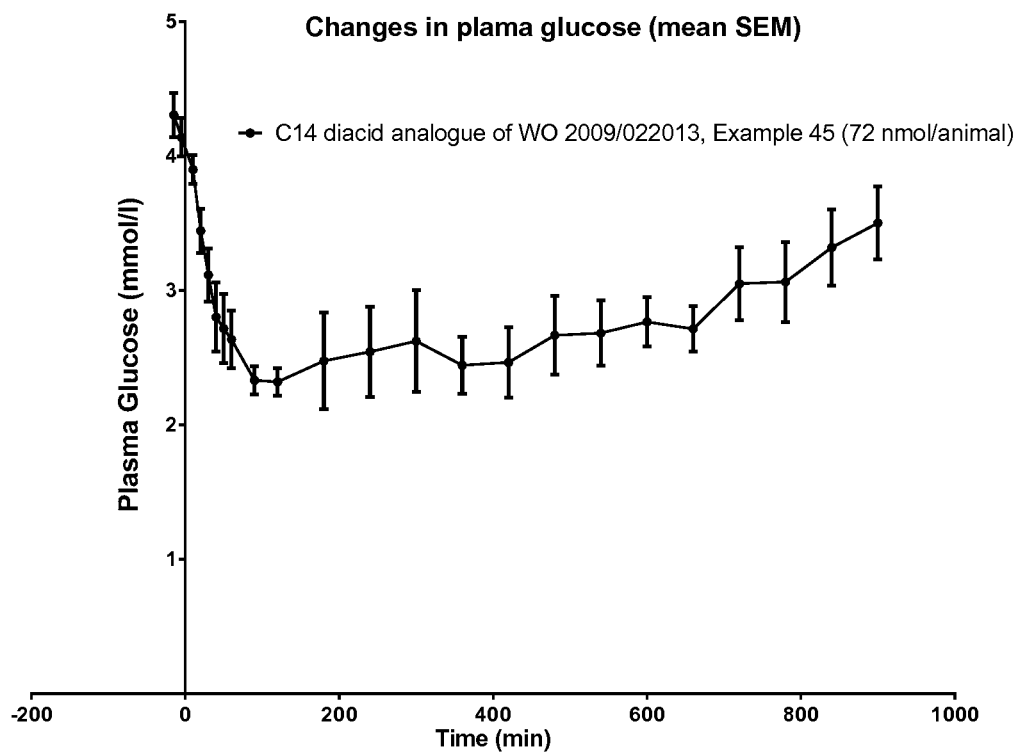
Figure 5A:
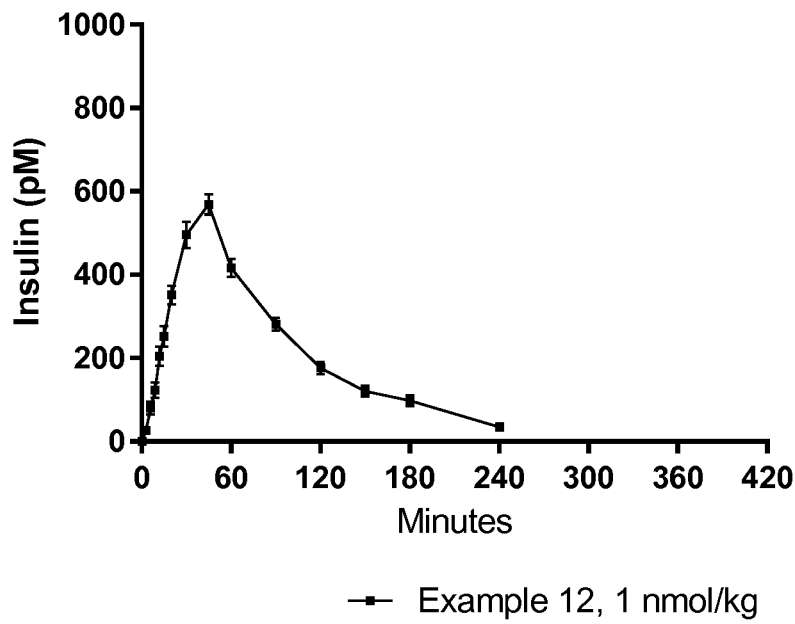
Figure 5B:
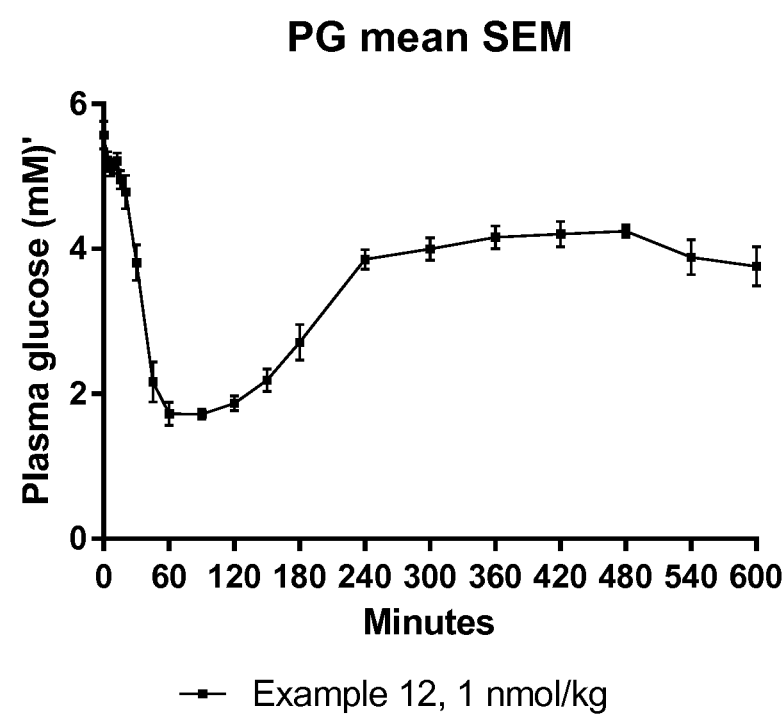
Figure 6A:
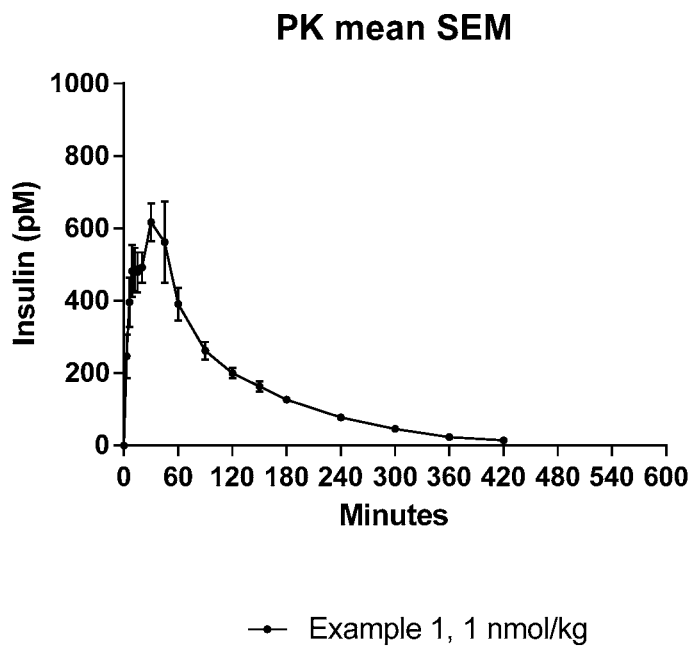
Figure 6B:
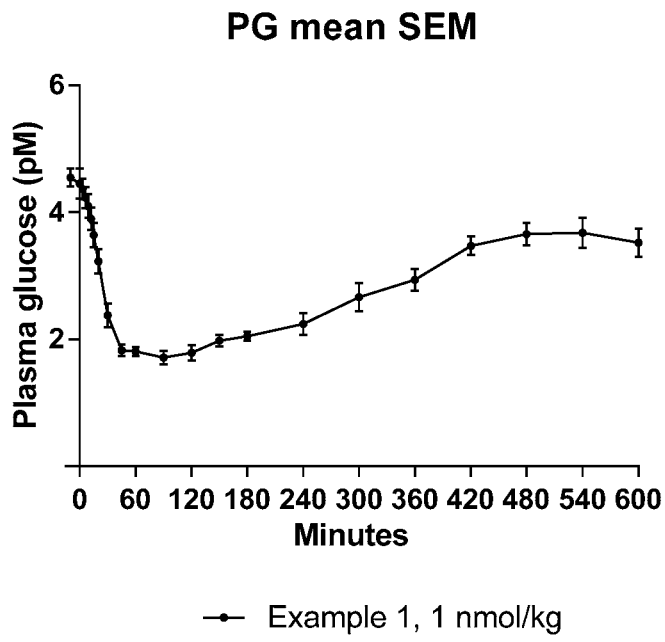
Figure 7A:
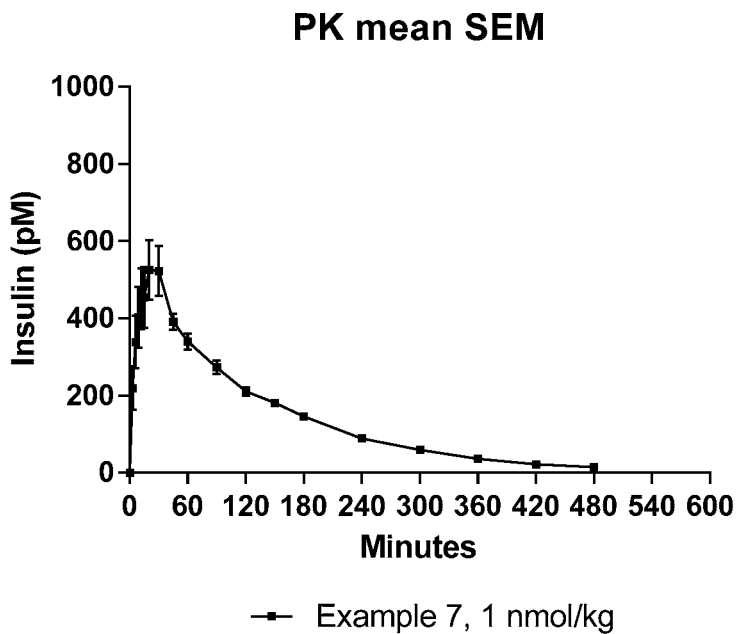
Figure 7B:
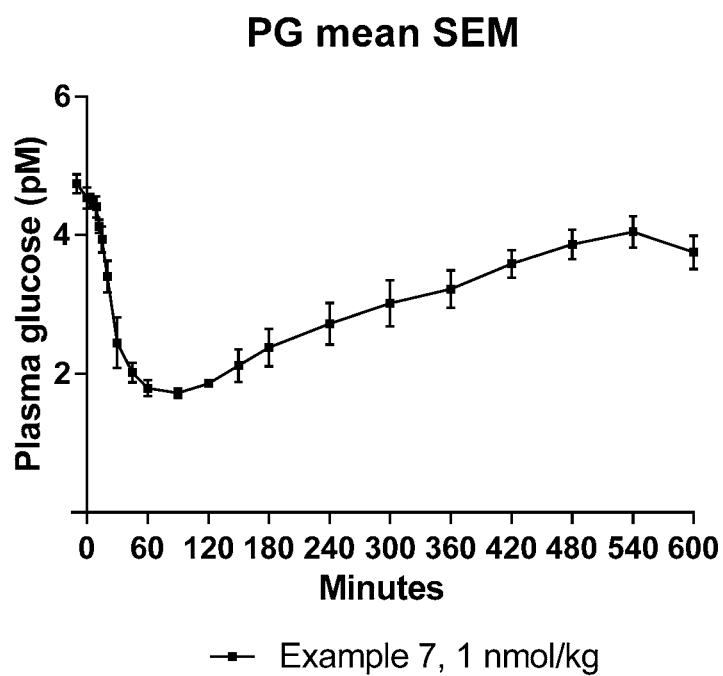
Figure 8A:
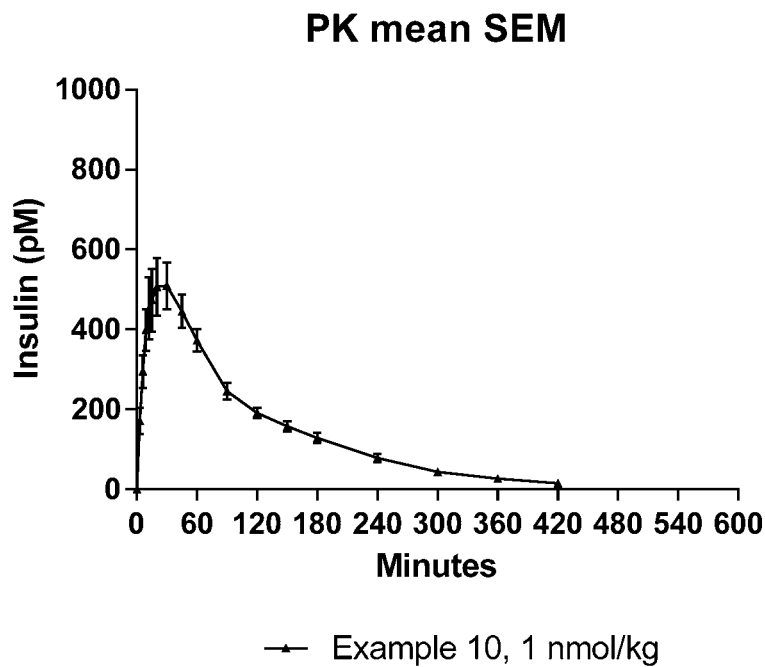
Figure 8B:
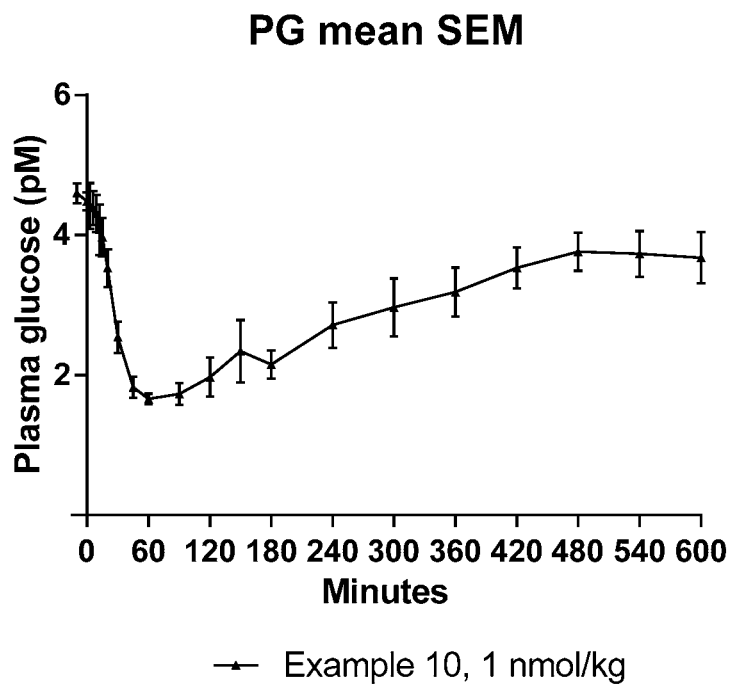

FIGS. 3A and 3B show the PK (pharmacokinetic) profile (insulin concentrations vs. time) of an insulin derivative of the prior art (Prior Art Analogue 1), i.e. A22K(N(eps)-hexadecanedioyl-gGlu-2×OEG), B29R, desB30 human insulin (WO 2009/022013, Example 45), formulated with 0 zinc per 6 insulin molecules (1 nmol/kg), and the resulting changes in plasma glucose, respectively (1 nmol/kg) following subcutaneous injection to LYD pigs;

FIGS. 4A and 4B show the PK (pharmacokinetic) profile (insulin concentrations vs. time) of Prior Art Analogue 2, a C14 diacid analogue of an insulin derivative representative of the prior art, i.e. A22K(N(eps)-hexadecanedioyl-gGlu-2× OEG), B29R, desB30 human insulin (WO 2009/022013, Example 45, Prior Art Analogue 1), formulated with 0 zinc per 6 insulin molecules (72 nmol/animal), and the resulting changes in plasma glucose, respectively (72 nmol/animal) following subcutaneous injection to LYD pigs;

FIGS. 5A and 5B show the PK (pharmacokinetic) profile (insulin concentrations vs. time) of the insulin derivative of Example 12, i.e. A22K(N(eps)tetradecanedioyl-4×gGlu), B3E, B26E, B29R, desB30 human insulin, formulated with 0 zinc per 6 insulin molecules (1 nmol/kg), and the resulting changes in plasma glucose, respectively (1 nmol/kg) following subcutaneous injection to LYD pigs;

FIGS. 6A and 6B show the PK (pharmacokinetic) profile (insulin concentrations vs. time) of the insulin derivative of Example 1, i.e. A22K(N(eps)tetradecanedioyl-gGlu-2× OEG), B3E, B27E, B28E, B29R, desB30 human insulin, formulated with 0 zinc per 6 insulin molecules (1 nmol/kg), and the resulting changes in plasma glucose, respectively (1 nmol/kg) following subcutaneous injection to LYD pigs;

FIGS. 7A and 7B show the PK (pharmacokinetic) profile (insulin concentrations vs. time) of the insulin derivative of Example 7, i.e. A22K(N(eps)tetradecanedioyl-gGlu-2× OEG), B3E, B28D, B29R, desB30 human insulin, formulated with 0 zinc per 6 insulin molecules (1 nmol/kg), and the resulting changes in plasma glucose, respectively (1 nmol/kg) following subcutaneous injection to LYD pigs; and FIGS. 8A and 8B show the PK (pharmacokinetic) profile (insulin concentrations vs. time) of the insulin derivative of Example 10, i.e. A22K(N(eps)tetradecanedioyl-4×gGlu), B3E, B28D, B29R, desB30 human insulin, formulated with 0 zinc per 6 insulin molecules (1 nmol/kg), and the resulting changes in plasma glucose, respectively (1 nmol/kg) following subcutaneous injection to LYD pigs.

EXAMPLES

The invention is further illustrated with reference to the following examples, which are not intended to be in any way limiting to the scope of the invention as claimed.
Insulin Analogue Expression and Purification
Insulin Analogue Expression The insulin analogue, i.e. the two-chain non-acylated insulin analogues, for use according to the invention are produced recombinantly by expressing a DNA sequence encoding the insulin analogue in question in a suitable host cell by well-known techniques, e.g. as disclosed in U.S. Pat. No. 6,500,645 [5930.500-US]. The insulin analogue is either expressed directly or as a precursor molecule which may have an N-terminal extension on the B-chain and/or a connecting peptide (C-peptide) between the B-chain and the A-chain. This N-terminal extension and C-peptide are cleaved off in vitro by a suitable protease, e.g. *Achromobactor lyticus* protease (ALP) or trypsin, and will therefore have a cleavage site next to position B1 and A1, respectively. N-terminal extensions and C-peptides of the type suitable for use according to this invention are disclosed in e.g. U.S. Pat. No. 5,395,922, EP 765395 and WO 9828429.

The polynucleotide sequence encoding the insulin analogue precursor for use according to the invention may be prepared synthetically by established methods, e.g. the phosphoamidite method described by Beaucage et al. (1981) *Tetrahedron Letters* 22 1859-1869, or the method described by Matthes et al. (1984) *EMBO Journal* 3 801-805. According to the phosphoamidite method, oligonucleotides are synthesised in e.g. an automatic DNA synthesiser, purified, duplexed, and ligated to form the synthetic DNA construct. A currently preferred way of preparing the DNA construct is by polymerase chain reaction (PCR).

The recombinant method will typically make use of a vector which is capable of replicating in the selected microorganism or host cell and which carries a polynucleotide sequence encoding the insulin analogue precursor for use according to the present invention. The recombinant vector may be an autonomously replicating vector, i.e., a vector which exists as an extra-chromosomal entity, the replication of which is independent of chromosomal replication, e.g. a plasmid, an extra-chromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used. The vector may be linear or closed circular plasmids and will preferably contain an element(s) that permits stable integration of the vector into the host cell's genome or autonomous replication of the vector in the cell independent of the genome.

The recombinant expression vector may be one capable of replicating in yeast. Examples of sequences which enable the vector to replicate in yeast are the yeast plasmid 2 μm replication genes REP 1-3 and origin of replication.

The vector may contain one or more selectable markers, which permit easy selection of trans-formed cells. A selectable marker is a gene the product, which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Selectable markers for use in a filamentous fungal host cell include amdS (acetamidase), argB (orni-thine carbamoyltransferase), pyrG (orotidine-5'-phosphate decarboxylase) and trpC (anthranilate syn-thase. Suitable markers for yeast host cells are ADE2, HIS3, LEU2, LYS2, MET3, TRP1, and URA3. A well suited selectable marker for yeast is the *Schizosaccharomyces pompe* TPI gene (Russell (1985) *Gene* 40 125-130).

In the vector, the polynucleotide sequence is operably connected to a suitable promoter sequence. The promoter may be any nucleic acid sequence which shows transcriptional activity in the host cell of choice including mutant, truncated, and hybrid promoters, and may be obtained from genes encoding extra-cellular or intra-cellular polypeptides either homologous or heterologous to the host cell.

Examples of suitable promoters for directing the transcription in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), and *Bacillus licheniformis* penicillinase gene (penP). Examples of suitable promoters for di-recting the transcription in a filamentous fungal host cell are promoters obtained from the genes for *Aspergillus oryzae* TAKA amylase, *Rhizomucor miehei* aspartic proteinase, *Aspergillus niger* neutral alpha-amylase, and *Aspergillus niger* acid stable alpha-amylase. In a yeast host, useful promoters are the *Saccharomyces cerevisiae* Mal, TPI, ADH, TDH3 or PGK promoters.

The polynucleotide sequence encoding the insulin peptide backbone for use according to the invention also will typically be operably connected to a suitable terminator. In yeast, a suitable terminator is the TPI terminator (Alber et al. (1982) *J. Mol. Appl. Genet.* 1 419-434).

The procedures used to combine the polynucleotide sequence encoding the insulin analogue for use according to the invention, the promoter and the terminator, respectively, and to insert them into a suitable vector containing the information necessary for replication in the selected host, are well known to persons skilled in the art. It will be understood that the vector may be constructed either by first preparing a DNA construct containing the entire DNA sequence encoding the insulin backbones for use according to the invention, and subsequently inserting this fragment into a suitable expression vector, or by sequentially inserting DNA fragments containing genetic information for the individual elements (such as the signal and pro-peptide (N-terminal extension of the B-chain), C-peptide, A- and B-chains), followed by ligation.

The vector comprising the polynucleotide sequence encoding the insulin analogue for use according to the invention is introduced into a host cell, so that the vector is maintained as a chromosomal integrant, or as a self-replicating extra-chromosomal vector. The term "host cell" encompasses any progeny of a parent cell that is not identical to the parent cell due to mutations that occur during replication. The host cell may be a unicellular microorganism, e.g. a prokaryote, or a non-unicellular microorganism, e.g. a eukaryote. Useful unicellular cells are bacterial cells such as gram positive bacteria including, but not limited to, a *Bacillus* cell, a *Streptomyces* cell, or a gram negative bacteria such as *E. coli* and *Pseudomonas* sp. Eukaryote cells may be mammalian, insect, plant, or fungal cells.

The host cell may in particular be a yeast cell. The yeast organism may be any suitable yeast organism which, on cultivation, secretes the insulin peptide backbone or the precursor hereof into the culture medium. Examples of suitable yeast organisms are include strains selected from *Saccharomyces cerevisiae, Saccharomyces kluyveri, Schizosaccharomyces pombe, Sacchoromyces uvarum, Kluyveromyces lactis, Hansenula polymorpha, Pichia pastoris, Pichia methanolica, Pichia kluyveri, Yarrowia lipolytica, Candida* sp., *Candida utilis, Candida cacaoi, Geotrichum* sp., and *Geotrichum fermentans*.

The transformation of the yeast cells may for instance be effected by protoplast formation followed by transformation by known methods. The medium used to cultivate the cells may be any conventional medium suitable for growing yeast organisms.

Insulin Analogue Purification

The secreted insulin analogue or precursor hereof may be recovered from the medium by conventional procedures including separating the yeast cells from the medium by centrifugation, by filtration or by catching or adsorbing the insulin analogue or precursor hereof on an ion exchange matrix or on a reverse phase absorption matrix, precipitating the proteinaceous components of the supernatant, or by filtration by means of a salt, e.g. ammonium sulphate, followed by purification by a variety of chromatographic procedures, e.g. ion exchange chromatography, affinity chromatography, etc.

The purification and digestion of the insulin peptide backbones of this invention is carried out as follows:

The single-chain insulin analogue precursor, which may contain an N-terminal extension of the B-chain and a modified C-peptide between the B-chain and the A-chain, is purified and concentrated from the yeast culture supernatant by cation exchange (Kjeldsen et al. (1998) *Prot. Expr. Pur.* 14 309-316).

The single-chain insulin analogue precursor is matured into two-chain insulin peptide backbone by digestion with lysine-specific immobilised ALP (Kristensen et al. (1997) *J. Biol. Chem.* 20 12978-12983) or by use of trypsin to cleave off the N-terminal extension of the B-chain, if present, and the C-peptide.

Trypsin Digestion

The eluate from the cation exchange chromatography step containing the insulin analogue precursor is diluted with water to an ethanol concentration of 15-20%. Glycine is added to a concentration of 50 mM and pH is adjusted to 9.0-9.5 by NaOH. Trypsin is added in a proportion of 1:300 (w:w) and digestion is allowed to proceed at 4 degrees. The digestion is analytically monitored every 20 minutes until digestion is completed. The digestion is terminated by addition of 1 M citric acid in a proportion of 3:100 (volume:volume).

The digestion reaction is analysed by analytical LC on a Waters Acquity Ultra-Performance Liquid Chromatography system using a C18 column and the molecular weight is confirmed by MALDI-TOF MS (Bruker Daltonics Autoflex II TOF/TOF).

The two-chain insulin analogue is purified by reversed phase HPLC (Waters 600 system) on a C18 column using an acetonitrile gradient. The desired insulin analogue is recovered by lyophilisation.

Purity is determined by analytical LC on a Waters Acquity Ultra-Performance Liquid Chromatography system using a C18 column, and the molecular weight is confirmed by MALDI-TOF MS.

ABBREVIATIONS

ALP—*Achromobactor lyticus* protease
C-peptide—connecting peptide
HPLC—high-performance liquid chromatography
IR—insulin receptor
IGF-1R insulin-like growth factor 1 receptor
LC—liquid chromatography
MALDI-TOF—matrix-assisted laser desorption ionisation time-of-flight
MS—mass spectrometry
PD—pharmacodynamics (blood/plasma glucose lowering effect)
PK—pharmacodynamics (blood/plasma insulin concentrations versus time profiles)
tBu is tert-butyl;
DCM is dichloromethane;
DIPEA=DIEA is N,N-disopropylethylamine;
DMF is N,N-dmethylformamide;
DMSO is dimethyl sulphoxide;

Fmoc is 9-fluorenylmethyloxycarbonyl;
γGlu (gGlu) is gamma L-glutamyl;
HCl is hydrochloric acid;
NMP is N-methylpyrrolidone;
OtBu is tert-butyl ester;
OEG is [2-(2-aminoethoxy)ethoxy]ethylcarbonyl;
OSu is succinimidyl-1-yloxy=2,5-dioxo-pyrrolidin-1-yloxy;
RT is room temperature;
TFA is trifluoroacetic acid;
TRIS is tris(hydroxymethyl)aminomethane; and
TSTU is O—(N-succinimidyl)-1,1,3,3-tetramethyluronium tetrafluoroborate.

Pharmacokinetic (PK) Parameters

T½ is terminal halflife;
MRT is mean residence time;
F is bioavailability (fraction absorbed);
$T_{max}$ is time to maximal plasma exposure;
$C_{max}$ is maximal plasma concentration;
D is dose;
$C_{max}/D$ is dose-normalised maximal plasma concentration;
AUC is area under the curve;
AUC/D is dose-normalised area under the curve;
% extrap is the percentage of extrapolated profile.

General Remarks

The following examples and general procedures refer to intermediate compounds and final products identified in the specification and in the synthesis schemes. The preparation of the compounds of the present invention is described in detail using the following examples, but the chemical reactions described are disclosed in terms of their general applicability to the preparation of compounds of the invention.

Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, i.e. by appropriate protection of interfering groups, by changing to other conventional reagents, or by routine modification of reaction conditions.

Alternatively, other reactions disclosed herein or otherwise conventional will be applicable to the preparation of the corresponding compounds of the invention. In all preparative methods, all starting materials are known or may easily be prepared from known starting materials. All temperatures are set forth in degrees Celsius and unless otherwise indicated, all parts and percentages are by weight when referring to yields and all parts are by volume when referring to solvents and eluents.

The compounds of the invention can be purified by employing one or more of the following procedures which are typical within the art. These procedures can—if needed—be modified with regard to gradients, pH, salts, concentrations, flow, columns and so forth. Depending on factors such as impurity profile, solubility of the insulins in question etcetera, these modifications can readily be recognised and made by a person skilled in the art.

After acidic HPLC or desalting, the compounds are isolated by lyophilisation of the pure fractions.

After neutral HPLC or anion exchange chromatography, the compounds are desalted, precipitated at isoelectric pH, or purified by acidic HPLC.

Typical Purification Procedures
RP-HPLC System:
Gilson system consisting of the following: Liquid handler Model 215, Pump Model 322-H2 and UV Detector Model 155 (UV 215 nm and 280 nm).
Anion Exchange and Desalting System:
Äkta Explorer system consists of the following: Pump Model P-900, UV detector Model UV-900 (UV 214, 254 and 280 nm), pH and conductivity detector Model pH/C-900, Fraction collector Model Frac-950.
Acidic RP-HPLC:
Column: Phenomenex Gemini, 5 μM 5 u C18 110 Å, 30×250 mm
Flow: 20 mL/min
Buffer A: 0.1% TFA in water
Buffer B: 0.1% TFA in acetonitrile
Neutral RP-HPLC:
Column: Phenomenex Gemini, 5 μM 5 u C18 110 Å, 30×250 mm
Flow: 20 mL/min
Buffer A: 10 mM Tris, 15 mM $(NH_4)_2SO_4$, pH=7.3, 20% acetonitrile in milliQ
Buffer B: 20% milliQ in acetonitrile
Anion Exchange Chromatography:
Column: Poros50HQ or Source30Q
Flow: column dependent
Buffer A: 15 mM Tris, 25 mM $NH_4OAc$, 50% EtOH, pH=7.5.
Buffer B: 15 mM Tris, 500 mM $NH_4OAc$, 50% EtOH, pH=7.5.
Desalting:
Column: HiPrep 26/10
Flow: 20 mL/min
Buffer A: 0.1% TFA in water
Buffer B: 0.1% TFA in acetonitrile Acylation reagents were synthesized either in solution or on solid phase similarly as described in e.g. WO 2009/115469.

General Procedure for the Solid Phase Synthesis of Acylation Reagents of the General Formula III

[Acyl]-[Linker]-Act wherein the Acyl and Linker groups are as defined above, and Act is the leaving group of an active ester, such as N-hydroxysuccinimide (OSu), or 1-hydroxybenzotriazole, and wherein carboxylic acids within the Acyl and Linker moieties of the acyl moiety are protected as tert-butyl esters.

Compounds of the general Formula III may be synthesised on solid support using procedures in the art of solid phase peptide synthesis known to the skilled person.

One such procedure comprises attachment of a Fmoc protected amino acid to a polystyrene 2-chlorotritylchloride resin. The attachment may be accomplished using the free N-protected amino acid in the presence of a tertiary amine, like triethyl amine or N,N-diisopropylethylamine (see references below). The C-terminal end (which is attached to the resin) of this amino acid is at the end of the synthetic sequence being coupled to the parent insulins of the invention.

After attachment of the Fmoc amino acid to the resin, the Fmoc group is deprotected using, e.g., secondary amines, like piperidine or diethyl amine, followed by coupling of another (or the same) Fmoc protected amino acid and deprotection. The synthetic sequence is terminated by coupling of mono-tert-butyl protected fatty (α, ω) diacids, like hexadecanedioic, pentadecanedioic, or tetradecanedioic acid mono-tert-butyl esters.

Cleavage of the compounds from the resin is accomplished using diluted acid like 0.5-5% TFA/DCM (trifluoroacetic acid in dichloromethane), acetic acid (e.g. 10% in DCM, or HOAc/triflouroethanol/DCM 1:1:8), or hecafluoroisopropanol in DCM (see e.g. F. Z. Dörwald: *Organic Synthesis on Solid Phase*; Wiley-VCH 2000, ISBN 3-527-29950-5; N. Sewald & H.-D. Jakubke: *Peptides: Chemistry and Biology*; Wiley-VCH, 2002, ISBN 3-527-30405-3; or *The Combinatorial Chemistry Catalog*, 1999, Novabiochem AG, and references cited therein). This ensures that tert-butyl esters present in the compounds as carboxylic acid protecting groups are not de-protected.

Finally, the C-terminal carboxy group (liberated from the resin) is activated, e.g., as the N-hydroxysuccinimide ester (OSu). This activated ester is deprotected, e.g. using neat TFA, and used either directly or after purification (crystallisation) as coupling reagent in attachment to parent insulins of the invention. This procedure is illustrated below.

General Procedure for Synthesis of Acylation Reagent on Solid Phase

Synthesis of tetradecanedioyl-4×gGlu-OSu (Chem. 4)

tetrafluoroborate (TCTU, 8.42 g, 23.69 mmol) and N,N-diisopropylethylamine (7.43 mL, 42.64 mmol) in N,N-dimethylformamide (120 mL) was added to resin and mixture was shaken for 16 hr. Resin was filtered and treated with a solution of N,N-diisopropylethylamine (5.5 mL, 31.59 mmol) in methanol/dichloromethane mixture (9:1, 150 mL, 5 min). Then resin was washed with N,N-dimethylformamide (2×150 mL), dichloromethane (2×150 mL) and N,N-dimethylformamide (2×150 mL).

Fmoc group was removed by treatment with 20% piperidine in N,N-dimethylformamide (2×150 mL, 1×5 min, 1×20 min). Resin was washed with N,N-dimethylformamide (2×150 mL), 2-propanol (2×150 mL), dichloromethane (2×150 mL) and N,N-dimethylformamide (2×150 mL). Solution of Fmoc-Glu-OtBu (10.08 g, 23.69 mmol), O-(6-chloro-benzotriazol-1-yl)-N,N,N',N'-tetramethyluronium tetrafluoroborate (TCTU, 8.42 g, 23.69 mmol) and N,N-diisopropylethylamine (7.43 mL, 42.64 mmol) in N,N-dimethylformamide (120 mL) was added to resin and mixture was shaken for 16 hr. Resin was filtered and treated with a solution of N,N-diisopropylethylamine (5.5 mL, 31.59 mmol) in methanol/dichloromethane mixture (9:1, 150 mL,

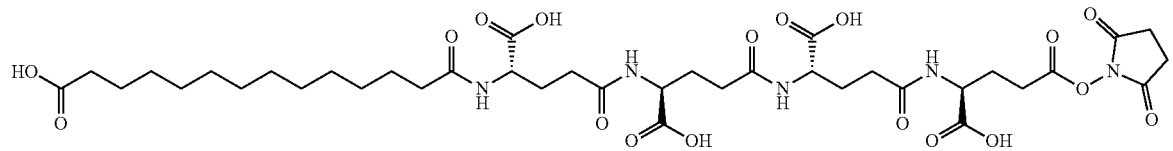 [SMILES: O=C(O)CCCCCCCCCCCCC(=O)N[C@@H](CCC(=O)N[C@@H](CCC(=O)N[C@@H](CCC(=O)N[C@@H](CCC(=O)ON1C(=O)CCC1=O)C(=O)O)C(=O)O)C(=O)O)C(=O)O]

2-Chlorotrityl resin 100-200 mesh 1.5 mmol/g (15.79 g, 23.69 mmol) was left to swell in dry dichloromethane (150 mL) for 20 minutes. A solution of Fmoc-Glu-OtBu (6.72 g, 15.79 mmol) and N,N-diisopropylethylamine (10.46 mL, 60.01 mmol) in dry dichloromethane (120 mL) was added to resin and the mixture was shaken for 16 hrs. Resin was filtered and treated with a solution of N,N-diisopropylethylamine (5.5 mL, 31.59 mmol) in methanol/dichloromethane mixture (9:1, 150 mL, 5 min). Then resin was washed with N,N-dimethylformamide (2×150 mL), dichloromethane (2×150 mL) and N,N-dimethylformamide (2×150 mL).

Fmoc group was removed by treatment with 20% piperidine in N,N-dimethylformamide (2×150 mL, 1×5 min, 1×20 min). Resin was washed with N,N-dimethylformamide (2×150 mL), 2-propanol (2×150 mL), dichloromethane (2×150 mL) and N,N-dimethylformamide (2×150 mL). Solution of Fmoc-Glu-OtBu (10.08 g, 23.69 mmol), O-(6-chloro-benzotriazol-1-yl)-N,N,N',N'-tetramethyluronium tetrafluoroborate (TCTU, 8.42 g, 23.69 mmol) and N,N-diisopropylethylamine (7.43 mL, 42.64 mmol) in N,N-dimethylformamide (120 mL) was added to resin and mixture was shaken for 16 hr. Resin was filtered and treated with a solution of N,N-diisopropylethylamine (5.5 mL, 31.59 mmol) in methanol/dichloromethane mixture (9:1, 150 mL, 5 min). Then resin was washed with N,N-dimethylformamide (2×150 mL), dichloromethane (2×150 mL) and N,N-dimethylformamide (2×150 mL).

Fmoc group was removed by treatment with 20% piperidine in N,N-dimethylformamide (2×150 mL, 1×5 min, 1×20 min). Resin was washed with N,N-dimethylformamide (2×150 mL), 2-propanol (2×150 mL), dichloromethane (2×150 mL) and N,N-dimethylformamide (2×150 mL). Solution of Fmoc-Glu-OtBu (10.08 g, 23.69 mmol), O-(6-chloro-benzotriazol-1-yl)-N,N,N',N'-tetramethyluronium 5 min). Then resin was washed with N,N-dimethylformamide (2×150 mL), dichloromethane (2×150 mL) and N,N-dimethylformamide (2×150 mL).

Fmoc group was removed by treatment with 20% piperidine in N,N-dimethylformamide (2×150 mL, 1×5 min, 1×20 min). Resin was washed with N,N-dimethylformamide (2×150 mL), 2-propanol (2×150 mL), dichloromethane (2×150 mL) and N,N-dimethylformamide (2×150 mL). Solution of tetradecanedioic acid mono-tert-butyl ester (7.45 g, 23.69 mmol), O-(6-chloro-benzotriazol-1-yl)-N,N,N',N'-tetramethyluronium tetrafluoroborate (TCTU, 8.42 g, 23.69 mmol) and N,N-diisopropylethylamine (7.43 mL, 42.64 mmol) in the mixture of N,N-dimethylformamide (40 mL) and dichloromethane (80 mL) was added to resin and mixture was shaken for 16 hr. Resin was filtered and washed with dichloromethane (2×150 mL), N,N-dimethylformamide (2×150 mL), methanol (2×150 mL) and dichloromethane (10×150 mL).

The product was cleaved from the resin by the treatment with trifluoroethanol (150 mL) overnight. Resin was filtered off and washed with dichloromethane (3×100 mL). The solvent was removed under reduced pressure. The residue was purified by column chromatography on silica gel (gradient elution dichloromethane/methanol 100:0 to 95:5) giving titled compound as white solid.

Product was dried in vacuo to yield (S)-2-((S)-4-tert-Butoxycarbonyl-4-{(S)-4-tert-butoxycarbonyl-4-[(S)-4-tert-butoxycarbonyl-4-(13-tert-butoxycarbonyl-tridecanoylamino)-butyrylamino]-butyrylamino}-butyrylamino)-pentanedioic acid 1-tert-butyl ester.

Yield: 14.77 g (89%).

$^1$H NMR spectrum (300 MHz, CDCl$_3$, OH): 7.22 (d, J=7.7 Hz, 1H); 6.97 (d, J=7.9 Hz, 1H); 6.72 (d, J=7.9 Hz, 1H); 6.41 (d, J=7.9 Hz, 1H); 4.59-4.43 (m, 4H); 2.49-2.13

(m, 16H); 2.06-1.72 (m, 4H); 1.70-1.52 (m, 4H); 1.52-1.38 (m, 45H); 1.35-1.21 (m, 16H).

LC-MS purity: 100% (ELSD).

LC-MS Rt (Sunfire 4.6 mm×100 mm, acetonitrile/water 50:50 to 100:0+0.1% FA): 7.39 min.

LC-MS m/z: 1055.0 (M+H)+.

The obtained tert-butyl protected tetradecanedioyl-4× gGlu-OH ((S)-2-((S)-4-tert-Butoxycarbonyl-4-{(S)-4-tert-butoxycarbonyl-4-[(S)-4-tert-butoxycarbonyl-4-(13-tert-butoxycarbonyl-tridecanoylamino)-butyrylamino]-butyrylamino}-butyrylamino)-pentanedioic acid 1-tert-butyl ester) was dissolved in tetrahydrofuran. DIPEA was added followed by TSTU dissolved in acetonitrile. The reaction mixture was stirred for 3 h and then evaporated in vacuo, re-dissolved in ethyl acetate, washed with 0.1M HCl (aq), dried over MgSO$_4$, filtered and evaporated in vacuo. LC-MS (electrospray): m/z=1174.7 (M+Na$^+$). Calc: 1175.4.

The protected and OSu-activated compound was dissolved in 10 mL TFA and stirred at room temperature overnight. Diethyl ether was added and the precipitate formed was filtered off and dried on vacuum overnight to afford (S)-2-((S)-4-Carboxy-4-{(S)-4-carboxy-4-[(S)-4-carboxy-4-(13-carboxy-tridecanoylamino)-butyrylamino]-butyrylamino}-butyrylamino)-pentanedioic acid 5-(2,5-dioxo-pyrrolidin-1-yl) ester (tetradecanedioyl-4×gGlu-OSu).

LC-MS (electrospray): m/z=872.2 (M+H$^+$). Calc: 871.9.

General Procedure for Synthesis of Acylation Reagent on Solid Phase

Synthesis of tetradecanedioyl-gGlu-2×OEG-OSu (Chem. 5)

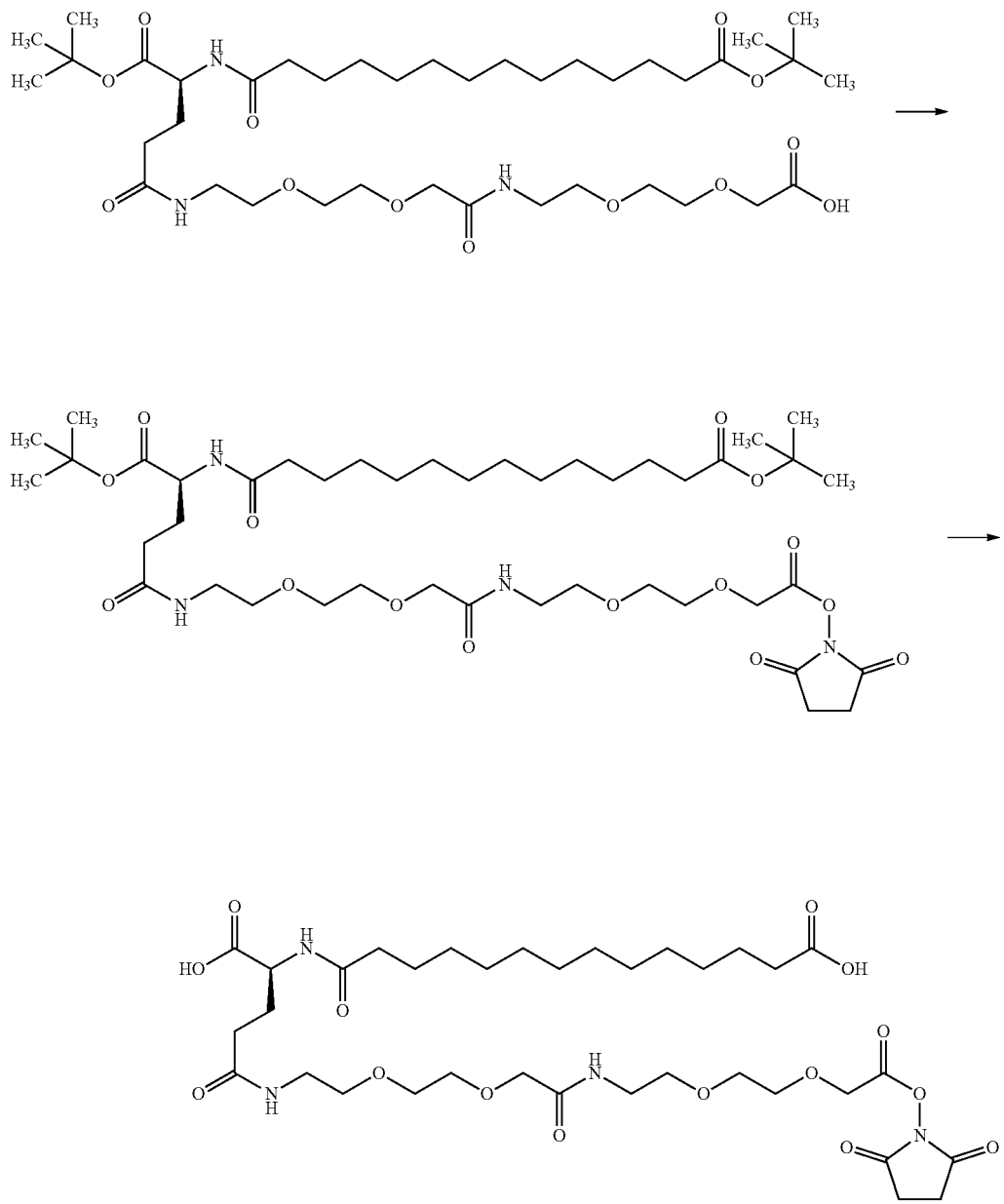

13-{(S)-1-tert-Butoxycarbonyl-3-[2-(2-{[2-(2-carboxymethoxy-ethoxy)-ethylcarbamoyl]-methoxy}-ethoxy)-ethylcarbamoyl]-propylcarbamoyl}-tridecanoic acid tert-butyl ester 2-Chlorotrityl resin 100-200 mesh 1.7 mmol/g (79.8 g, 135.6 mmol) was left to swell in dry dichloromethane (450 mL) for 20 minutes. A solution of {2-[2-(9H-fluoren-9-ylmethoxycarbonylamino)-ethoxy]-ethoxy}-acetic acid (Fmoc-OEG-OH, 34.9 g, 90.4 mmol) and N,N-diisopropylethylamine (59.9 mL, 343.6 mmol) in dry dichloromethane (100 mL) was added to resin and the mixture was shaken for 4 hrs. Resin was filtered and treated with a solution of N,N-diisopropylethylamine (31.5 mL, 180.8 mmol) in methanol/dichloromethane mixture (4:1, 150 mL, 2×5 min). Then resin was washed with N,N-dimethylformamide (2×300 mL), dichloromethane (2×300 mL) and N,N-dimethylformamide (3×300 mL). Fmoc group was removed by treatment with 20% piperidine in dimethylformamide (1×5 min, 1×30 min, 2×300 mL). Resin was washed with N,N-dimethylformamide (3×300 mL), 2-propanol (2×300 mL) and dichloromethane (350 mL, 2×300 mL).

Solution of {2-[2-(9H-fluoren-9-ylmethoxycarbonylamino)-ethoxy]-acetic acid (Fmoc-OEG-OH, 52.3 g, 135.6 mmol), O-(6-chloro-benzotriazol-1-yl)-N,N,N',N'-tetramethyluronium tetrafluoroborate (TCTU, 48.2 g, 135.6 mmol) and N,N-diisopropylethylamine (42.5 mL, 244.1 mmol) in N,N-dimethylformamide (250 mL) was added to resin and mixture was shaken for 2 hr. Since ninhydrin test was still positive, resin was filtered and treated with the same amounts of reagents for another 30 minutes. Resin was filtered and washed with N,N-dimethylformamide (2×300 mL), dichloromethane (2×300 mL) and N,N-dimethylformamide (3×300 mL). Fmoc group was removed by treatment with 20% piperidine in dimethylformamide (1×5 min, 1×30 min, 2×300 mL). Resin was washed with N,N-dimethylformamide (3×300 mL), 2-propanol (2×300 mL) and dichloromethane (350 mL, 2×300 mL).

Solution of (S)-2-(9H-fluoren-9-ylmethoxycarbonylamino)-pentanedioic acid 1-tert-butyl ester (Fmoc-LGlu-OtBu, 57.7 g, 135.6 mmol), O-(6-chloro-benzotriazol-1-yl)-N,N,N',N'-tetramethyluronium tetrafluoroborate (TCTU, 48.2 g, 135.6 mmol) and N,N-diisopropylethylamine (42.5 mL, 244.1 mmol) in N,N-dimethylformamide (250 mL) was added to resin and mixture was shaken for 1 hr. Resin was filtered and washed with N,N-dimethylformamide (2×300 mL), dichloromethane (2×300 mL) and N,N-dimethylformamide (2×300 mL). Fmoc group was removed by treatment with 20% piperidine in dimethylformamide (1×5 min, 1×30 min, 2×300 mL). Resin was washed with N,N-dimethylformamide (3×300 mL), 2-propanol (2×300 mL) and dichloromethane (350 mL, 2×300 mL).

Solution of tetradecanedioic acid mono-tert-butyl ester (C14(OtBu)-OH, 42.7 g, 135.6 mmol), O-(6-chloro-benzotriazol-1-yl)-N,N,N',N'-tetramethyluronium tetrafluoroborate (TCTU, 48.2 g, 135.6 mmol) and N,N-diisopropylethylamine (42.5 mL, 244.1 mmol) in dichloromethane/N,N-dimethylformamide mixture (4:1, 300 mL) was added to resin and mixture was shaken for 1.5 hr. Resin was filtered and washed with N,N-dimethylformamide (6×300 mL), dichloromethane (4×300 mL), methanol (4×300 mL) and dichloromethane (7×600 mL). The product was cleaved from resin by treatment with 2,2,2-trifluorethanol (600 mL) for 18 hrs. Resin was filtered off and washed with dichloromethane (4×300 mL), dichloromethane/2-propanol mixture (1:1, 4×300 mL), 2-propanol (2×300 mL) and dichloromethane (6×300 mL). Solutions were combined; solvent evaporated and crude product was purified by column chromatography (Silicagel 60A, 0.060-0.200 mm; eluent: dichloromethane/methanol 1:0-9:1).

Pure 13-{(S)-1-tert-Butoxycarbonyl-3-[2-(2-{[2-(2-carboxymethoxy-ethoxy)-ethylcarbamoyl]-methoxy}-ethoxy)-ethylcarbamoyl]-propylcarbamoyl}-tridecanoic acid tert-butyl ester was dried in vacuo and obtained as orange oil.

Yield: 55.2 g (77%).

RF (SiO$_2$, dichloromethane/methanol 9:1): 0.35.

1H NMR spectrum (300 MHz, CDCl$_3$, δH): 7.37 (bs, 1H); 7.02 (bs, 1H); 6.53 (d, J=7.9 Hz, 1H); 4.54-4.38 (m, 1H); 4.17 (s, 2H); 4.02 (s, 2H); 3.82-3.40 (m, 16H); 2.37-2.12 (m, 7H); 2.02-1.82 (m, 1H); 1.71-1.51 (m, 4H); 1.47 (s, 9H); 1.43 (s, 9H); 1.25 (bs, 16H).

LC-MS purity: 100%.

LC-MS Rt (Sunfire 4.6 mm×100 mm, acetonitrile/water 70:30 to 100:0+0.1% FA): 3.93 min.

LC-MS m/z: 791.0 (M+H)+.

13-{(S)-1-tert-Butoxycarbonyl-3-[2-(2-{[2-(2-carboxymethoxy-ethoxy)-ethylcarbamoyl]-methoxy}-ethoxy)-ethylcarbamoyl]-propylcarbamoyl}-tridecanoic acid tert-butyl ester (tetradecanedioyl-gGlu-2×OEG-OH, 8.89 g, 11.3 mmol) was dissolved in 100 mL of acetonitrile, and TSTU (4.07 g, 13.5 mmol) and DIPEA (2.35 mL, 13.5 mmol) were added to the stirred solution and the mixture was stirred at room temperature for 1 hour. The solvent was evaporated and the residue was dissolved in dichloromethane and washed twice with 0.05M HCl.

The organic phase was dried (MgSO$_4$) and evaporated in vacuo. This afforded 9.98 g (100%) of 13-((S)-1-tert-Butoxycarbonyl-3-{2-[2-({2-[2-(2,5-dioxo-pyrrolidin-1-yloxycarbonylmethoxy)-ethoxy]-ethylcarbamoyl}-methoxy)-ethoxy]-ethylcarbamoyl}-propylcarbamoyl)-tridecanoic acid tert-butyl ester as an oil.

13-((S)-1-tert-Butoxycarbonyl-3-{2-[2-({2-[2-(2,5-dioxo-pyrrolidin-1-yloxycarbonylmethoxy)-ethoxy]-ethylcarbamoyl}-methoxy)-ethoxy]-ethylcarbamoyl}-propylcarbamoyl)-tridecanoic acid tert-butyl ester (4 g) was dissolved in trifluoroacetic acid (10 mL) and the mixture was stirred at room temperature for 1 hour and evaporated in vacuo. The residue was dissolved in dichloromethane (10 mL) and evaporated in vacuo. Addition of cold diethyl ether (10 mL) resulted in precipitation of a white greasy solid. This was isolated by decantation and was dried in vacuo. This afforded 3.4 g (quant.) of 14-[[(1S)-1-carboxy-4-[2-[2-[2-[2-[2-(2,5-dioxopyrrolidin-1-yl)oxy-2-oxoethoxy]ethoxy]ethylamino]-2-oxoethoxy]ethoxy]ethylamino]-4-oxobutyl]amino]-14-oxotetradecanoic acid (tetradecanedioyl-gGlu-2×OEG-OSu), which was stored at −18° C.

LC-MS (electrospray): m/z=775.33; calc: 774.8.

General Procedure (A) for Acylation of Insulins and Purification of Acylated Analogues A general procedure (A) for the acylation and purification of the insulin derivatives of the invention is described in details in Example 1, below, and has been applied to the synthesis of additional compounds as indicated below. Purification using other methods (as described above) has also been done for some of these derivatives.

Acylated analogues of the invention are made by acylation of recombinant insulin analogues by acylation in an aqueous environment at high pH such as pH 9.5, 10, 10.5 11, 11.5, 12, 12.5 or 13. The acylation reagent may be dissolved in water or in a non-aqueous polar solvent, such as DMF or NMP, and added to the insulin solution with vigorous stirring. After addition of the acylation reagent, conversion is analysed by HPLC and, if necessary, more acylation reagent is added. Purification is done as described above.

General Procedure (B) for Solid Phase Synthesis and Purification of Acylated Analogues A general procedure (B) for the solid phase synthesis and purification of the insulin derivatives of the invention is described in details below, and has been applied to the synthesis of additional compounds as indicated below. Purification using other methods (as described above) have also been done for some of these derivatives.

Insulin A and B chains were prepared on a Prelude peptide synthesiser using a general Fmoc based solid phase peptide coupling method.

Resins Used:
Fmoc-Lys(Mtt)-Wang; and Fmoc-Arg-Pbf-Wang.

Amino acids (listed below) and oxyma were dissolved in DMF to a concentration of 0.3 M:

Fmoc-Ala-OH; Fmoc-Arg(Pbf)-OH; Fmoc-Asn(Trt)-OH; Fmoc-Asp(OtBu)-OH; Fmoc-Cys(Trt)-OH; Fmoc-Gln(Trt)-OH; Fmoc-Glu(OtBu)-OH; Fmoc-Gly-OH; Fmoc-His(Trt)-OH; Fmoc-Ile-OH; Fmoc-Leu-OH; Fmoc-Lys(Boc)-OH; Fmoc-Met-OH; Fmoc-Phe-OH; Fmoc-Pro-OH; Fmoc-Ser(tBu)-OH; Fmoc-Thr(tBu)-OH; Fmoc-Trp(Boc)-OH; Fmoc-Tyr(tBu)-OH; and Fmoc-Val-OH.

Special/unnatural amino acids: Boc-Phe-OH; Boc-Gly-OH; and Fmoc-Cys(Acm)-OH.

Procedure

Standard coupling conditions used on resins were: 8 eq amino acid, DIC, collidine and oxyma (ethyl (hydroxyimino)cyanoacetate) in NMP for 1 hour, in the case of Fmoc-Arg(Pbf)-OH, a double coupling protocol (2×1 h) was used.

Standard deprotection conditions used were: 20% piperdine in NMP (2×5.5 ml for 2×7.5 min or 2×10 min), followed by washing with NMP and DCM.

For acylation at Lys prior to cleavage from the resin the following protocol is used (in this case the N-terminal amino acid is Boc protected).

A-Chain Deprotection of Mtt Group on A22K and Acylation with tBu Protected Activated Acylation Reagent ([Acyl]-[Linker]-OSu, Eq. Tetradecanedioyl-gGlu-2×OEG-OSu and Tetradecanedioyl-gGlu-2×OEG-OSu (Both Protected as tBu Esters at Terminal and Alpha Carboxyl Groups)

Step 1: To the resin was added HFIP (12 mL), and the reaction shaken for 20 min. After removal of solvent by filtration the resin was washed with DCM (4×15 ml) and dried over a nitrogen stream Step 2: To the above resin was added DMF (8 mL) and DIPEA (1.5 mL). A solution of activated acylation reagent (0.75 g in 2 mL DMF) was then added and the reaction shaken for 15 h, drained and washed with DCM (3×15 ml).

Deprotection of the Mtt Group and Sequential Preparation of Side Chain

To the resin was added HFIP (6 mL), and the reaction incubated for 20 min. After removal of the solvent the resin was washed with DCM (6 mL). HFIP (6 mL) was added to the resin, and the reaction incubated for 20 min. The resin was washed with DCM (2×7.5 mL) and Collidine (2×7.5 mL), followed by additional washes with DCM (2×7.5 mL). The side chain was built up by sequential standard couplings using Fmoc-Glu-OtBu, Fmoc-OEG-OH, and 14-tert-butoxy-14-oxo-tetradecanoic acid or 16-tert-butoxy-16-oxo-hexadecanoic acid.

A6C-A11C Disulfide Formation

The resin was treated for 15 min with a 0.5% solution of iodine in DCM/HFIP (30 mL of 1:1 mixture). After removal of solvent by filtration the resin was washed with DCM (3×20 ml) and dried over a nitrogen stream.

A-Chain Cleavage from the Resin and Activation of A20-Cys as S—S-Pyridyl

The resin was treated with a solution of TFA (30 mL), triisopropylsilane (1 ml), water (0.75 ml) and dithiodipyridine (0.75 g) for 3 h, and then the filtrate was collected and added to 150 ml ether (split into 6 plastic NUNC tubes) to precipitate the peptide. The tubes were centrifuged at 3500 rpm for 3 min, the ether layer was decanted, and this ether step was repeated a further 3 times. The crude material was combined and allowed to dry overnight at RT to give the desired peptide A-chain.

B-Chain Cleavage from the Resin

The resin was treated with a solution of TFA (30 mL), triisopropylsilane (1 ml), water (0.75 ml) and dithiothreitol (0.5 g) for 3 h, and then the filtrate was collected and added to ether (150 ml, split into 6 plastic NUNC tubes) to precipitate the peptide. The tubes were centrifuged at 3500 rpm for 3 min, the ether layer was decanted, and this ether step was repeated a further 3 times. The crude material was allowed to dry overnight at RT to give the desired peptide B-chain.

A20C-B19C Disulfide Formation

To a mixture of A-chain (0.33 g) and B-chain (0.33 g) was added DMSO (8 mL) and DIPEA (1 mL) and the mixture stirred for 20 min, then added drop-wise with stirring to 140 ml of neutral buffer solution (water, TRIS (10 mM), ammonium sulphate (15 mM), 20% acetonitrile) to a total volume of approx. 150 ml.

The mixture was then purified by reverse phase chromatography using following set up Phenomenex Gemini 5 μM 5 u C18 110 Å, 30×250 mm column, running at 20 mL/min 10% B to 60% B over 40 min Eluant A=10 mM TRIS, 15 mM ammonium sulfate, pH=7.3, 20% ACN in milliQ water Eluant B=20% miliQ water in acetonitrile Pure fractions were pooled, flash frozen and freeze dried.

A7C-B7C Disulfide Formation

Freeze dried intermediate from the previous step was re-dissolved in 5 mL DMSO. Acetic acid (20 mL) and water (4 mL) was added, followed by iodine in AcOH (3 mL of 40 mM)

After total reaction time of 20 min, the reaction quenched with 1M sodium ascorbate, and then added to a stirred solution of water (90 mL).

The mixture was then purified by reverse phase chromatography using following set up Phenomenex Gemini 5 μM 5 u C18 110 Å, 30×250 mm column, running at 20 mL/min 10% B to 45% B over 40 min Eluant A=0.1% TFA in milliQ water Eluant B=0.1% TFA in acetonitrile Pure fractions were pooled, flash frozen and freeze dried to give the desired product.

Example 1

General Procedure (A)
A22K(N(eps)tetradecanedioyl-gGlu-2×OEG), B3E, B27E, B28E, B29R, desB30 Human Insulin; (SEQ ID NOS: 3 and 16)

IUPAC (OpenEye, IUPAC style) name: N{Alpha}([GluB3,GluB27,GluB28, ArgB29],des-ThrB30-Insulin(human)-(A)-peptidyl)-N{Epsilon}[2-[2-[2-[[2-[2-[2-[[(4S)-4-carboxy-4-(1 3-carboxytridecanoylamino)butanoyl]amino]ethoxy]ethoxy]acetyl]amino]ethoxy]-ethoxy]acetyl]Lys, (B)-peptide.

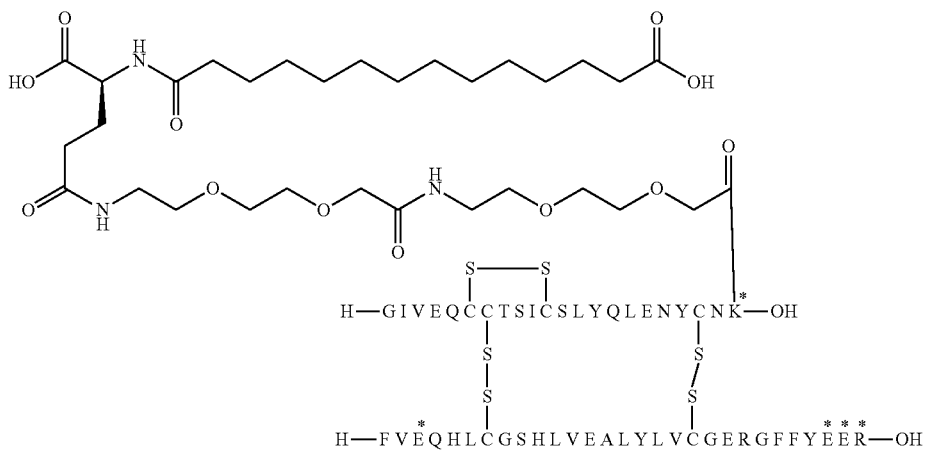

A22K, B3E, B27E, B28E, B29R, desB30 human insulin (0.5 g, 0.084 mmol) was dissolved in 7 ml 100 mM aq. Na$_2$CO$_3$. pH was adjusted to 11.3 with addition of 1 N aq. NaOH. 14-[[(1S)-1-carboxy-4-[2-[2-[2-[2-[2-[2-(2,5-dioxopyrrolidin-1-yl)oxy-2-oxoethoxy]ethoxy]ethylamino]-2-oxoethoxy]ethoxy]ethylamino]-4-oxobutyl]amino]-14-oxotetradecanoic acid (tetradecanedioyl-gGlu-2×OEG-OSu) (0.26 g, 0.336 mmol) was dissolved in a mixture of 1 ml acetonitrile and 1 ml NMP and added to the insulin solution under vigorous stirring. 1 N aq. NaOH was added during the addition to keep pH at 10.5-11.4. Water (7 mL) was added to the mixture and 1 N HCl was added to acidify the reaction mixture (to pH 1.5) and acetonitrile (1 mL) was added. The mixture was purified by preparative HPLC (column: Phenomenex Axial, 5 µM C18 110 Å, 30×250 mm using a gradient of 10% B to 40% B over 50 min, 20 ml/min. A-buffer: 0.1% TFA in water, B-buffer: 0.1% TFA in acetonitrile). Pure fractions were pooled and lyophilised to afford 106 mg (19%) of the title insulin.

LC-MS (electrospray): m/z=1650.4 (M+4)/4. Calc: 1650.4.

Example 2

General Procedure (A)
A14E, A22K(N(eps)tetradecanedioyl-gGlu-2×OEG), B3E, B27E, B28E, B29R, desB30 Human Insulin; (SEQ ID NOS: 2 and 16)

IUPAC (OpenEye, IUPAC style) name: {Alpha}([GluA14,GluB3,GluB27,GluB28, ArgB29],des-ThrB30-Insulin(human)-(A)-peptidyl)-N{Epsilon}[2-[2-[2-[[2-[2-[2-[[(4S)-4-carboxy-4-(13-carboxytridecanoylamino) butanoyl]amino]ethoxy]ethoxy]acetyl]amino]ethoxy] ethoxy]acetyl]Lys,(B)-peptide.

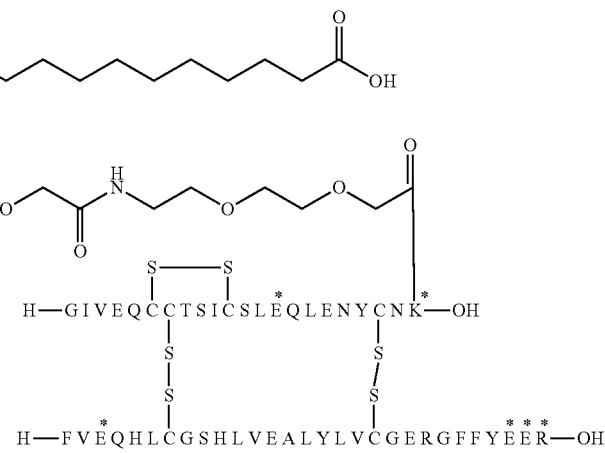

LC-MS (electrospray): m/z=1641.9 (M+4)/4. Calc: 1641.3.

Example 3

General Procedure (A)

A22K(N(eps)tetradecanedioyl-4×gGlu), B3E, B27E, B28E, B29R, desB30 Human Insulin; (SEQ ID NOS: 2 and 16)

IUPAC (OpenEye, IUPAC style) name: N{Alpha}([GluB3,GluB27,GluB28,ArgB29], des-ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]-butanoyl]Lys,(B)-peptide.

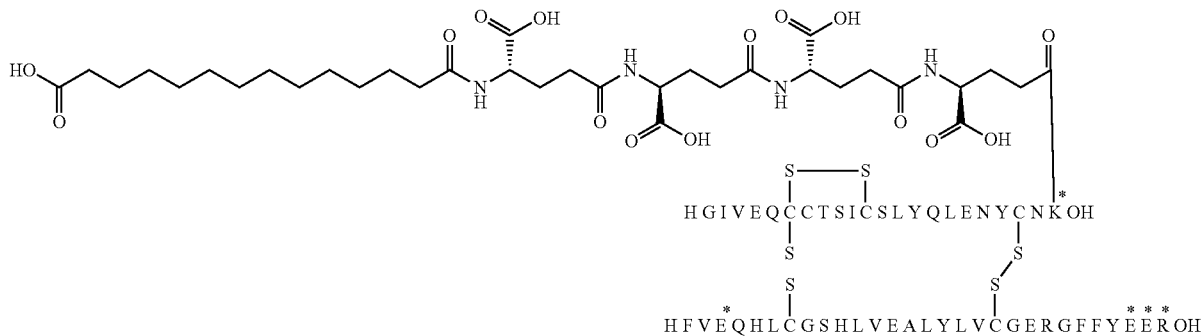

LC-MS (electrospray): m/z=1674.7 (M+4)/4. Calc: 1674.2.

Example 4

General Procedure (A)

A14E, A22K(N(eps)tetradecanedioyl-4×gGlu), B3E, B27E, B28E, B29R, desB30 Human Insulin; (SEQ ID NOS: 2 and 16)

IUPAC (OpenEye, IUPAC style) name: N{Alpha}([GluA14,GluB3,GluB27,GluB28, Arg B29],des-ThrB30-Insulin(human)-(A)-peptidyl)-N {Epsilon}[(4S)-4-carboxy-4-[[(4S)-4-carboxy-4-[[(4S)-4-carboxy-4-[[(4S)-4-carboxy-4-(13-carboxytridecanoylamino) butanoyl]amino]butanoyl]amino]butanoyl]amino]butanoyl]Lys,(B)-peptide.

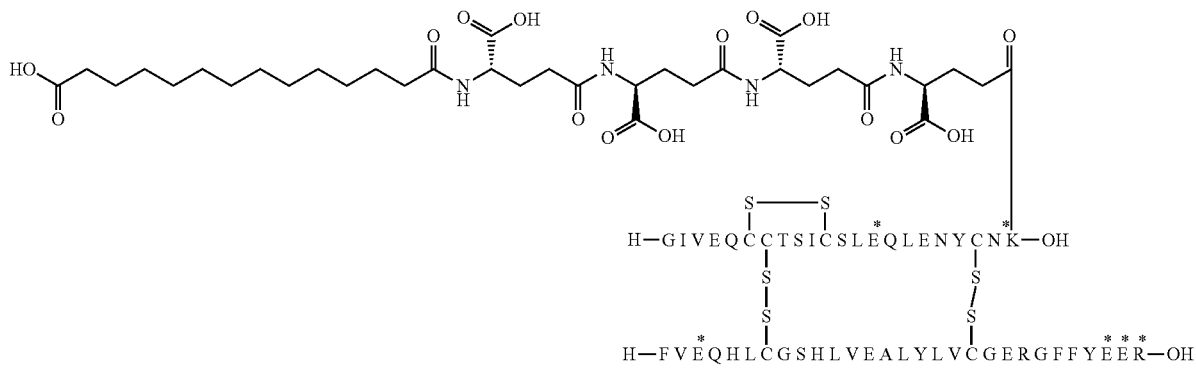

LC-MS (electrospray): m/z=1665.7 (M+4)/4. Calc: 1666.1.

Example 5

General Procedure (A)

A22K(N(eps)tetradecanedioyl-gGlu-2×OEG), B3E, B27P, B28E, B29R, desB30 human Insulin; (SEQ ID NOS: 3 and 17)

IUPAC (OpenEye, IUPAC style) name: N{Alpha}([GluB3,ProB27,GluB28,ArgB29], des-ThrB30-Insulin(human)-(A)-peptidyl)-N{Epsilon}[2-[2-[2-[[2-[2-[2-[[(4S)-4-carboxy-4-(13-carboxytridecanoylamino)butanoyl]amino]ethoxy]ethoxy]acetyl]amino]ethoxy]-ethoxy]acetyl]Lys, (B)-peptide.

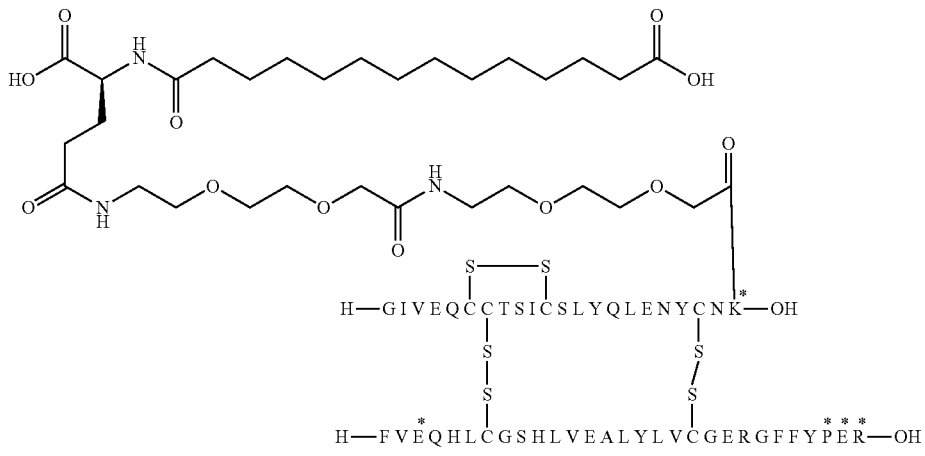

LC-MS (electrospray): m/z=1642.0 (M+4)/4. Calc: 1642.4.

Example 6

General Procedure (A)

A22K(N(eps)tetradecanedioyl-4×gGlu), B3E, B27E, B29R, desB30 Human Insulin; (SEQ ID NOS: 3 and 18)

IUPAC (OpenEye, IUPAC style) name: N{Alpha}([GluB3,GluB27,ArgB29],des-ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]butanoyl]Lys,(B)-peptide.

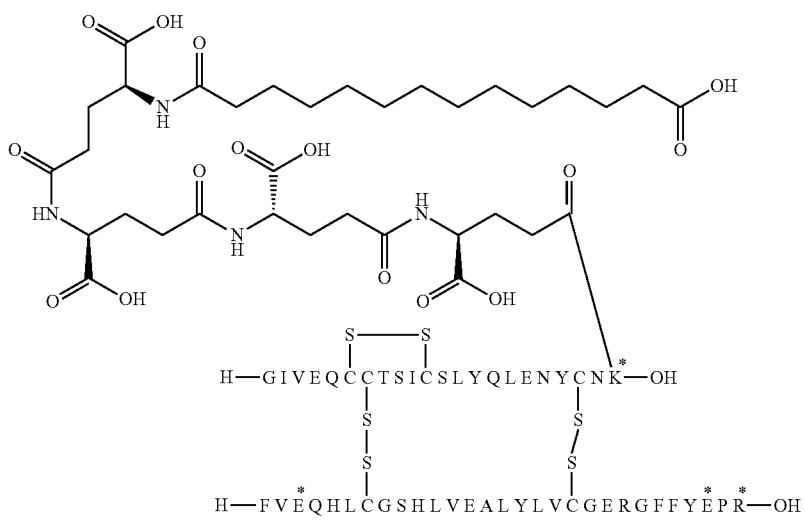

LC-MS (electrospray): m/z=1666.4 (M+4)/4. Calc: 1666.7.

Example 7

General Procedure (A)
A22K(N(eps)tetradecanedioyl-gGlu-2×OEG), B3E, B28D, B29R, desB30 Human Insulin; (SEQ ID NOS: 3 and 20)

IUPAC (OpenEye, IUPAC style) name: N{Alpha}([GluB3,AspB28,ArgB29],des-ThrB30-Insulin(human)-(A)-peptidyl)-N{Epsilon}[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]-acetyl]Lys, (B)-peptide.

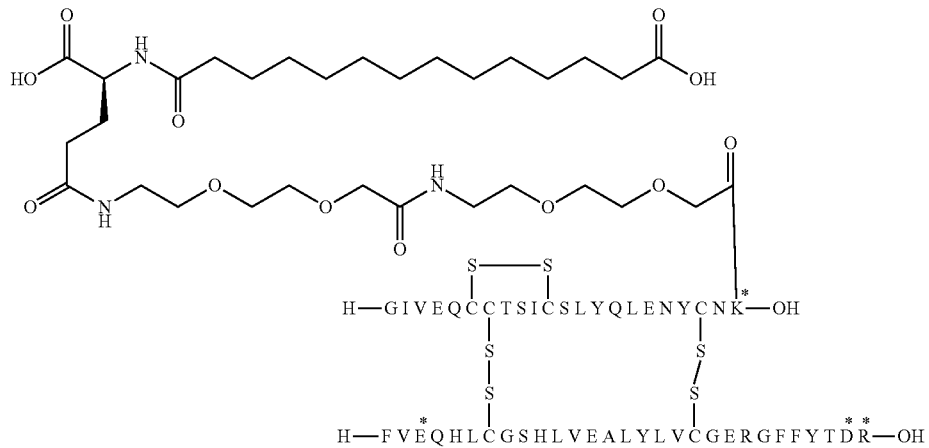

LC-MS (electrospray): m/z=1639.6 (M+4)/4. Calc: 1639.9.

Example 8

General Procedure (B)
A14E, A22K(N(eps)tetradecanedioyl-4×gGlu), B30, B28D, B29R, desB30 Human Insulin; (SEQ ID NOS: 2 and 22)

IUPAC (OpenEye, IUPAC style) name: N{Alpha}([GluA14,GlnB3,AspB28,ArgB29], des-ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]butanoyl]Lys,(B)-peptide.

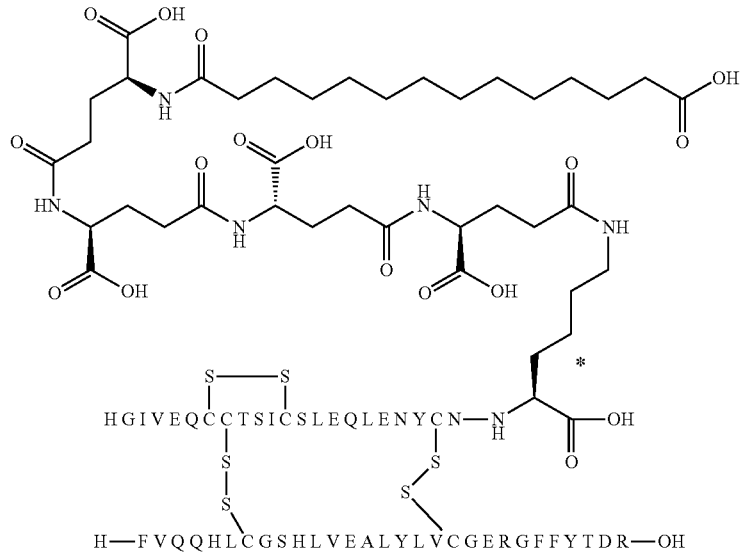

LC-MS (electrospray): m/z=1655.2. (M+4)/4. Calc: 1655.4.

Example 9

General Procedure (B)
A14E, A22K(N(eps)tetradecanedioyl-4×gGlu), B30, B27E, B28E, B29R, desB30 Human Insulin; (SEQ ID NOS: 2 and 19)

IUPAC (OpenEye, IUPAC style) name: N{Alpha}([GluA14,GlnB3,GluB27,GluB28, Arg B29],des-ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino) butanoyl]amino]butanoyl]amino]butanoyl]amino]butanoyl]Lys,(B)-peptide.

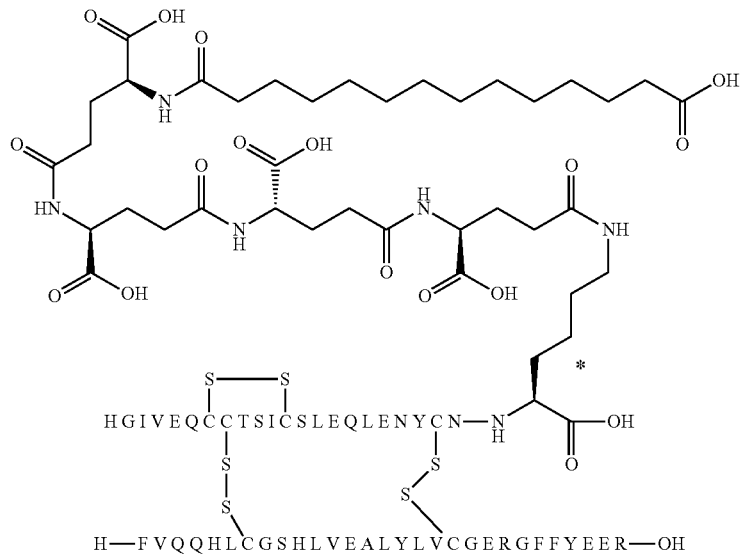

LC-MS (electrospray): m/z=1665.7 (M+4)/4. Calc: 1665.9.

Example 10

General Procedure (A)
A22K(N(eps)tetradecanedioyl-4×gGlu), B3E, B28D, B29R, desB30 Human Insulin; (SEQ ID NOS: 3 and 20)

IUPAC (OpenEye, IUPAC style) name: N{Alpha}([GluB3,AspB28,ArgB29],des-ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]butanoyl]Lys,(B)-peptide.

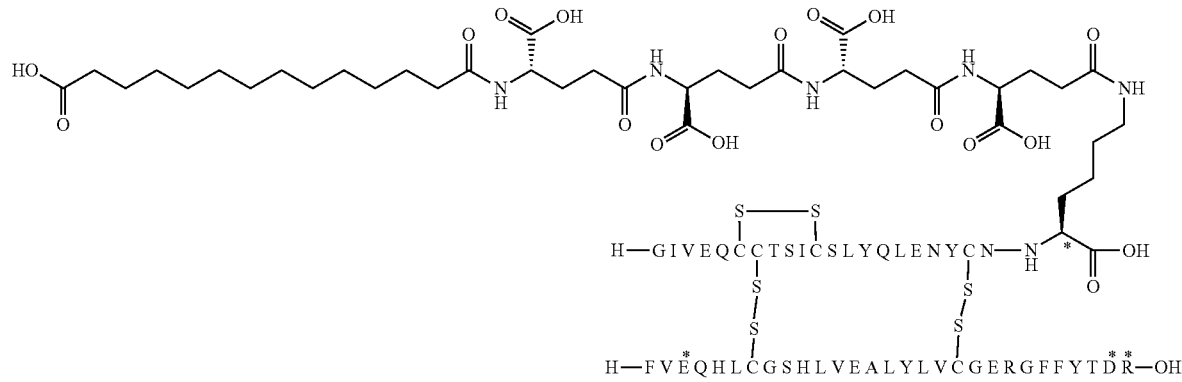

LC-MS (electrospray): m/z=1664.1 (M+4)/4. Calc: 1664.3.

Example 11

General Procedure (A and B)
A22K(N(eps)tetradecanedioyl-4×gGlu), B3E, B26E, B28E, B29R, desB30 Human Insulin; (SEQ ID NOS: 3 and 10)

IUPAC (OpenEye, IUPAC style) name: N{Alpha}([GluB3,GluB26,GluB28,ArgB29],des-ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]butanoyl]Lys,(B)-peptide.

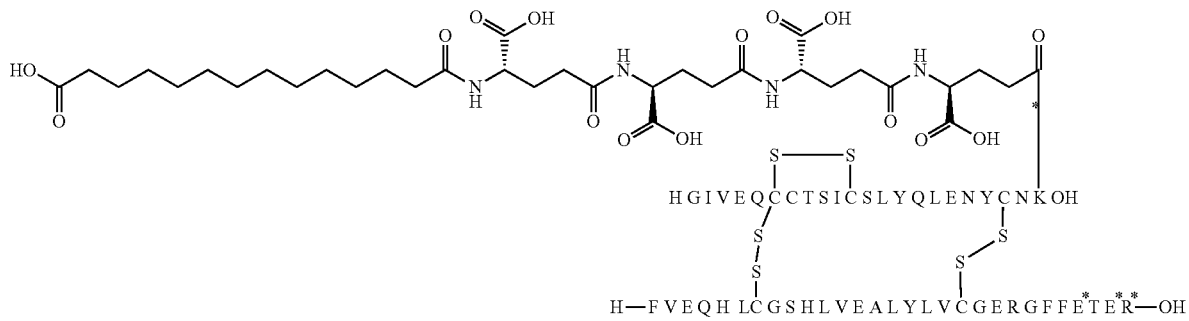

LC-MS (electrospray): m/z=1658.8 (M+4)/4. Calc: 1658.0.

Example 12

General Procedure (A and B)
A22K(N(eps)tetradecanedioyl-4×gGlu), B3E, B26E, B29R, desB30 Human Insulin; (SEQ ID NOS: 3 and 11)

IUPAC (OpenEye, IUPAC style) name: N{Alpha}([GluB3,GluB26,ArgB29],des-ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]butanoyl]Lys,(B)-peptide.

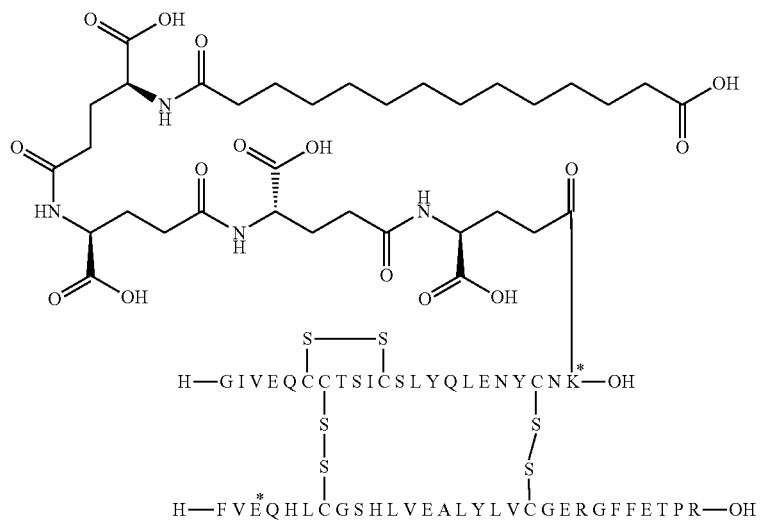

LC-MS (electrospray): m/z=1650.8 (M+4)/4. Calc: 1651.1.

Example 13

General Procedure (B)
A22K(N(eps)tetradecanedioyl-4×gGlu), B3E, B26E, B27P, B28R, desB29, desB30 Human Insulin; (SEQ ID NOS: 3 and 7)
IUPAC (OpenEye, IUPAC style) name: N{Alpha}([GluB3,GluB26,ProB27,ArgB28]-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]butanoyl]Lys,(B1-28)-peptide.

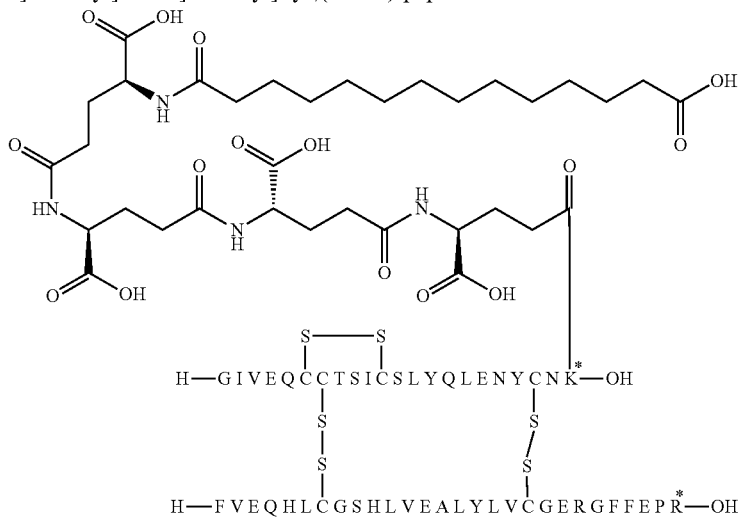

LC-MS (electrospray): m/z=1625.7 (M+4)/4. Calc: 1625.7.

Example 14

General Procedure (B)
A22K(N(eps)tetradecanedioyl-4×gGlu), B3E, B27E, B28R, desB29, desB30 Human Insulin; (SEQ ID NOS: 3 and 14)
IUPAC (OpenEye, IUPAC style) name: N{Alpha}([GluB3,GluB27,ArgB28]-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]butanoyl]Lys,(B1-B28)-peptide.

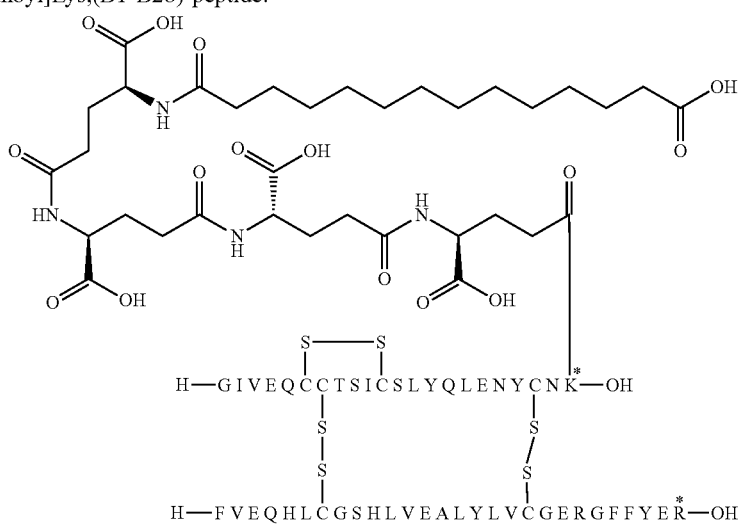

LC-MS (electrospray): m/z=1642.2 (M+4)/4. Calc: 1642.3.

Example 15

General Procedure (B)
A8R, A22K(N(eps)tetradecanedioyl-4xgGlu), B3E, B26E, B29R, desB30 Human Insulin; (SEQ ID NOS: 1 and 11)

IUPAC (OpenEye, IUPAC style) name: N{Alpha}([ArgA8,GluB3,GluB26,ArgB29],des-ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]-butanoyl]amino]butanoyl]amino]butanoyl]Lys,(B)-peptide.

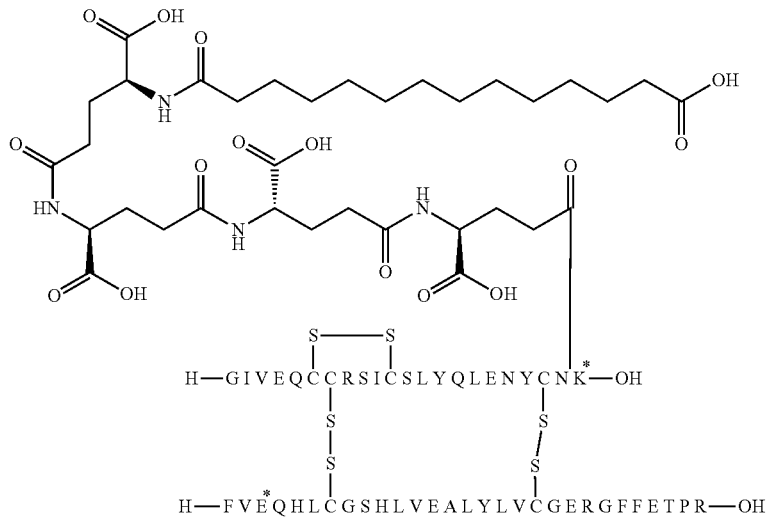

LC-MS (electrospray): m/z=1664.6 (M+4)/4. Calc: 1664.9.

Example 16

General Procedure (B)
A8R, A22K(N(eps)tetradecanedioyl-4xgGlu), B3E, B26E, B27P, B28R, desB29, desB30 Human Insulin; (SEQ ID NOS: 1 and 7)

IUPAC (OpenEye, IUPAC style) name: N{Alpha}([ArgA8,GluB3,GluB27,ArgB28]-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]butanoyl]-amino]butanoyl]amino]butanoyl]Lys,(B1-28)-peptide.

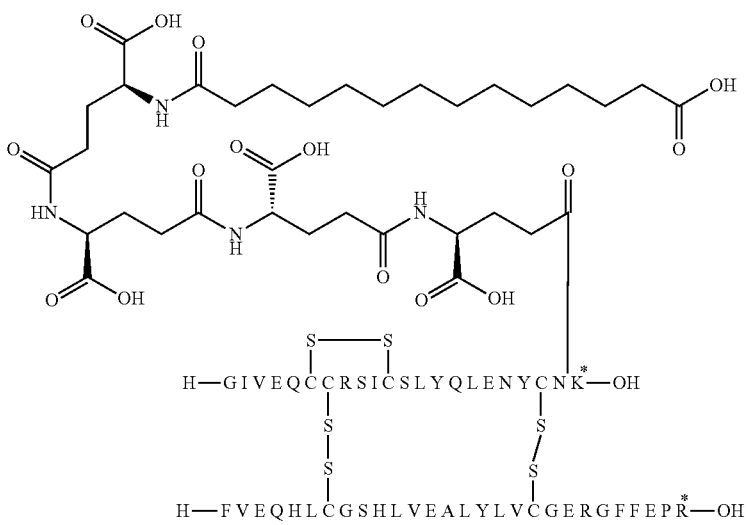

LC-MS (electrospray): m/z=1639.4 (M+4)/4. Calc: 1639.6.

Example 17

General Procedure (B)
A8R, A22K(N(eps)tetradecanedioyl-4×gGlu), B3E, B27E, B28R, desB29, desB30 Human Insulin; (SEQ ID NOS: 1 and 14)

IUPAC (OpenEye, IUPAC style) name: N{Alpha}([ArgA8,GluB3,GluB27,ArgB28]-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]butanoyl]Lys,(B1-B28)-peptide.

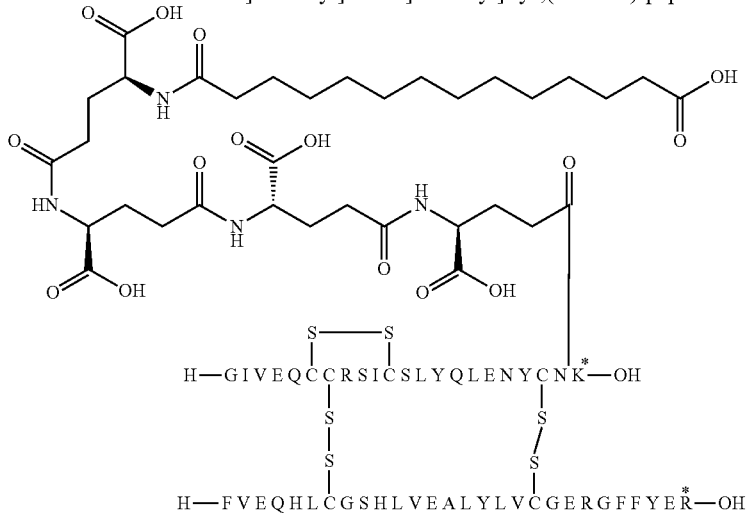

LC-MS (electrospray): m/z=1655.7 (M+4)/4. Calc: 1656.1.

Example 18

General Procedure (B)
A22K(N(eps)tetradecanedioyl-4×gGlu), B3E, B26E, B27E, B28R, desB29, desB30 Human Insulin; (SEQ ID NOS: 3 and 5)

IUPAC (OpenEye, IUPAC style) name: N{Alpha}([GluB3,GluB26,GluB27,ArgB28]-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]butanoyl]Lys,(B1-B28)-peptide.

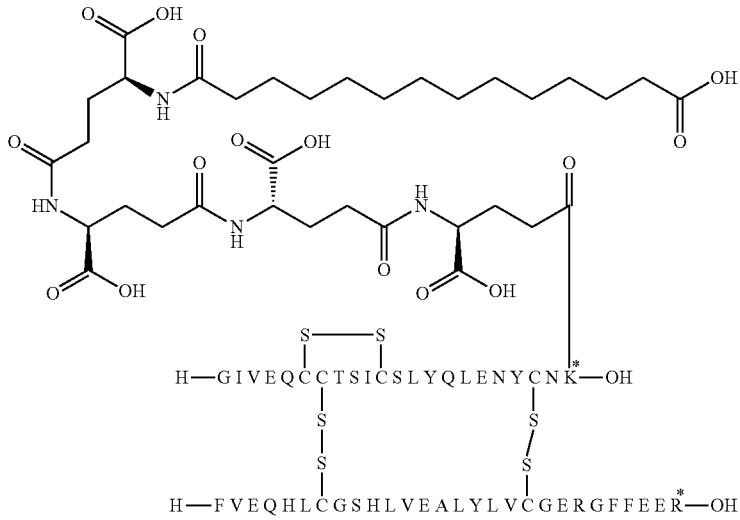

LC-MS (electrospray): m/z=1633.8 (M+4)/4. Calc: 1633.8.

Example 19

General Procedure (B)
A8R, A22K(N(eps)tetradecanedioyl-4xgGlu), B3E, B26E, B27E, B28R, desB29, desB30 Human Insulin; (SEQ ID NOS: 1 and 5)

IUPAC (OpenEye, IUPAC style) name: N{Alpha}([ArgA8,GluB3,GluB26,GluB27, ArgB28]-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]butanoyl]-amino]butanoyl]amino]butanoyl]Lys,(B1-B28)-peptide.

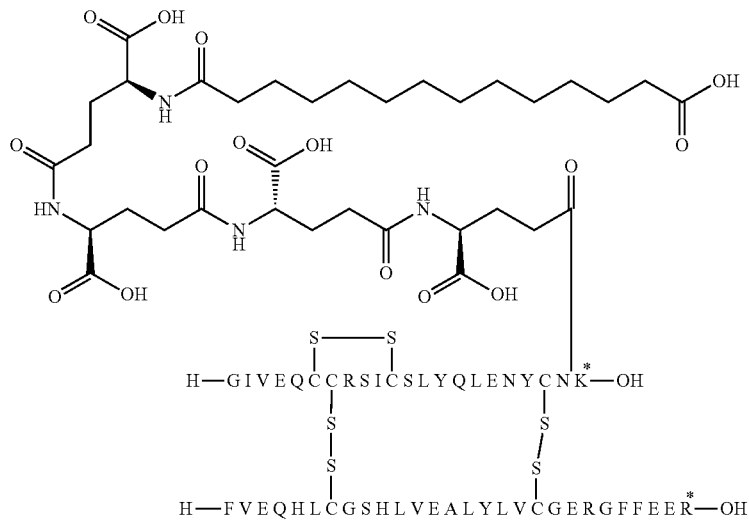

LC-MS (electrospray): m/z=1647.5 (M+4)/4. Calc: 1647.6.

Example 20

General Procedure (A and B)
A22K(N(eps)tetradecanedioyl-4xgGlu), B3E, B28E, B29P, B30R Human Insulin; (SEQ ID NOS: 3 and 21)

IUPAC (OpenEye, IUPAC style) name: N{Alpha}([GluB3,GluB28,ProB29,ArgB30]-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]butanoyl]-amino]butanoyl]amino]butanoyl]Lys,(B)-peptide.

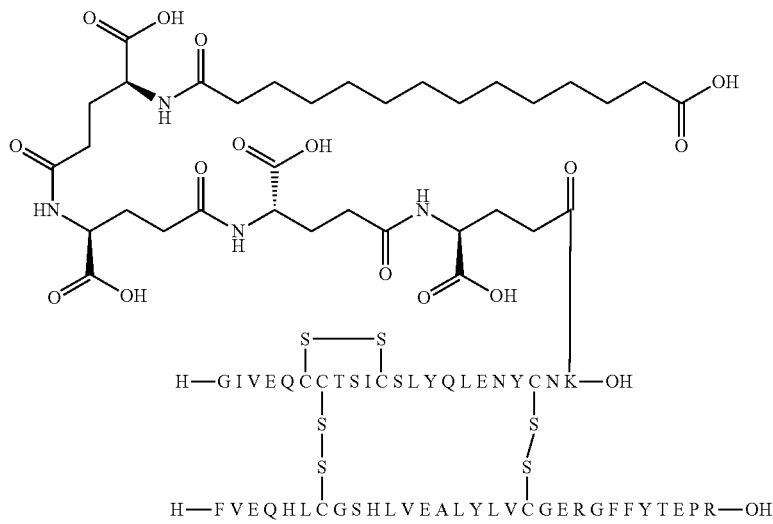

LC-MS (electrospray): m/z=1691.9 (M+4)/4. Calc: 1691.8.

Example 21

General Procedure (B)
A22K(N(eps)tetradecanedioyl-4×gGlu), B3E, B26E, B28E, B29P, B30R Human Insulin; (SEQ ID NOS: 3 and 9)

IUPAC (OpenEye, IUPAC style) name: N{Alpha}([GluB3,GluB26,GluB28,ProB29, ArgB30]-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]butanoyl]Lys,(B)-peptide.

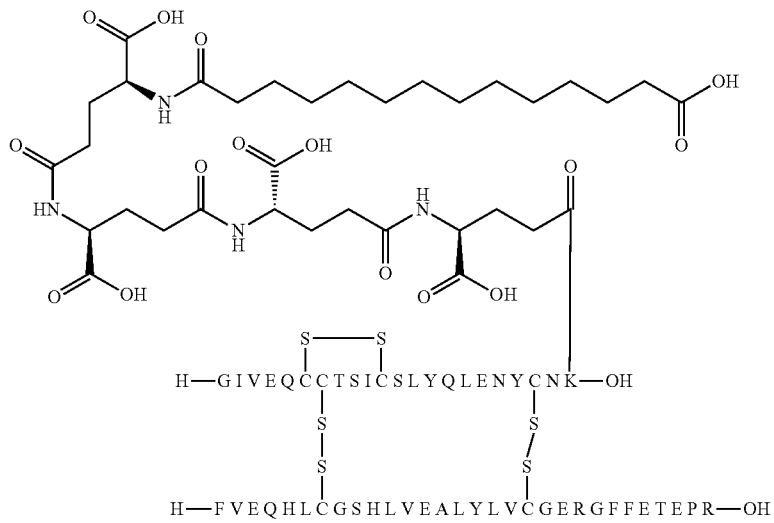

LC-MS (electrospray): m/z=1683.3 (M+4)/4. Calc: 1683.4.

Example 22

General Procedure (B)
A22K(N(eps)tetradecanedioyl-4×gGlu), B3E, B27E, B28E, B29P, B30R Human Insulin; (SEQ ID NOS: 3 and 15)

IUPAC (OpenEye, IUPAC style) name: N{Alpha}([GluB3,GluB27,GluB28,ProB29, ArgB30]-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]-butanoyl]amino]butanoyl]amino]butanoyl]Lys,(B)-peptide.

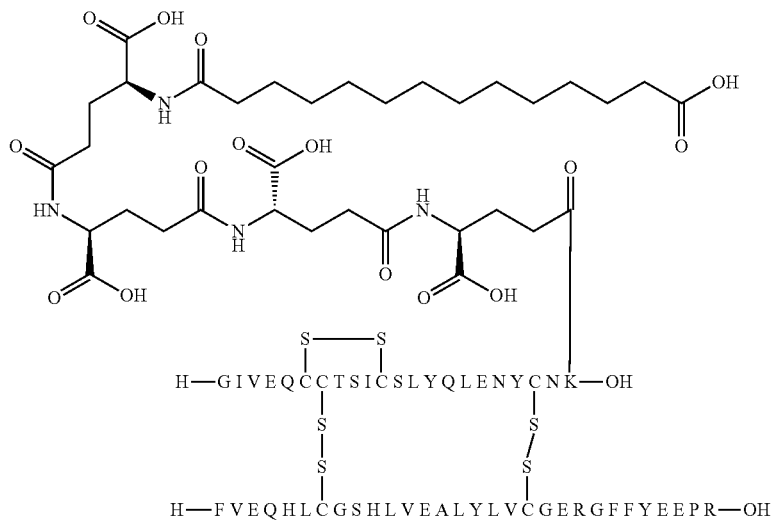

LC-MS (electrospray): m/z=1698.7 (M+4)/4. Calc: 1698.9.

Example 23

General Procedure (B)
A8R, A22K(N(eps)tetradecanedioyl-4×gGlu), B3E, B26E, B28E, B29R, desB30 Human Insulin; (SEQ ID NOS: 1 and 10)

IUPAC (OpenEye, IUPAC style) name: N{Alpha}([ArgA8,GluB3,GluB26,GluB28, Arg B29],des-ThrB30-Insulin(human)-(A)-peptidyl)-N {Epsilon}[(4S)-4-carboxy-4-[[(4S)-4-carboxy-4-[[(4S)-4-carboxy-4-[[(4S)-4-carboxy-4-(13-carboxytridecanoylamino) butanoyl]amino]butanoyl]amino]butanoyl]amino]butanoyl]Lys,(B)-peptide.

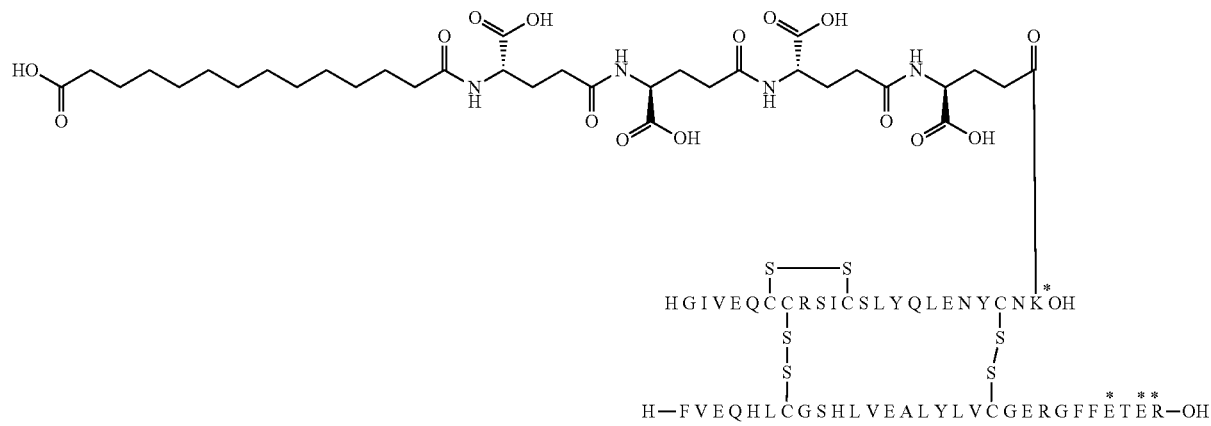

LC-MS (electrospray): m/z=1672.6 (M+4)/4. Calc: 1672.9.

Example 24

General Procedure (B)
A8R, A22K(N(eps)tetradecanedioyl-4×gGlu), B3E, B27E, B28E, B29R, desB30 Human Insulin; (SEQ ID NOS: 1 and 16)

IUPAC (OpenEye, IUPAC style) name: N{Alpha}([ArgA8,GluB3,GluB27,GluB28, Arg B29],des-ThrB30-Insulin(human)-(A)-peptidyl)-N {Epsilon}[(4S)-4-carboxy-4-[[(4S)-4-carboxy-4-[[(4S)-4-carboxy-4-[[(4S)-4-carboxy-4-(13-carboxytridecanoylamino) butanoyl]amino]butanoyl]amino]butanoyl]amino]butanoyl]Lys,(B)-peptide.

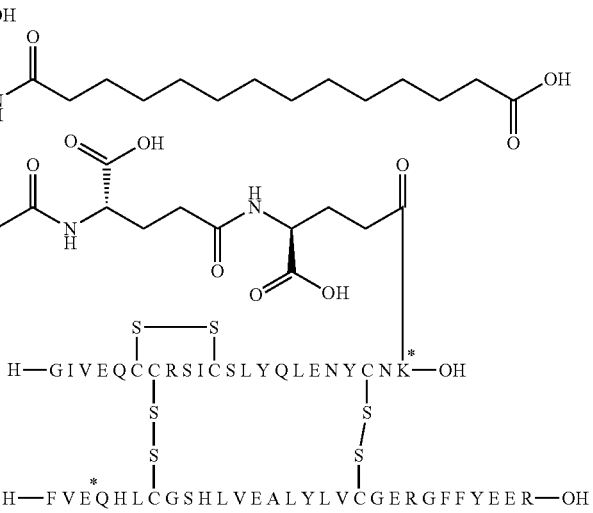

LC-MS (electrospray): m/z=1688 (M+4)/4. Calc: 1688.3.

Example 25

General Procedure (A)
A22K(N(eps)Hexadecanedioyl-gGlu-2×OEG), B3E, B27E, B29R, desB30 Human Insulin; (SEQ ID NOS: 3 and 18)

IUPAC (OpenEye, IUPAC style) name: N{Alpha}([GluB3,GluB27,ArgB29],des-ThrB30-Insulin(human)-(A)-peptidyl)-N{Epsilon}[2-[2-[2-[[2-[2-[2-[[(4S)-4-carboxy-4-(15-carboxypentadecanoylamino) butanoyl]amino]ethoxy]ethoxy]acetyl]amino]ethoxy]-ethoxy]acetyl]Lys,(B)-peptide.

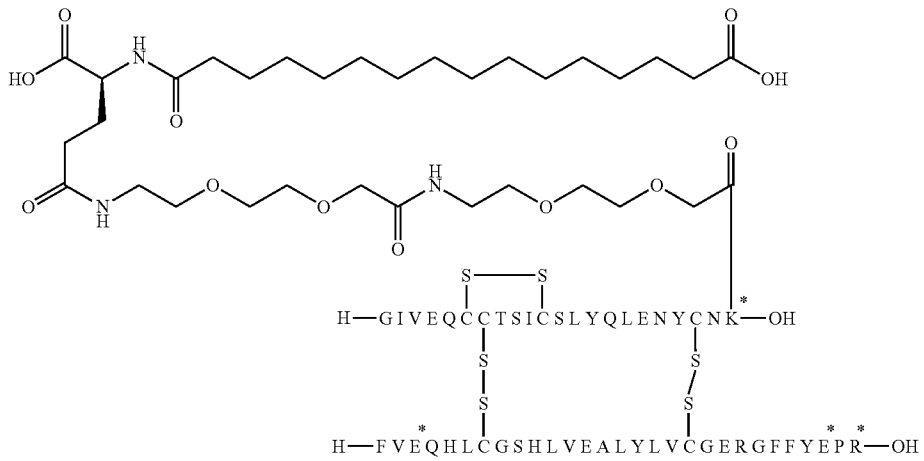

LC-MS (electrospray): m/z=1649.3 (M+4)/4. Calc: 1649.4.

Example 26

General Procedure (A)
A14E, A22K(N(eps)hexadecanedioyl-gGlu-2×OEG), B3E, B27E, B28E, B29R, desB30 Human Insulin; (SEQ ID NOS: 2 and 16)

IUPAC (OpenEye, IUPAC style) name: N{Alpha}([GluA14,GluB3,GluB27,GluB28, ArgB29],des-ThrB30-Insulin(human)-(A)-peptidyl)-N{Epsilon}[2-[2-[2-[[2-[2-[2-[[(4S)-4-carboxy-4-(15-carboxypentadecanoylamino) butanoyl]amino]ethoxy]ethoxy]acetyl]amino]ethoxy]ethoxy]acetyl]Lys,(B)-peptide.

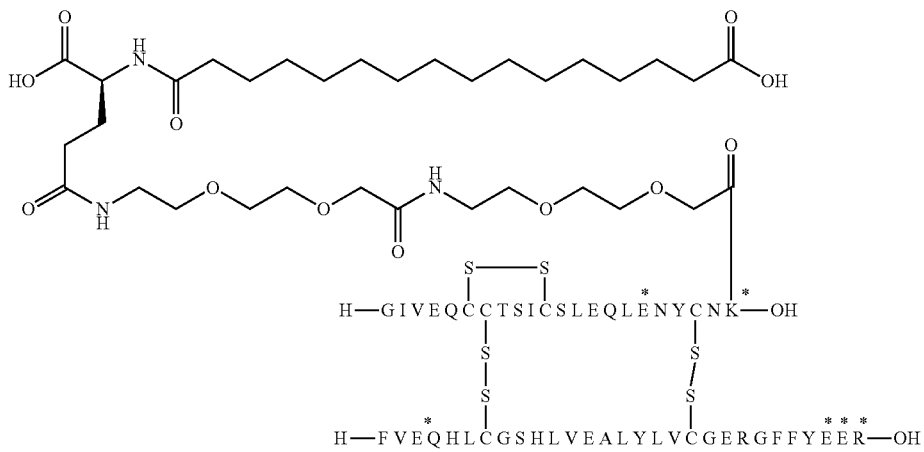

LC-MS (electrospray): m/z=1648.7 (M+4)/4. Calc: 1647.8

Example 27

General Procedure (A)
A14E, A22K(N(eps)hexadecanedioyl-4×gGlu), B3E, B27E, B28E, B29R, desB30 Human Insulin; (SEQ ID NOS: 2 and 16)
IUPAC (OpenEye, IUPAC style) name: N{Alpha}([GluA14,GluB3,GluB27,GluB28, Arg B29],des-ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(15-carboxypentadecanoylamino) butanoyl]amino]butanoyl]amino]butanoyl]amino]butanoyl]Lys,(B)-peptide.

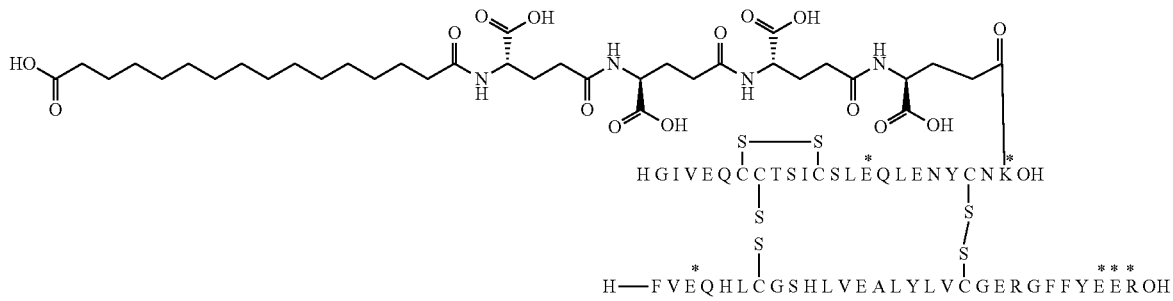

LC-MS (electrospray): m/z=1672.7 (M+4)/4. Calc: 1672.0

Example 28

General Procedure (A)
A22K(N(eps)hexadecanedioyl-4×gGlu), B3E, B27E, B28E, B29R, desB30 Human Insulin; (SEQ ID NOS: 3 and 16)
IUPAC (OpenEye, IUPAC style) name: N{Alpha}([GluB3,GluB27,GluB28,ArgB29],des-ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(15-carboxypentadecanoylamino) butanoyl]-amino]butanoyl]amino]butanoyl]amino]butanoyl]Lys,(B)-peptide.

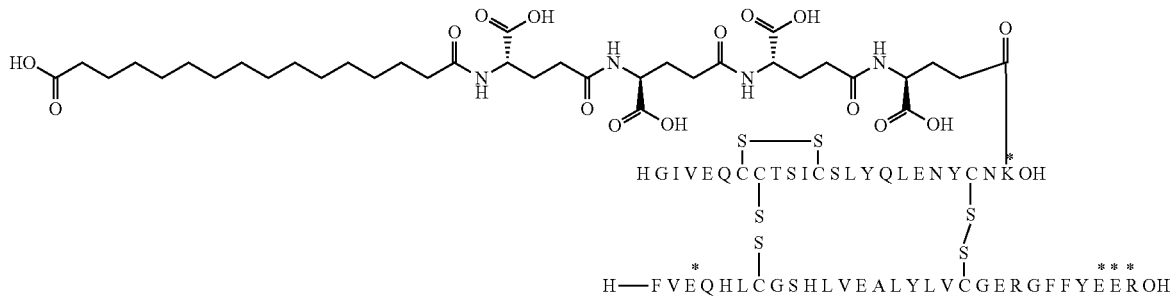

LC-MS (electrospray): m/z=1681.3 (M+4)/4. Calc: 1680.5.

Example 29

General Procedure (A)
A22K(N(eps)hexadecanedioyl-gGlu-2×OEG), B3E, B27P, B28E, B29R, desB30 Human Insulin; (SEQ ID NOS: 3 and 17)
IUPAC (OpenEye, IUPAC style) name: N{Alpha}([GluB3,ProB27,GluB28, ArgB29],des-ThrB30-Insulin(human)-(A)-peptidyl)-N{Epsilon}[2-[2-[2-[[2-[2-[2-[[(4S)-4-carboxy-4-(15-carboxypentadecanoylamino)butanoyl]amino]ethoxy]ethoxy]acetyl]amino]ethoxy]-ethoxy]acetyl]Lys,(B)-peptide.

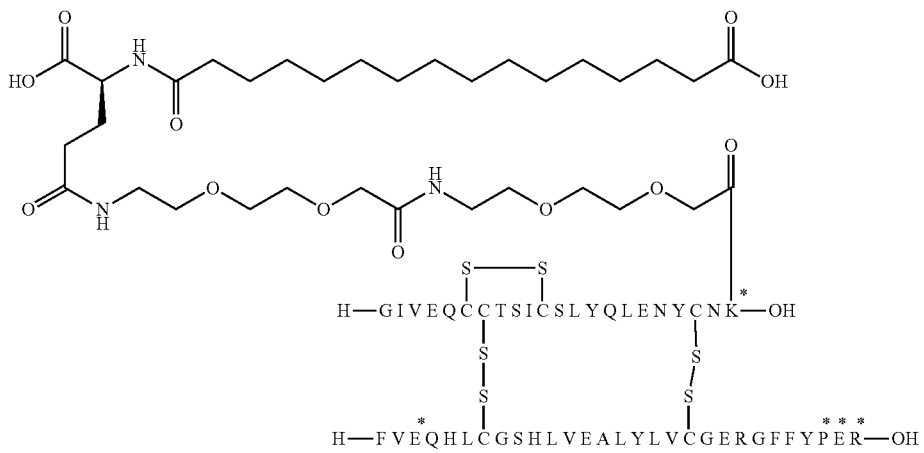

LC-MS (electrospray): m/z=1649.3 (M+4)/4. Calc: 1649.4.

Example 30

General Procedure (A)

A22K(N(eps)hexadecanedioyl-4×gGlu), B3E, B27P, B28E, B29R, desB30 Human Insulin; (SEQ ID NOS: 3 and 17)

IUPAC (OpenEye, IUPAC style) name: N{Alpha}([GluB3,ProB27,GluB28, ArgB29],des-ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(15-carboxypentadecanoylamino) butanoyl]amino]butanoyl]amino]butanoyl]amino]butanoyl]Lys,(B)-peptide.

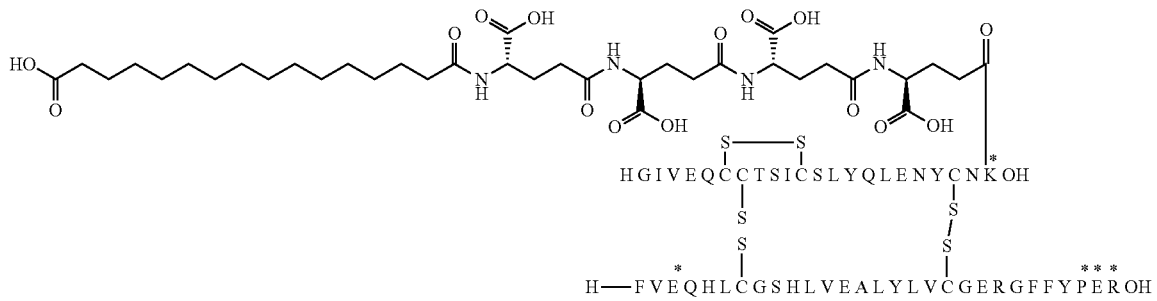

LC-MS (electrospray): m/z=1673.5 (M+4)/4. Calc: 1673.7.

Example 31

General Procedure (A)

A22K(N(eps)hexadecanedioyl-gGlu-2×OEG), B3E, B27E, B28E, B29R, desB30 Human Insulin; (SEQ ID NOS: 3 and 16)

IUPAC (OpenEye, IUPAC style) name: N{Alpha}([GluB3,GluB27,GluB28, ArgB29],des-ThrB30-Insulin(human)-(A)-peptidyl)-N{Epsilon}[2-[2-[2-[[2-[2-[2-[[(4S)-4-carboxy-4-(15-carboxypentadecanoylamino)butanoyl]amino]ethoxy]ethoxy]acetyl]amino]ethoxy]-ethoxy]acetyl]Lys,(B)-peptide.

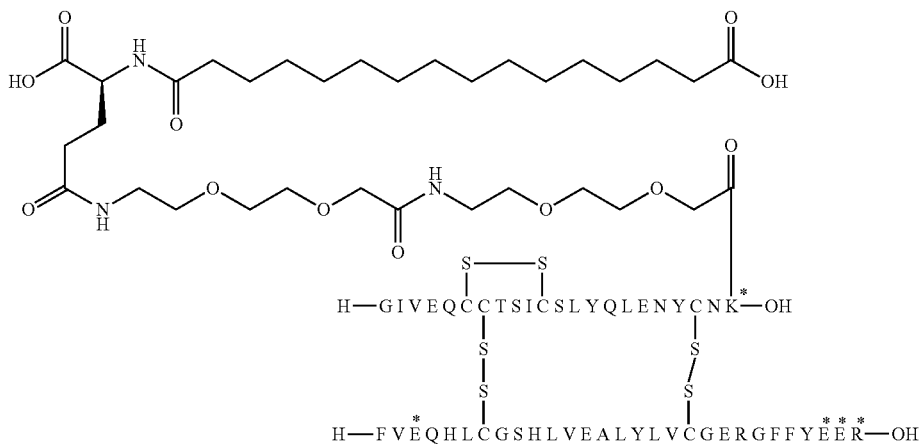

LC-MS (electrospray): m/z=1657.2 (M+4)/4. Calc: 1656.3.

Example 32

General Procedure (A)
A22K(N(eps)hexadecanedioyl-4×gGlu), B3E, B27E, B29R, desB30 Human Insulin; (SEQ ID NOS: 3 and 18)
IUPAC (OpenEye, IUPAC style) name: N{Alpha}([GluB3,GluB27,ArgB29],des-ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(15-carboxypentadecanoylamino)butanoyl]amino]-butanoyl]amino]butanoyl]amino]butanoyl]Lys,(B)-peptide.

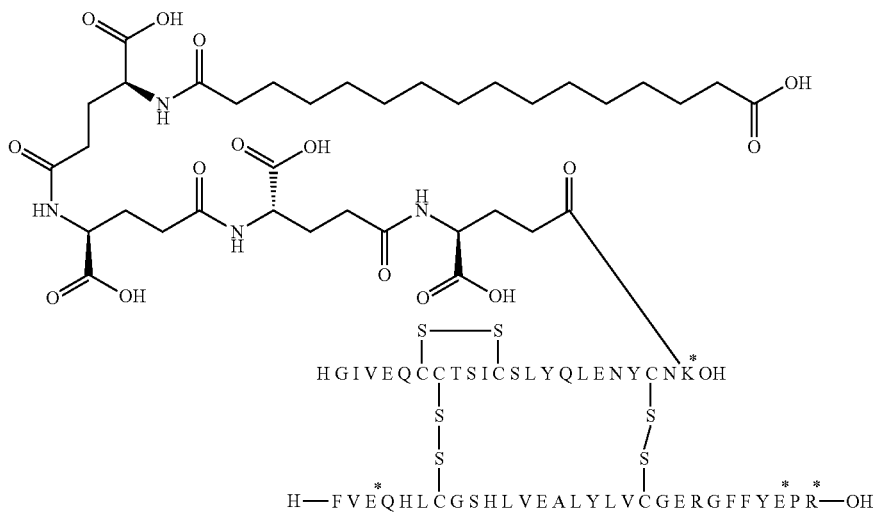

LC-MS (electrospray): m/z=1673.4 (M+4)/4. Calc: 1673.7.

Example 33

General Procedure (A)
A22K(N(eps)hexadecanedioyl-gGlu-2×OEG), B3E, B28D, B29R, desB30 Human Insulin; (SEQ ID NOS: 3 and 20)
IUPAC (OpenEye, IUPAC style) name: N{Alpha}([GluB3,AspB28,ArgB29],des-ThrB30-Insulin(human)-(A)-peptidyl)-N{Epsilon}[2-[2-[2-[[2-[2-[2-[[(4S)-4-carboxy-4-(15-carboxypentadecanoylamino) butanoyl]amino] ethoxy]ethoxy]acetyl]amino]ethoxy]ethoxy]acetyl]Lys,(B)-peptide.

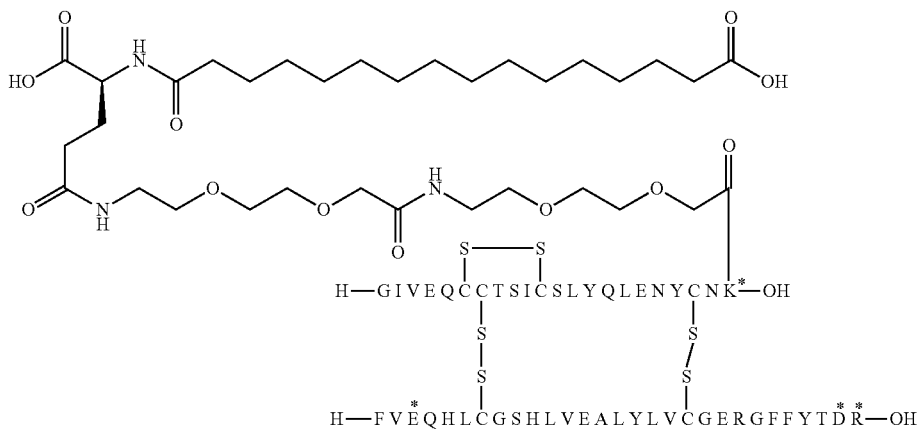

LC-MS (electrospray): m/z=1647.2 (M+4)/4. Calc: 1647.4.

Example 34

May be Prepared According to General Procedure (A or B)

A22K(N(eps)tetradecanedioyl-4xgGlu), B3E, B26E, B28D, B29R, desB30 Human Insulin; (SEQ ID NOS: 3 and 8)

IUPAC (OpenEye, IUPAC style) name: N{Alpha}([GluB3,GluB26,AspB28,ArgB29],des-ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]butanoyl]Lys,(B)-peptide.

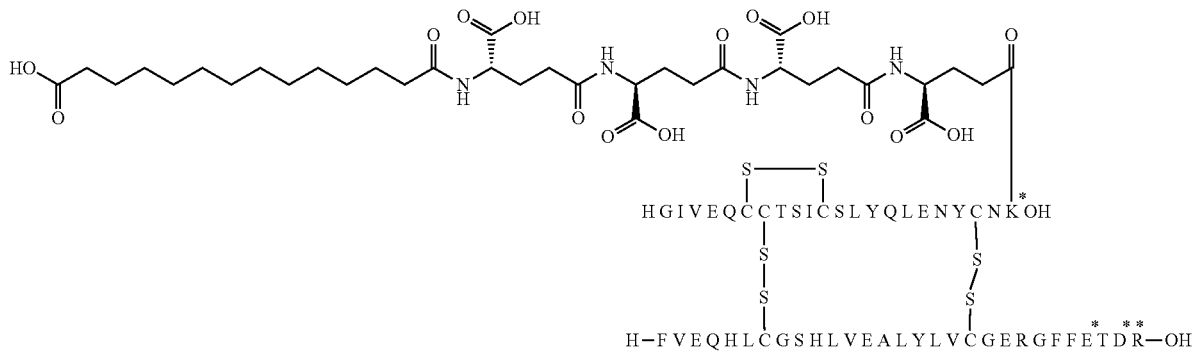

Example 35

May be Prepared According to General Procedure (A or B)

A22K(N(eps)tetradecanedioyl-4xgGlu), B3E, B26E, B27E, B29P, B30R Human Insulin; (SEQ ID NOS: 3 and 6)

IUPAC (OpenEye, IUPAC style) name: N{Alpha}([GluB3,GluB26,GluB27,GluB28,ProB29, ArgB30]-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]butanoyl]Lys,(B)-peptide.

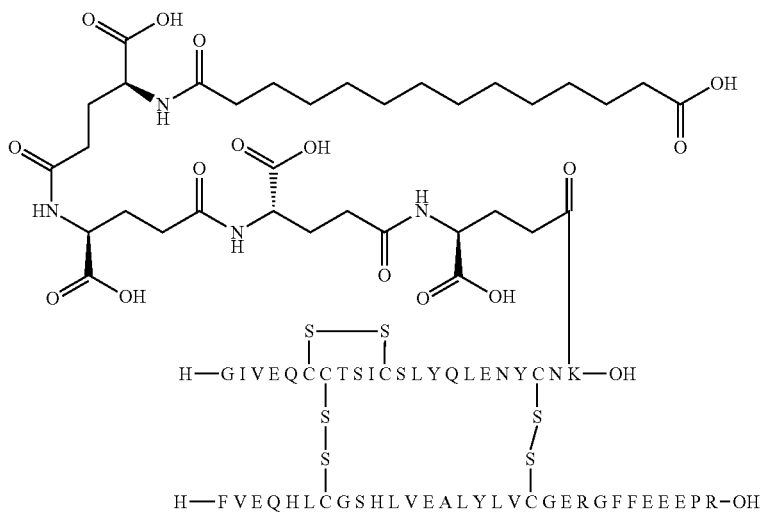

Example 36

General Procedure (B)
A22K(N(eps)tetradecanedioyl-4×gGlu), B3E, B26E, B27E, B28E, B29R, desB30 Human Insulin; (SEQ ID NOS: 3 and 4)

IUPAC (OpenEye, IUPAC style) name: N{Alpha}([GluB3,GluB26,GluB27,GluB28,ArgB29], des-ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino) butanoyl]amino]butanoyl]amino]butanoyl]amino]butanoyl]Lys,(B)-peptide.

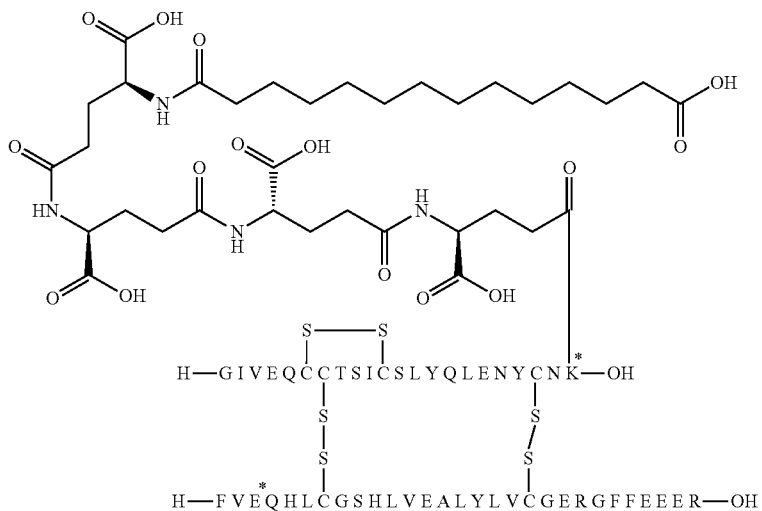

LC-MS (electrospray): m/z=1666.0 (M+4)/4. Calc: 1666.1

Example 37

General procedure (A)
A22K(N(eps)hexadecanedioyl-4×gGlu), B3E, B28D, B29R, desB30 Human Insulin; (SEQ ID NOS: 3 and 4)

IUPAC (OpenEye, IUPAC style) name: N{Alpha}([GluB3,AspB28,ArgB29],des-ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(15-carboxypentadecanoylamino)butanoyl]amino]-butanoyl]amino]butanoyl]amino]butanoyl]Lys,(B)-peptide.

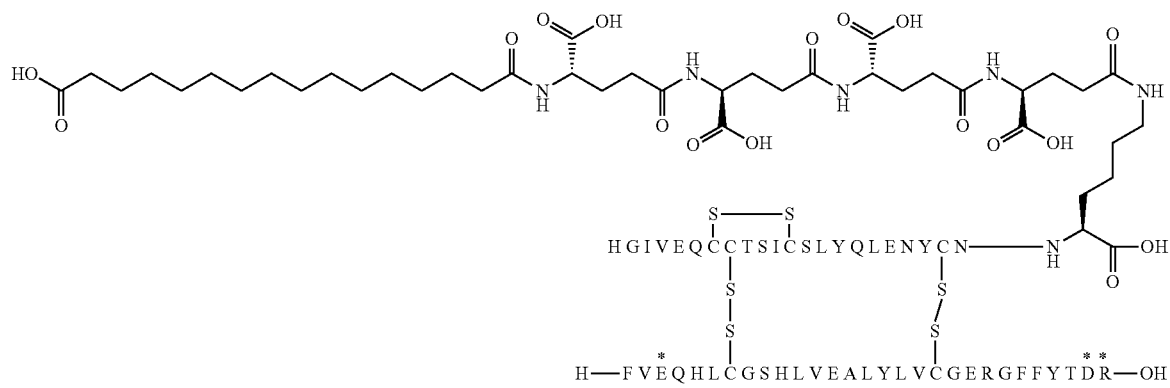

LC-MS (electrospray): m/z=1671.1 (M+4)/4. Calc: 1671.1

Example 38

General Procedure (A)
A22K(N(eps)tetradecanedioyl-4×gGlu), B3E, B27P, B28E, B29R, desB30 Human Insulin; (SEQ ID NOS: 3 and 17)

IUPAC (OpenEye, IUPAC style) name: N{Alpha}([GluB3,ProB27,GluB28,ArgB29],des-ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]butanoyl]Lys,(B)-peptide.

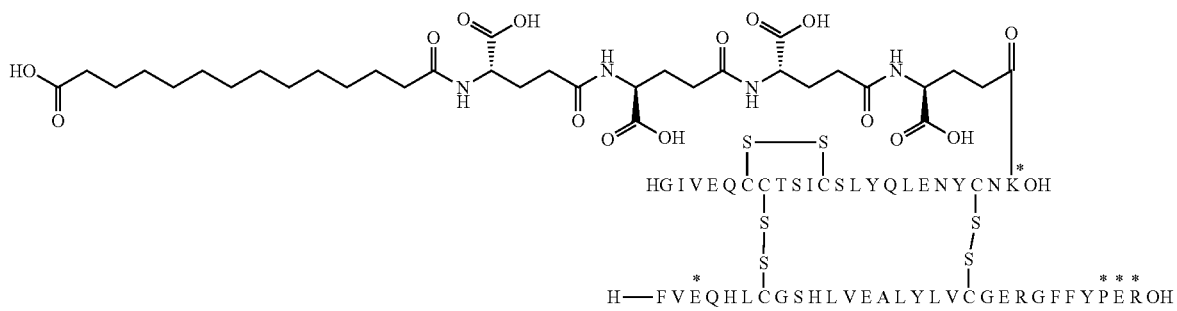

LC-MS (electrospray): m/z=1666.4 (M+4)/4. Calc: 1666.7

Example 39

General Procedure (A)
A22K(N(eps)tetradecanedioyl-4×gGlu), B30, B26E, B29R, desB30 Human Insulin; (SEQ ID NOS: 3 and 12)

IUPAC (OpenEye, IUPAC style) name: N{Alpha}([GlnB3,GluB26,ArgB29],des-ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]butanoyl]Lys,(B)-peptide.

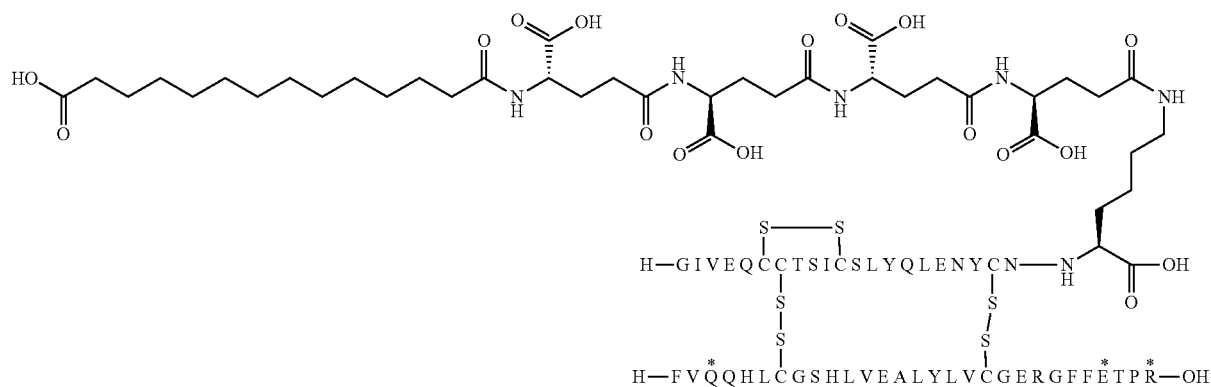

LC-MS (electrospray): m/z=1650.9 (M+4)/4. Calc: 1650.8

Example 40

General Procedure (A)
A22K(N(eps)tetradecanedioyl-4×gGlu), B30, B26E, B28E, B29R, desB30 Human Insulin; (SEQ ID NOS: 3 and 13)

IUPAC (OpenEye, IUPAC style) name: N{Alpha}([GlnB3,GluB26,GluB28,ArgB29],des-ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]-butanoyl]amino]butanoyl]amino]butanoyl]Lys,(B)-peptide.

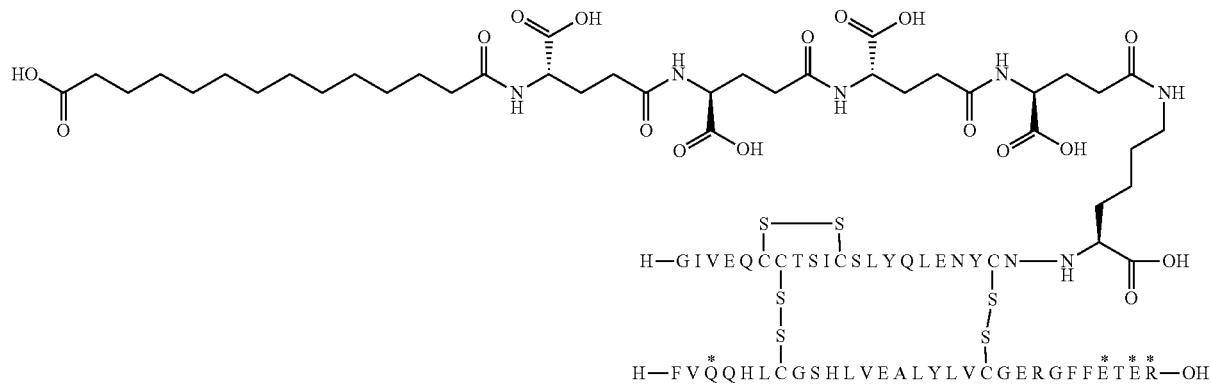

LC-MS (electrospray): m/z=1658.7 (M+4)/4. Calc: 1658.9

Example 41

General Procedure (A)
A22K(N(eps)hexadecanedioyl-4×gGlu), B3E, B26E, B29R, desB30 Human Insulin; (SEQ ID NOS: 3 and 11)

IUPAC (OpenEye, IUPAC style) name: N{Alpha}([GluB3,GluB26,ArgB29],des-ThrB30-Insulin-(A)-peptidyl)-N{Epsilon}[(4S)-4-carboxy-4-[[(4S)-4-carboxy-4-[[(4S)-4-carboxy-4-[[(4S)-4-carboxy-4-(15-carboxypentadecanoylamino)butanoyl]amino]-butanoyl]amino]butanoyl]amino]butanoyl]Lys,(B)-peptide.

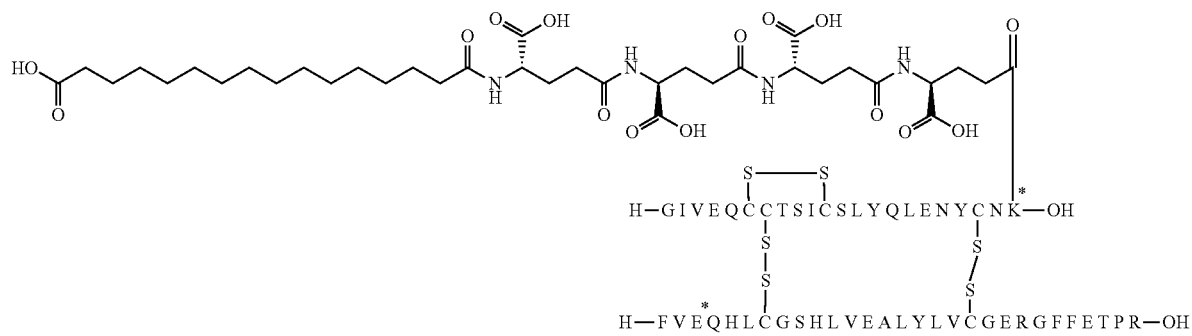

LC-MS (electrospray): m/z=1658.1 (M+4)/4. Calc: 1658.1

Example 42

General Procedure (A)
A22K(N(eps)hexadecanedioyl-gGlu-2×OEG), B3E, B26E, B29R, desB30 Human Insulin; (SEQ ID NOS: 3 and 11)

IUPAC (OpenEye, IUPAC style) name: N{Alpha}([GluB3,GluB26,ArgB29],des-ThrB30-Insulin-(A)-peptidyl)-N{Epsilon}[2-[2-[2-[[2-[2-[2-[[(4S)-4-carboxy-4-(15-carboxy-pentadecanoylamino)butanoyl]amino]ethoxy]ethoxy]acetyl]amino]ethoxy]ethoxy]-acetyl]Lys,(B)-peptide.

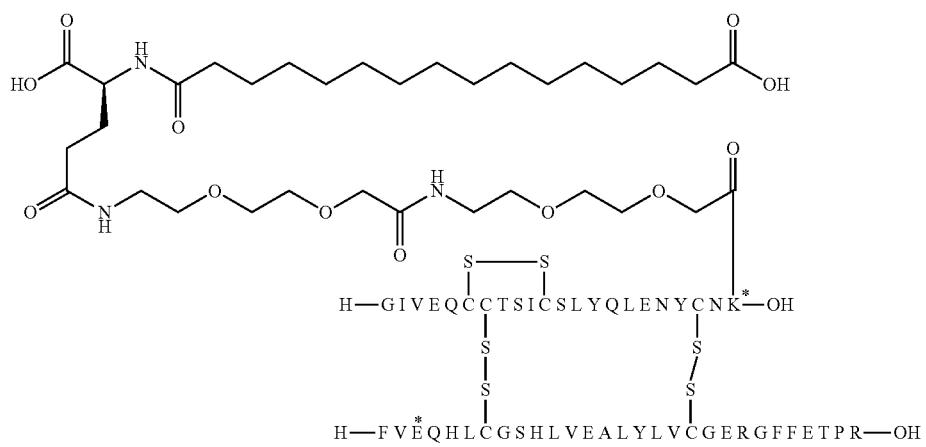

LC-MS (electrospray): m/z=1633.9 (M+4)/4. Calc: 1633.9

Example 43

General Procedure (A)
A22K(N(eps)hexadecanedioyl-gGlu-4×OEG), B3E, B26E, B29R, desB30 Human Insulin; (SEQ ID NOS: 3 and 11)

IUPAC (OpenEye, IUPAC style) name: N{Alpha}([GluB3,GluB26,ArgB29],des-ThrB30-Insulin-(A)-peptidyl)-N{Epsilon}[2-[2-[2-[[2-[2-[2-[[2-[2-[2-[[2-[2-[2-[[(4S)-4-carboxy-4-(15-carboxypentadecanoylamino)butanoyl]amino]ethoxy]ethoxy]acetyl]-amino]ethoxy]ethoxy]acetyl]amino]ethoxy]ethoxy]acetyl]amino]ethoxy]ethoxy]-acetyl]Lys,(B)-peptide.

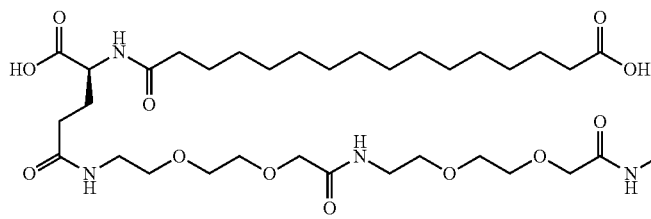

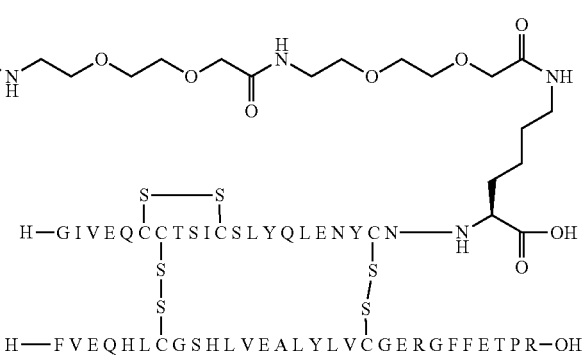

LC-MS (electrospray): m/z=1706.5 (M+4)/4. Calc: 1706.4

Example 44

General Procedure (A)
A22K(N(eps)hexadecanedioyl-gGlu-6×OEG), B3E, B26E, B29R, desB30 Human Insulin; (SEQ ID NOS: 3 and 11)

IUPAC (OpenEye, IUPAC style) name: N{Alpha}([GluB3,GluB26,ArgB29],des-ThrB30-Insulin-(A)-peptidyl)-N{Epsilon}[2-[2-[2-[[2-[2-[2-[[2-[2-[2-[[2-[2-[2-[[2-[2-[2-[[2-[2-[[(4S)-4-carboxy-4-(15-carboxypentadecanoylamino)butanoyl]amino]ethoxy]ethoxy]-acetyl]amino]ethoxy]ethoxy]acetyl]amino]ethoxy]ethoxy]acetyl]amino]ethoxy]ethoxy]-acetyl]amino]ethoxy]ethoxy]acetyl]amino]ethoxy]ethoxy]acetyl]Lys,(B)-peptide.

LC-MS (electrospray): m/z=1779.1 (M+4)/4. Calc: 1779.0

Example 45

General Procedure (A)
A22K(N(eps)hexadecanedioyl-4×gGlu-2×OEG), B3E, B26E, B29R, desB30 Human Insulin; (SEQ ID NOS: 3 and 11)

IUPAC (OpenEye, IUPAC style) name: N{Alpha}([GluB3,GluB26,ArgB29],des-ThrB30-Insulin-(A)-peptidyl)-N{Epsilon}[2-[2-[2-[[2-[2-[2-[[(4S)-4-carboxy-4-[[(4S)-4-carboxy-4-[[(4S)-4-carboxy-4-[[(4S)-4-carboxy-4-(15-carboxypentadecanoylamino)butanoyl]amino]butanoyl]amino]butanoyl]amino]butanoyl]amino]ethoxy]ethoxy]acetyl]amino]ethoxy]ethoxy]acetyl]-Lys,(B)-peptide.

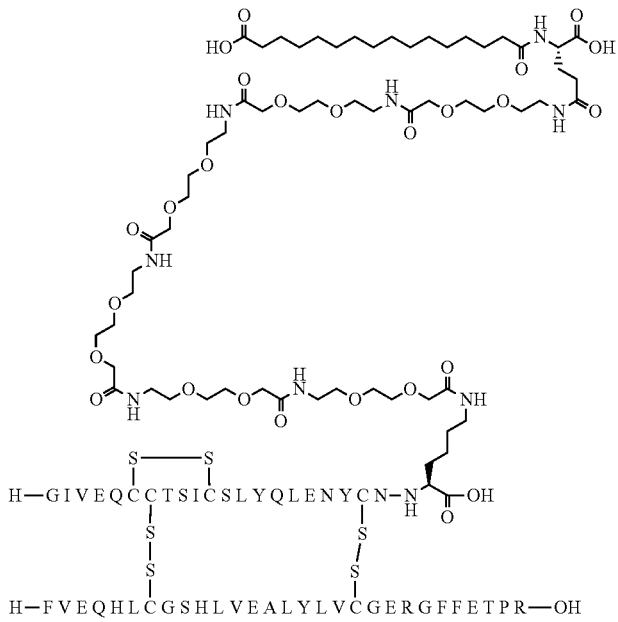

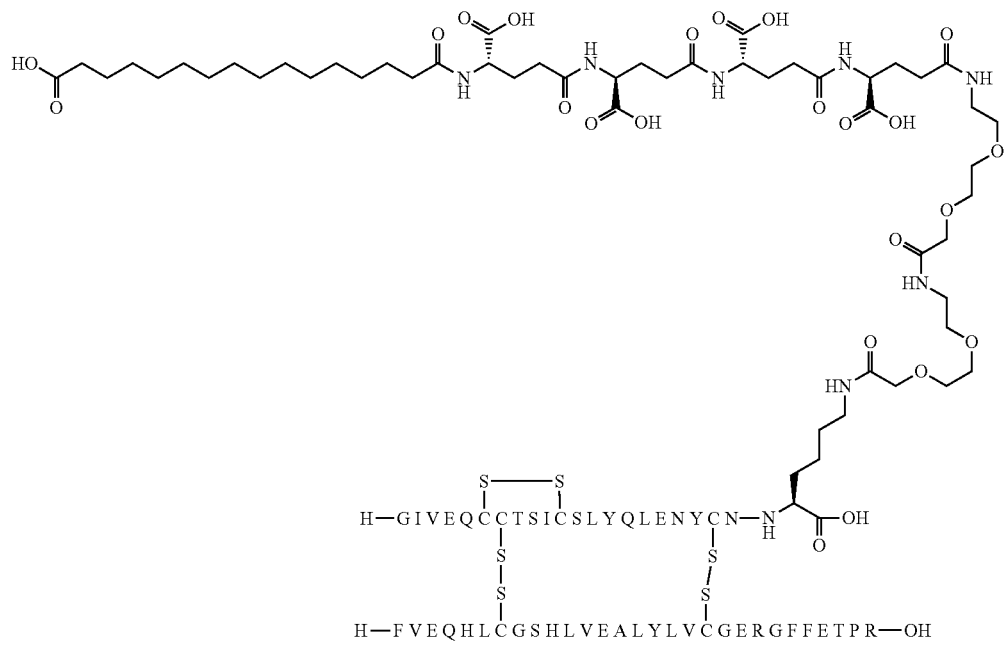

LC-MS (electrospray): m/z=1730.9 (M+4)/4. Calc: 1730.7

Example 46

General Procedure (A)
A22K(N(eps)hexadecanedioyl-4×gGlu), B3Q, B26E, B29R, desB30 Human Insulin; (SEQ ID NOS: 3 and 12)

IUPAC (OpenEye, IUPAC style) name: N{Alpha}([GlnB3,GluB26,ArgB29],des-ThrB30-Insulin-(A)-peptidyl)-N{Epsilon}[(4S)-4-carboxy-4-[[(4S)-4-carboxy-4-[[(4S)-4-carboxy-4-[[(4S)-4-carboxy-4-(15-carboxypentadecanoylamino)butanoyl]amino]-butanoyl]amino]butanoyl]amino]butanoyl]Lys,(B)-peptide.

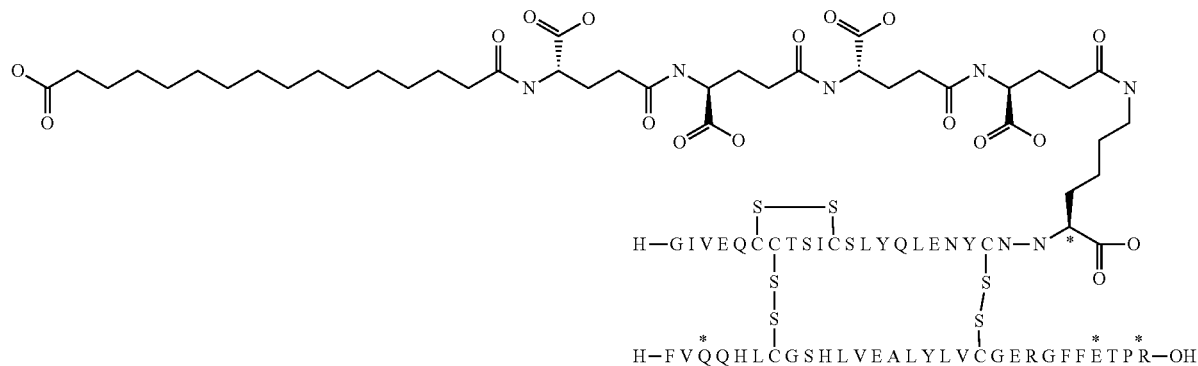

Prior Art Analogue 1
A22K(N(eps)hexadecanedioyl-gGlu-2×OEG), B29R, desB30 Human Insulin: WO 2009 022013; Example 45

IUPAC (OpenEye, IUPAC style) name: N{Alpha}([ArgB29],des-ThrB30-Insulin(human)-(A)-peptidyl)-N{Epsilon}[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]Lys,(B)-peptide.

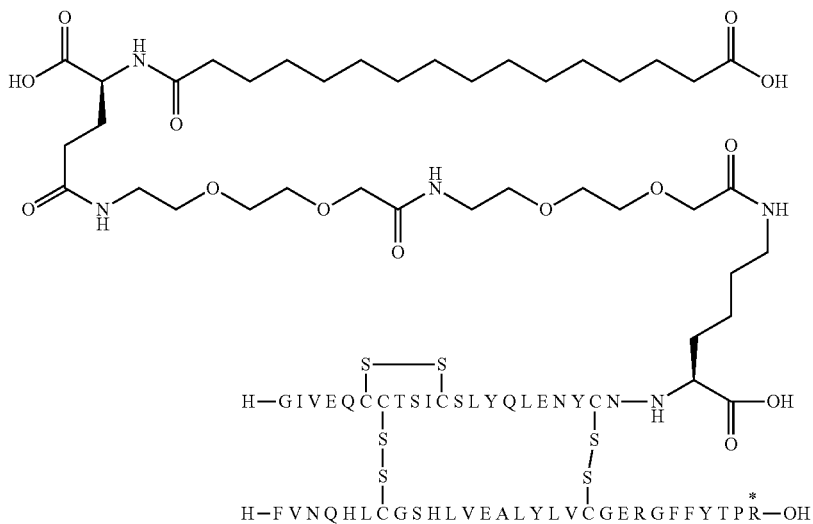

Prior Art Analogue 2
A22K(N(eps)tetradecanedioyl-gGlu-2×OEG), B29R, desB30 Human Insulin: Tetradecanedioic Acid Analogue of Prior Art Analogue 1

IUPAC (OpenEye, IUPAC style) name: N{Alpha}([ArgB29],des-ThrB30-Insulin(human)-(A)-peptidyl)-N{Epsilon}[2-[2-[2-[[2-[2-[2-[[(4S)-4-carboxy-4-(13-carboxytridecanoyl-amino)butanoyl]amino]ethoxy]ethoxy]acetyl]amino]ethoxy]ethoxy] acetyl]Lys,(B)-peptide.

This analogue is the tetradecanedioic acid analogue of the hexadecanedioic acid analogue (Prior Art Analogue 1) disclosed in e.g. WO 2009 022013, Example 45. Insulin substitutions (=mutations) are the same as described in WO 2009 022013, and the only difference is the length of the fatty diacid and, consequently, serum albumin binding affinity associated with increasing the diacid length.

Prior Art Analogue 3
A22K(N(eps)tetradecanedioyl-4×gGlu), B28D, B29R, desB30 Human Insulin: Tetradecanedioyl-4×gGlu Analogue of an Insulin Analogue Disclosed in WO 2007 096431

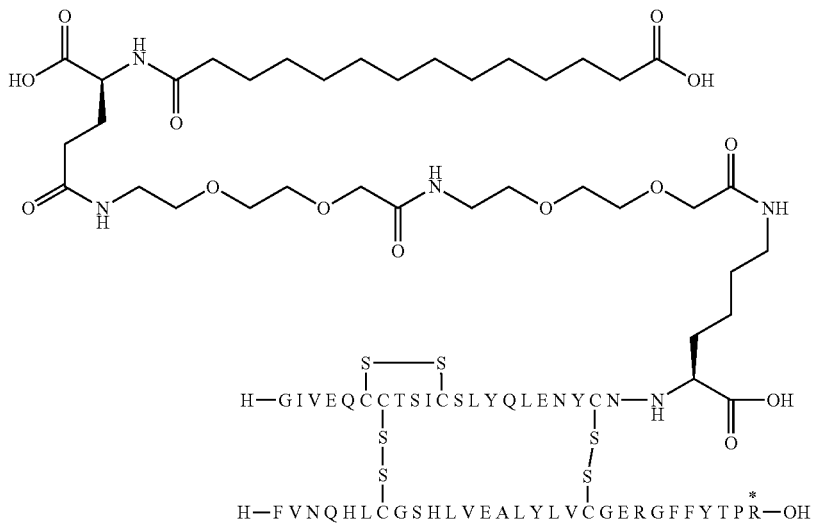

IUPAC (OpenEye, IUPAC style) name: N{Alpha}([AspB28,ArgB29],des-ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]butanoyl]Lys,(B)-peptide.

The B28E substitution has been mentioned in the prior art (in A22K, B28E, B29R, desB30, WO 2009 02213). Further, B26 has been suggested to be Q, E, S, or desB26 (WO 2009 02213). The combination of B28E and B26E has not been

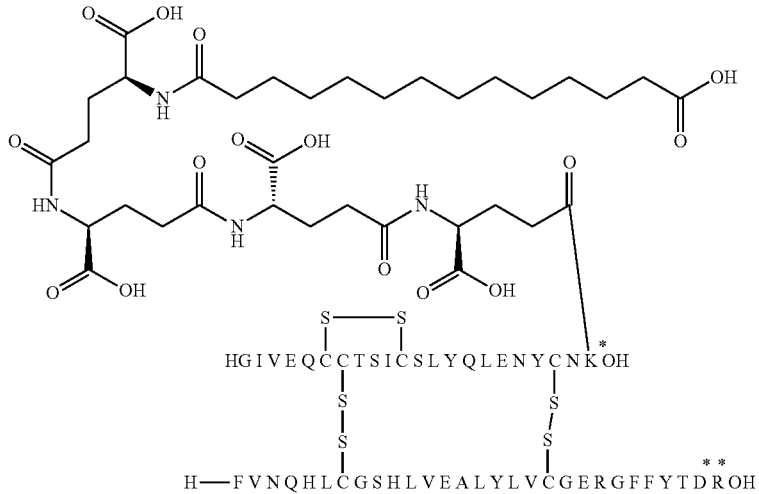

The B28D substitution in this insulin analogue (A22K, B28D, B29R, desB30) have been disclosed in the prior art. However, in this reference molecule, the side chain is derived from tetradecanedioic acid connected via the linker 4×gGlu (like many of the analogues in the present invention).

This is directly to assess the beneficial and unexpected effect of changing B3N (in human insulin and in the prior art) to B3E.

Prior Art Analogue 4

A22K(N(eps)Tetradecanedioyl-gGlu-2×OEG), B26E, B28E, B29R, desB30 Human Insulin: Tetradecanedioyl-gGlu-2×OEG Analogue of an Insulin Analogue Disclosed in WO 2009 022013 suggested, and in this reference molecule, the side chain is derived from tetradecanedioic acid (connected via the linker gGlu-2×OEG (like many of the analogues in the present invention). This is directly to assess the beneficial and unexpected effect of changing B3N (in human insulin and in the prior art) to B3E.

Prior Art Analogue 5

A22K(N(eps)Tetradecanedioyl-4×gGlu), B28E, B29R, desB30 Human Insulin: Tetradecanedioyl-4×gGlu Analogue of a Similar Insulin Analogue with an Octadecanedioic Acid Based Side Chain (Octadecanedioyl-gGlu-2×OEG) Disclosed as Example 18 in WO 2009 022013

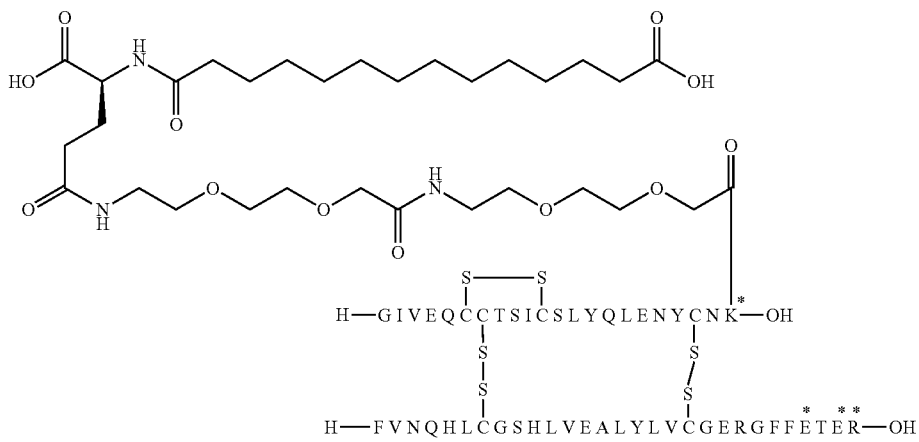

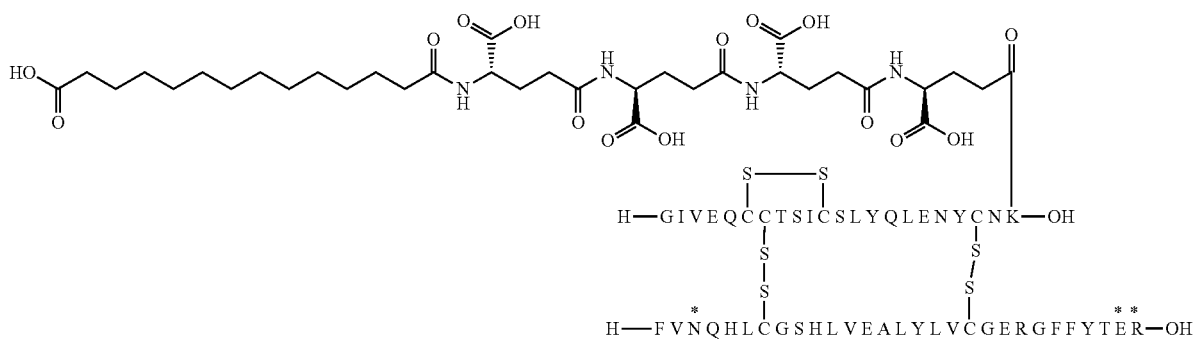

The substitutions in this insulin analogue (A22K, B28E, B29R, desB30) have been disclosed in the prior art. However, in this reference molecule, the side chain is derived from tetradecanedioic acid (not octadecanedioic acid as in the prior art) connected via the linker 4×gGlu (like many of the analogues in the present invention).

This is directly to assess the beneficial and unexpected effect of changing B3N (in human insulin and in the prior art) to B3E.

Prior Art Analogue 6

A22K(N(eps)tetradecanedioyl-gGlu-2×OEG), B28E, B29R, desB30 Human Insulin: Tetradecanedioyl-gGlu-2×OEG Analogue of a Similar Insulin Analogue with an Octadecanedioic Acid Based Side Chain (Octadecanedioyl-gGlu-2×OEG) Disclosed as Example 18 in WO 2009 022013 mined by competition binding in a scintillation proximity assay (SPA) (according to Glendorf T et al. (2008) *Biochemistry* 47 4743-4751).

In brief, dilution series of a human insulin standard and the insulin analogue to be tested are performed in 96-well Optiplates (Perkin-Elmer Life Sciences) followed by the addition of [$^{125}$I-A14Y]-human insulin, anti-IR mouse antibody 83-7, solubilised human IR-A (semipurified by wheat germ agglutinin chromatography from baby hamster kidney (BHK) cells overexpressing the IR-A holoreceptor), and SPA beads (Anti-Mouse polyvinyltoluene SPA Beads, GE Healthcare) in binding buffer consisting of 100 mM HEPES (pH 7.8), 100 mM NaCl, 10 mM MgSO$_4$, and 0.025% (v/v) Tween 20. Plates are incubated with gentle shaking for

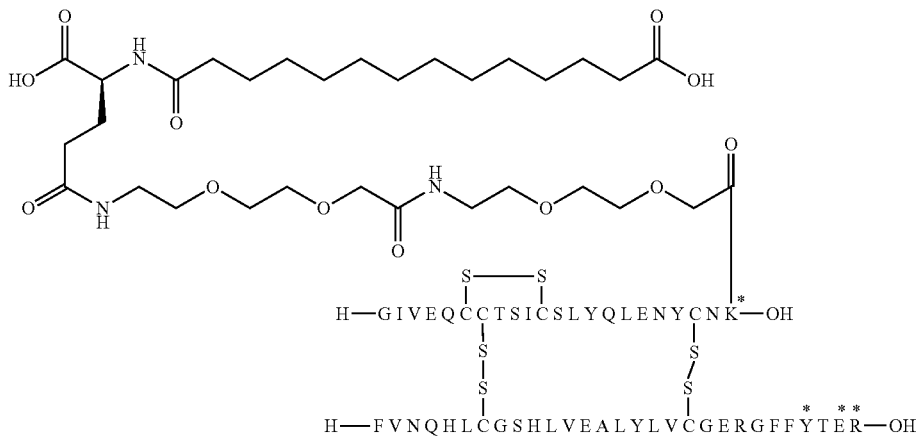

The substitutions in this insulin analogue (A22K, B28E, B29R, desB30) have been disclosed in the prior art. However, in this reference molecule, the side chain is derived from tetradecanedioic acid (not octadecanedioic acid as in the prior art) connected via the linker gGlu-2×OEG (like many of the analogues in the present invention).

This is directly to assess the beneficial and unexpected effect of changing B3N (in human insulin and in the prior art) to B3E.

Example 47

Insulin Receptor Affinity of Selected Insulin Derivatives of the Invention, Measured on Solubilised Receptors The relative binding affinity of the insulin analogues of the invention for the human insulin receptor (IR) is deter- 22-24 h at 22° C., centrifuged at 2000 rpm for 2 minutes and counted on a TopCount NXT (Perkin-Elmer Life Sciences).

Data from the SPA are analysed according to the four-parameter logistic model (Vølund A (1978) *Biometrics* 34 357-365), and the binding affinities of the analogues calculated relative to that of the human insulin standard measured within the same plate.

A related assay is also used wherein the binding buffer contains 1.5% HSA (w/v) (Sigma A1887) in order to mimic more physiological conditions.

Insulin receptor affinities and other in vitro data of selected insulin analogues of the invention are presented in Table 1, below.

Example 48

Insulin and Insulin-Like Growth Factor-1 Receptor Affinities of Selected Insulin Derivatives of the Invention, Measured on Membrane Associated Receptors Membrane-associated human IR and IGF-1R are purified from BHK cells stably transfected with the pZem219B vector containing either the human IR-A, IR-B or IGF-IR insert. BHK cells are harvested and homogenized in ice-cold buffer (25 mM HEPES pH 7.4, 25 mM $CaCl_2$ and 1 mM $MgCl_2$, 250 mg/L bacitracin, 0.1 mM Pefablock). The homogenates are layered on a 41% (w/v) sucrose cushion and centrifuged for 75 minutes at 95000 g at 4° C. The plasma membranes are collected, diluted 1:5 with buffer (as above) and centrifuged again for 45 minutes at 40000 g at 4° C. The pellets are re-suspended in a minimal volume of buffer and drawn through a needle (size 23) three times before storage at −80° C. until usage.

The relative binding affinity for either of the membrane-associated human IR-A, IR-B or IGF-1R is determined by competition binding in a SPA setup. IR assays are performed in duplicate in 96-well OptiPlates (Perkin-Elmer Life Sciences). Membrane protein is incubated with gentle agitation for 150 minutes at 25° C. with 50 µM [$^{125}$I-A14Y]-human insulin in a total volume of 200 µL assay buffer (50 mM HEPES, 150 mM NaCl, 5 mM $MgSO_4$, 0.01% Triton X-100, 0.1% (w/v) HSA (Sigma A1887), Complete EDTA-free protease inhibitors), 50 µg of wheat germ agglutinate (WGA)-coated PVT microspheres (GE Healthcare) and increasing concentrations of ligand. Assays are terminated by centrifugation of the plate at 2000 rpm for 2 minutes and bound radioactivity quantified by counting on a TopCount NXT (Perkin-Elmer Life Sciences).

IGF-1R assays are conducted essentially as for the IR binding assays except that membrane-associated IGF-1R and 50 pM [$^{125}$-Tyr31]-human IGF-1 were employed. Data from the SPA are analysed according to the four-parameter logistic model (Vølund A (1978) *Biometrics* 34 357-365), and the binding affinities of the analogues to be tested are calculated relative to that of the human insulin standard measured within the same plate.

IR (A isoform), IR (B isoform), and IGF-1R binding data of selected insulin analogues of the invention are given in Table 1, below.

TABLE 1

IR (A isoform) IR (B isoform) and IGF-1 receptor binding data in absence and presence of HSA (0.1 and/or 1.5%) as well as functional lipogenesis data from rat adipocytes of selected insulin analogues of the invention

| Ex. No. | hIRA 0% HSA (% rel to HI) Ex 47 | hIRA 1.5% HSA (% rel to HI) Ex 47 | hIRA 0.1% HSA (% rel to HI) Ex 48 | hIRB 0.1% HSA (% rel to HI) Ex 48 | hIGF1R 0.1% HSA (% rel to HI) Ex 48 | Lipogenesis 1% HSA (% rel to HI) Ex 49 |
|---|---|---|---|---|---|---|
| 1 | 107.5 | 71.5 | 103.1 | 159.4 | 66.3 | 23.9 |
| 2 | 60.4 | 38.9 | 50.1 | 70.2 | 36.6 | 14.2 |
| 3 | 90.9 | 75.0 | 74.9 | 156.8 | 44.1 | 27.3 |
| 4 | 47.4 | 44.9 | 36.6 | 56.6 | 28.6 | 15.4 |
| 5 | 161.8 | 86.0 | 75.6 | 75.9 | 169.6 | 20.3 |
| 6 | 100.1 | 57.4 | 61.5 | 118.6 | 55.7 | 11.1 |
| 7 | 100.4 | 67.6 | 93.9 | 108.0 | 124.4 | 21.3 |
| 8 | 95.6 | 64.9 | 34.3 | 59.1 | 42.0 | 17.2 |
| 9 | 83.0 | 70.2 | 36.8 | 68.7 | 29.5 | 30.1 |
| 10 | 111.3 | 77.2 | 64.9 | 93.7 | 77.3 | 26.4 |
| 11 | 119.4 | 101.1 | 68.0 | 110.8 | 13.6 | 20.5 |
| 12 | 180.5 | 121.3 | 66.9 | 104.6 | 13.0 | 31.3 |
| 13 | 232.2 | 174.0 | 63.2 | 90.7 | 65.1 | 78.8 |
| 14 | 117.7 | 60.5 | 40.6 | 81.7 | 35.2 | 29.9 |
| 15 | 294.0 | 236.6 | 107.9 | 174.0 | 10.8 | 70.9 |
| 16 | 317.4 | 229.3 | 112.8 | 168.4 | 61.8 | 130.2 |
| 17 | 242.9 | 163.4 | 85.2 | 129.9 | 32.9 | 70.7 |
| 18 | ND | 113.0 | 57.2 | 93.3 | 7.1 | 29.6 |
| 19 | 260.1 | 188.4 | 88.8 | 154.6 | 22.6 | 80.3 |
| 20 | 122.9 | 85.3 | 44.6 | 94.5 | 43.5 | 19.5 |
| 21 | 133.4 | 74.0 | 46.4 | 76.2 | 7.7 | 17.9 |
| 22 | 115.0 | 89.2 | 45.1 | 70.0 | 35.7 | 23.7 |
| 23 | 229.3 | 181.5 | 78.5 | 143.2 | 5.7 | 59.0 |
| 24 | 274.1 | 211.3 | 88.1 | 163.6 | 24.0 | 78.6 |
| 25 | 157.6 | 9.9 | 71.1 | 72.1 | 55.3 | 3.2 |
| 26 | 63.7 | 7.4 | 19.3 | 28.7 | 28.7 | 2.6 |
| 27 | 113.8 | 5.4 | 16.5 | 23.2 | 14.3 | 3.7 |
| 28 | 102.9 | 10.6 | 29.1 | 35.7 | 26.0 | 4.4 |
| 29 | 157.1 | 14.3 | 31.2 | 29.4 | 99.4 | 3.3 |
| 30 | 167.8 | 10.8 | 27.5 | 32.1 | 64.1 | 3.7 |
| 31 | 138.3 | 9.9 | 30.9 | 38.2 | 55.0 | 4.4 |
| 32 | 96.7 | 10.7 | 25.7 | 55.3 | 20.1 | 1.1 |
| 33 | 102.2 | 13.5 | 32.1 | 40.7 | 85.1 | 2.6 |
| 36 | 120.5 | ND | 48.3 | 82.4 | 5.4 | 18.2 |
| 37 | ND | 16.1 | 20.9 | 47.8 | 32.7 | 3.8 |
| 38 | 154.7 | 77.6 | 64.3 | 77.6 | 102.3 | 27.0 |
| 39 | 136.0 | 104.7 | 76.5 | 162.9 | 18.4 | 31.4 |
| 40 | 169.9 | 151.5 | 78.5 | 133.0 | 9.82 | 31.2 |
| 41 | 141.1 | 19.6 | 29.1 | 46.8 | ND | ND |
| 42 | 104.0 | 16.1 | 34.4 | 40.2 | ND | ND |
| 45 | ND | ND | ND | ND | ND | ND |

ND: Not determined

Example 49

Lipogenesis in Rat Adipocytes

As a measure of in vitro potency of the insulins of the invention, lipogenesis can be used.

Primary rat adipocytes are isolated from the epididymale fat pads and incubated with 3H-glucose in buffer containing e.g. 0.1% fat free HSA and either standard (human insulin, HI) or insulin of the invention. The labelled glucose is converted into extractable lipids in a dose dependent way, resulting in full dose response curves. The result is expressed as relative potency (%) with 95% confidence limits of insulin of the invention compared to standard (HI).

Data are given in Table 1, above.

Example 50

Self-Association Measured by Small Angle X-Ray Scattering (SAXS)

SAXS data was used to estimate the self-association state of the insulin analogues to be tested after subcutaneous injection. SAXS data were collected from Zn-free formulations containing 0.6 mM of insulin analogue to be tested and 140 mM NaCl at pH 7.4. For each analogue, the relative amounts of monomer, dimer and larger species was estimated using the fact that a SAXS scattering profile has an intensity contribution from all individual components in a multicomponent mixture. By using intensities (form factors) from each component it is possible to estimate the volume fraction contribution of each component in the mixture. A system of linear equations using the algorithm of nonnegative or unconstrained least-squares is used to minimize the discrepancy between the experimental and calculated scattering curves. Form factors are calculated from crystal structures of a monomer, dimer, hexamer etc. The volume fractions are expressed in percentages (%).

Results obtained from derivatives of the invention and of derivatives of the prior art are shown in Table 2, below.

TABLE 2

SAXS data of derivatives of the invention and of the prior art

| Ex. No.[a] | SAXS* M + D | SAXS* >D | SAXS* M | SAXS* D |
|---|---|---|---|---|
| 1 | 100 | 0 | 100 | 0 |
| 2 | 97 | 3 | 81 | 16 |
| 3 | 96 | 4 | 90 | 6 |
| 4 | 98 | 2 | 82 | 16 |
| 7 | 98 | 2 | 70 | 28 |
| 10 | 96 | 4 | 74 | 22 |
| 11 | 99 | 1 | 65 | 34 |
| 12 | 99 | 1 | 67 | 32 |
| 28 | 97 | 2 | 69 | 29 |
| PA 1 | 44 | 56 | 27 | 17 |
| PA 2 | 28 | 72 | 28 | 0 |
| PA 3 | 91 | 9 | 64 | 27 |
| PA 4 | 96 | 4 | 74 | 22 |
| PA 5 | 68 | 32 | 18 | 50 |
| PA 6 | 66 | 34 | 0 | 66 |

[a]PA refers to Prior Art Compound
*M: Percentage of monomeric species in formulation; D: Percentage of dimeric species in formulation; >D: Percentage of species larger than dimeric in formulation; M + D: Percentage of sum of monomeric and dimeric species in formulation.

It can be concluded from these studies that the derivatives of the invention, at conditions mimicking conditions in the subcutaneous tissue after injection, are much more prone to dissociate into monomers and will thus be absorbed much more quickly after subcutaneous injection than similar analogues of the prior art. The combined monomeric and dimeric content ranges from 96-100% for the analogues of the invention with very little content of species larger than dimers (4% at most).

The majority of the analogues of the prior art are composed of much larger species than the analogues of the invention, with only one exception (Prior Art Analogue 4). This analogue is, however, not stable in formulation without zinc as shown in the following examples.

Example 51

Preparation of Pharmaceutical Preparations

The pharmaceutical preparations of the present invention may be formulated as an aqueous solution. The aqueous solution is made isotonic, for example, with sodium chloride and/or glycerol. Furthermore, the aqueous medium may contain buffers and preservatives. The pH value of the preparation is adjusted to the desired value and may be between about 3 to about 8.5, between about 3 and about 5, or about 6.5, or about 7.4, or about 7.5, depending on the isoelectric point, pI, of the insulin analogue in question.

Preparation of Zinc-Free Insulin Formulations

Zinc-free insulin analogues were dissolved in aqueous solution, which in the final formulation contained 0.6 mM insulin analogue, 16 mM m-cresol, 16 mM phenol and appropriate amounts of nicotinamide and glycerol, and the pH was adjusted to 7.3-7.5 (measured at room temperature) using 1 N hydrochloric acid/1 N NaOH. Water was added to the final volume and the solution was sterile-filtered through a 0.2 μm filter. The formulation was filled into 2 ml vials and sealed using crimp caps.

TABLE 3

Exemplary compositions of insulin preparations

| Formulation | Ex. No. | Insulin derivative (mM) | Phenol (mM) | m-Cresol (mM) | Glycerol (% w/v) | pH |
|---|---|---|---|---|---|---|
| A | 2 | 0.6 | 16 | 16 | 2.0 | 7.4 |
| B | 2 | 0.6 | 16 | 16 | 1.6 | 7.4 |
| C | 2 | 0.6 | 16 | 16 | 1.7 | 7.4 |

Example 52

ThT Fibrillation Assay for the Assessment of Physical Stability of Protein Formulations Low physical stability of a peptide may lead to amyloid fibril formation, which is observed as well-ordered, thread-like macromolecular structures in the sample eventually resulting in gel formation. Thioflavin T (ThT) has a distinct fluorescence signature when binding to fibrils [Naiki et al. (1989) *Anal. Biochem.* 177 244-249; LeVine (1999) *Methods. Enzymol.* 309 274-284].

Formation of a partially folded intermediate of the peptide is suggested as a general initiating mechanism for fibrillation. Few of those intermediates nucleate to form a template onto which further intermediates may assemble and the fibrillation proceeds. The lag-time corresponds to the interval in which the critical mass of nucleus is built up and the apparent rate constant is the rate with which the fibril itself is formed (FIG. 1).

Sample Preparation

Samples were prepared freshly before each assay. Samples of each composition was mixed with an aqueous ThT-solution (0.1 mM ThT) in a volumetric ratio of 990:10 and transferred to a 96 well microtiter plate (Packard Opti-Plate™-96, white polystyrene). Usually, four or eight replica of each sample (corresponding to one test condition) were placed in one column of wells. The plate was sealed with Scotch 15 Pad (Qiagen).

Incubation and Fluorescence Measurement

Incubation at given temperature, shaking and measurement of the ThT fluorescence emission were done in a Fluoroskan Ascent FL fluorescence plate reader or Varioskan plate reader (Thermo Labsystems). The temperature was adjusted to 37° C. The orbital shaking was adjusted to 960 rpm with an amplitude of 1 mm in all the presented data. Fluorescence measurement was done using excitation through a 444 nm filter and measurement of emission through a 485 nm filter. Each run was initiated by incubating the plate at the assay temperature for 10 minutes. The plate was measured every 20 minutes for up to 45 hours. Between each measurement, the plate was shaken and heated as described.

Data Handling

Figure 1A:
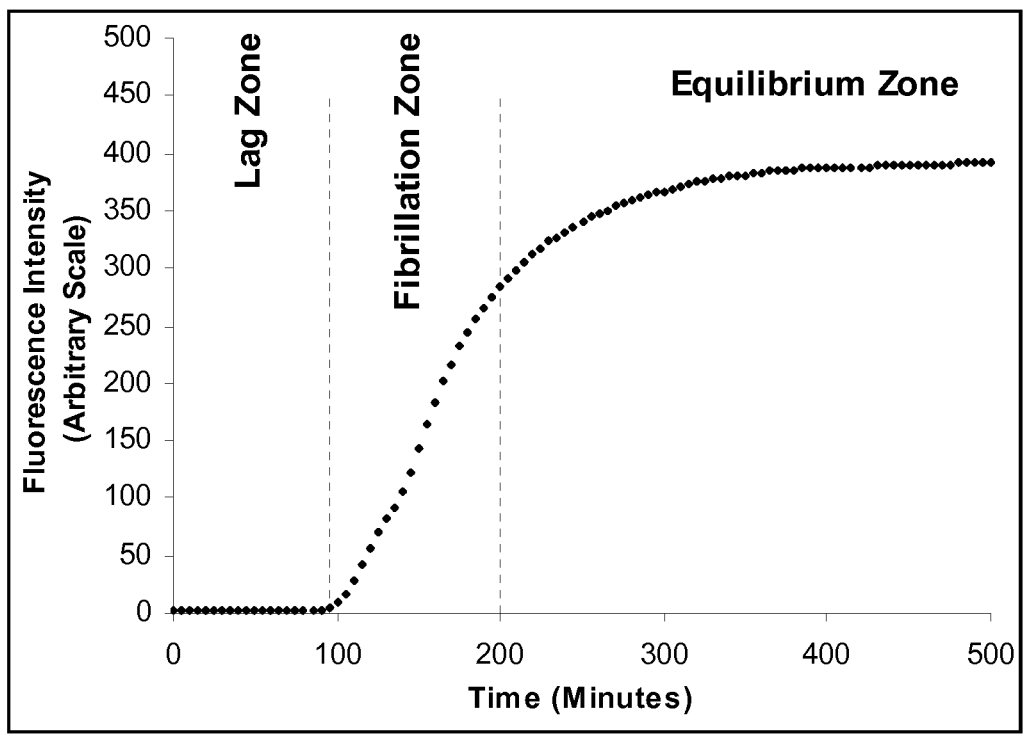
FIGS. 1A, 1B and 1C shows a schematic illustration of the fibrillation process when measured in the "ThT fibrillation assay" described herein.
Figure 1B:
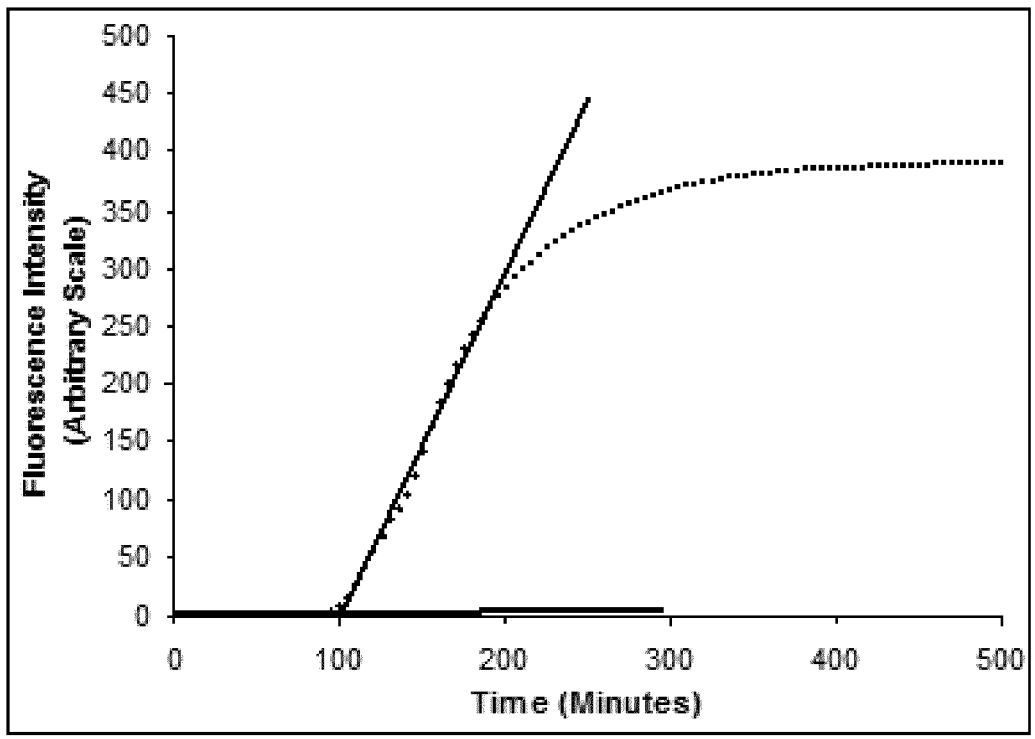
Figure 1C:
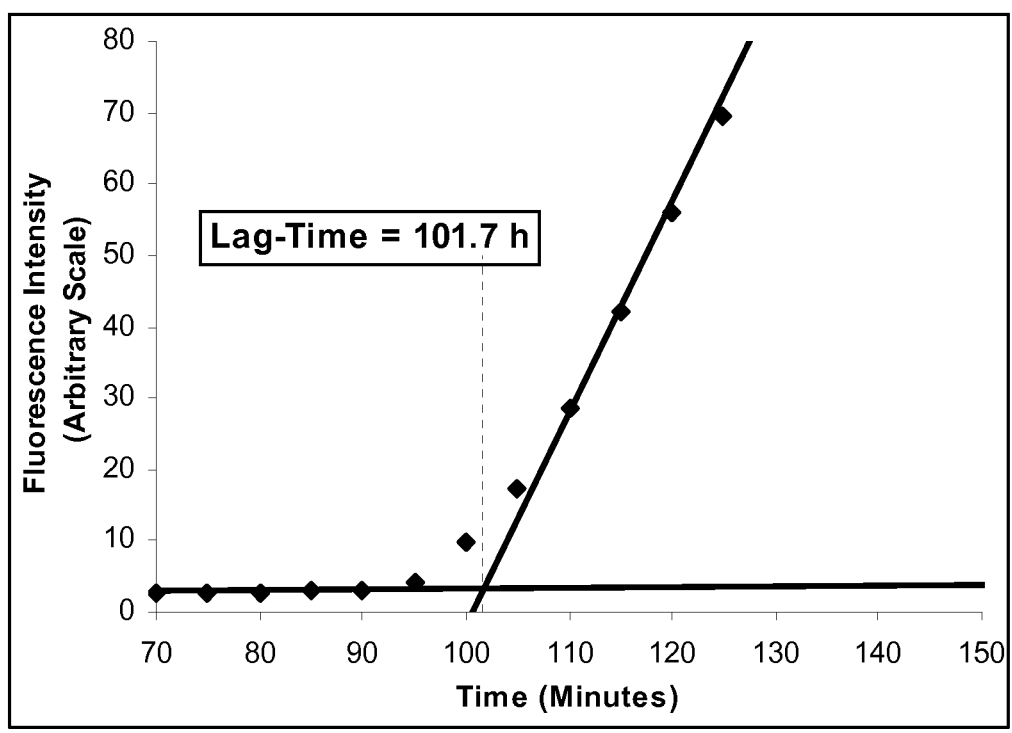

Fluorescence vs. time plots were generated in Microsoft Excel and the lag time was estimated as the intercept between linear approximation of the Lag Zone and Fibrillation Zone as illustrated in FIGS. 1A, 1B and 1C. An increase in lag-time corresponds to an increased physical stability. The data points are typically a mean of four or eight samples.

Results obtained for the A22K acylated analogues of the invention, and of similar A22K acylated analogues of the prior art are shown in Table 4, below.

TABLE 4

Physical stability measured as ThT lag time of zinc-free preparations

| Ex. No.[a] | Formulation | Lag time (h) in ThT assay |
|---|---|---|
| 1 | A | 10 |
| 2 | C | 45* |
| 3 | A | 44* |
| 4 | | 45* |
| 7 | C | 20 |
| 10 | C | 13 |
| 11 | C | 45* |
| 12 | C | 37 |
| 20 | C | 45* |
| PA 1 | A | 5 |
| PA 2 | A | 10 |
| PA 3 | A | 45* |
| PA 4 | A | 2 |
| PA 5 | A | 36 |
| PA 6 | A | 22 |

[a]PA refers to Prior Art Compound
*No fibrillation within timespan of ThT assay It is concluded that the A22K acylated insulin analogues of the invention display better or similar stability towards fibrillation (i.e. have increased physical stability) in zinc-free formulation both with and without nicotinamide added than similar analogues of the prior art. This is very surprising since SAXS data indicate that the insulin analogues of the invention are smaller in size (i.e. composed of monomers and dimers) which the skilled person would expect would lead to less physical stability.

Example 53

Analysis of Insulin Chemical Stability
Size Exclusion Chromatography
Formulations Used: See Example 52

Quantitative determination of high molecular weight protein (HMWP) and monomer insulin analogue was performed on Waters Acquity BEH200 SEC column (150×2.4 mm, part no. 186005225) with an eluent containing 55% (v/v) acetonitrile, 0.05% TFA at a flow rate of 0.2 ml/min and a column temperature of 40° C. Detection was performed with a tuneable absorbance detector (Waters Acquity TUV) at 215 nm. Injection volume was 1.5 µl of both the 600 µM insulin analogue formulations and a 600 µM human insulin standard. Each analogue preparation was incubated at 5, 25 and 37° C. in 2 ml vials. At defined times HMWP and content of the preparations were measured.

The results are shown in Table 5, below.

TABLE 5

HMWP content by storage at 30° C. and at 37° C.
Delta-values from start are given in parentheses

| Ex. No.[a] | Start | 2 weeks 37° C. | 4 weeks 37° C. | 5 weeks 30° C. | 5 weeks 37° C. |
|---|---|---|---|---|---|
| 1 | 0.2% | 0.2% (+0%) | ND | 0.2% (+0%) | |
| 2 | 0.2% | 0.2% (+0%) | ND | 0.2% (+0%) | 0.2% (+0%) |
| 3 | 0.5% | 0.4% (+0%) | ND | 0.4% (+0%) | |
| 4 | 0.5% | 0.4% (+0%) | ND | 0.4% (+0%) | 0.5% (+0%) |
| 7 | 0.3% | 0.3% (+0%) | 0.4% (+0.1%) | | |
| 10 | 0.4% | 0.5% (+0.1%) | ND | 0.4% (+0%) | |
| 11 | 0.5% | 0.4% (+0%) | 0.4% (+0%) | ND | 0.4% (+0%) |
| 12 | 0.6% | 0.5% (+0%) | 0.5% (+0%) | ND | 0.6% (+0%) |
| 20 | 1.2% | 1.4% (+0.2%) | ND | 1.4% (+0.2%) | |
| PA 1 | 2.6% | 4.6% (+2.0%) | ND | 5.1% (+1.0%) | 8.1% (+5.5%) |
| PA 2 | 0.7% | 1.5% (+0.8%) | ND | 1.6% (+0.9%) | |
| PA 3 | 0.2% | 1.3% (+1.1%) | ND | 0.2% (+0.1%) | 2.6% (+2.4%) |
| PA 4 | 0.4% | 1.0% (+0.6%) | ND | ND | 2.2% (+1.8%) |
| PA 5 | 0.7% | 1.0% (+0.3%) | ND | ND | 1.8% (+1.1%) |
| PA 6 | 0.5% | 1.3% (+0.8%) | ND | ND | 2.4% (+1.9%) |

[a]) PA refers to Prior Art Compound
ND: Not determined

It is concluded that formation of high molecular weight proteins (HMWP) by storage in zinc-free formulation at 37° C. is very, very low, and less than or similar to insulin derivatives of the prior art.

Reverse Phase Chromatography (UPLC)

Determination of the insulin related impurities were performed on a UPLC system using a CSH Phenyl-Hexyl column, (2.1×150 mm, 1.7 µm) (Waters part no. 186005408), with a flow rate of 0.3 ml/min at 30° C. and with UV detection at 215 nm. Elution was performed with a mobile phase consisting of the following: A: 10% (v/v) acetonitrile, 100 mM di-ammonium hydrogen phosphate, pH 3.6, and B: 80% (v/v) acetonitrile. Gradient: 0-3 min linear change from 26% B to 28.5% B, 3-34 min linear change to 37% B, 34-36 minutes linear change to 80% B for column wash, before returning to initial conditions at 39 min 26% B. The amount of impurities was determined as absorbance area measured in percent of total absorbance area determined after elution of the preservatives. Each analogue preparation was incubated at 5, 25 and 37° C. in 2 ml vials. At defined times the insulin related impurities of the preparations was measured.

The results are shown in Table 6, below.

TABLE 6

Purity by storage at 37° C.
Delta-values from start are given in parentheses

| Ex. No.[a] | Start | 2 weeks 37° C. | 4 weeks 37° C. | 5 weeks 37° C. |
|---|---|---|---|---|
| 2 | 96.0% | 95.4% (−0.6%) | ND | 93.3% (−2.7%) |
| 4 | 91.4% | 91.0% (−0.4%) | ND | 89.1% (−2.3%) |
| 3 | 88.9% | 88.2% (−0.7%) | ND | 86.6% (−2.3%) |
| 7 | 97.4% | 94.7% (−2.7%) | 92.3% (−5.1%) | ND |

TABLE 6-continued

Purity by storage at 37° C.
Delta-values from start are given in parentheses

| Ex. No.<sup>a</sup> | Start | 2 weeks 37° C. | 4 weeks 37° C. | 5 weeks 37° C. |
|---|---|---|---|---|
| 11 | 95.0% | 95.3% (−0%) | 92.2% (−2.8%) | 92.3% (−2.7%) |
| 12 | 90.5% | 89.5% (−1.0%) | 86.9% (−3.6%) | 86.7% (−3.8%) |
| PA 1 | 94.6% | 85.0% (−9.6%) | ND | 73.6% (−21.0%) |
| PA 3 | 92.4% | 80.9% (−11.5%) | ND | 69.1% (−23.3%) |
| PA 4 | 95.3% | 85.6% (−9.7%) | ND | 72.9% (−22.4%) |
| PA 5 | 90.8% | 83.4% (−7.4%) | ND | 72.4% (−18.4%) |
| PA 6 | 93.2% | 85.6% (−7.6%) | ND | 73.3% (−19.9%) |

<sup>a</sup>PA refers to Prior Art Compound
ND: Not determined

It is concluded that the insulin derivatives of the invention are far more stable in formulation without zinc than similar A22K acylated analogues of the prior art. The analogues of the prior art are so unstable that 7-12% (absolute) purity loss is observed after 2 weeks of storage and around 20% purity loss after 5 weeks of storage in zinc-free formulation. The analogues of the prior art are not stable enough to be formulated without zinc. The analogues of the invention display significant less purity loss and are thus far more stable and well suited for formulation without zinc.

Example 54

Subcutaneous PK/PD Profiles in LYD Pigs

The insulin derivatives of the invention may be tested by subcutaneous administration to pigs, e.g. comparing with insulin aspart (NovoRapid) in the commercial formulation or comparing with similar A22K acylated insulin analogues of the prior art according to this protocol. The derivatives may be tested for pharmacokinetic and/or pharmacodynamic parameters.

General Methods Used

Ultrasound Examination and Marking of Injection Area

During anaesthesia for placement of permanent intravenous catheters, the pigs are examined by ultrasound with and Esaote ultrasound scanner model "MyLabFive" and a linear probe type "LA435 6-18 MHz". Mid neck between ear and scapula, on the right or left side (opposite the catheter), an area of 2×2 cm with no underlying muscle (suitable for subcutaneous injection) is identified and marked by tattoo.

Feeding Schedule

The pigs are fasted (no breakfast) prior to the experiment.
The pigs are in their normal pens during the entire experiment and they are not anaesthetized. The pigs are fasted until the 12-hour blood sample has been collected, but with free access to water. After the 12-hour blood sample the pigs are fed food and apples.

Dosing

The Penfill is mounted in a NovoPen®4. A new needle is used for each pig. A needle stopper is used to secure max s.c. penetration to 5 mm below the epidermis. Dose volume (IU volume) is calculated and noted for each pig.

Dose volume(U)=((Weight×dose nmol/kg)/conc nmol/mL)×100 U/mL

The pig is dosed in the sub-cutis laterally on the right or left side (opposite the catheter) of the neck and the needle is kept in the sub-cutis for a minimum of 10 seconds after injection to secure deposition of compound.

Treatment of Hypoglycemia

After subcutaneous dosing, glucose solution should be ready for i.v. injection to prevent hypoglycaemia, i.e. 4-5 syringes (20 mL) are filled with sterile 20% glucose, ready for use. Diagnosis of hypoglycemia is based on clinical symptoms and blood glucose measurements on a glucometer (Glucocard X-meter).

Treatment consists of slow i.v. injection of 50-100 ml 20% glucose (10-20 g glucose). The glucose is given in fractions over 5-10 minutes until effect.

Blood Sampling

The patency of the jugular catheters is checked prior to the experiment with sterile 0.9% NaCl without addition of 10 IU/mL heparin.

Before and after the dosing, blood samples will be taken in the stable from a central venous catheter at the following time points:

Predose (−10, 0), 3, 6, 9, 12, 15, 20, 30, 45, 60, 90, 120, 150, 180, 240, 300, 360, 420, 480, 540, 600 and 720 minutes Samples are taken with a 3-way stop-cock. 4-5 ml of waste blood is withdrawn and discarded before taking the sample.

Blood samples of 0.8 ml are collected into tubes coated with EDTA for glucose and insulin analysis.

After each blood sample the catheter is flushed with 5 ml of sterile 0.9% NaCl without addition of 10 IU/mL heparin.

The tube is tilted gently a minimum of 10 times to ensure sufficient mixing of blood and anticoagulant (EDTA) and after one minute it is placed on wet ice. The tubes are spun for 10 min at 3000 rpm and 4° C. within 1 hour after sampling. The samples are stored on wet ice until pipetting.

Aseptic technique is demanded to avoid bacterial growth in the catheter with increased risk of clotting.

Closure of the Catheters after the Experiment

If blood sampling has not been performed using an aseptic technique, a single intravenous treatment with 1 ml per 10 kg Pentrexyl® (1 g of ampicillin dissolved in 10 ml 0.9% NaCl) can be administered slowly i.v. via the catheter that has been used for blood sampling. Following this treatment, the catheter is flushed with 10 ml 0.9% NaCl.

Catheters are flushed with 5 ml of sterile 0.9% NaCl added heparin (10 IU/mL). The catheters are closed with a new luer-lock with latex injection membrane and 1.0 ml of TauroLockHep500 is injected through the membrane as a lock for the catheter.

Analysis of Blood Samples

Plasma glucose: 10 ul of plasma is pipetted into 500 ul of buffer solution for measurements of glucose concentration in plasma in the BIOSEN autoanalyser.

Plasma insulin: 1×50 μl of plasma are pipetted into 0.65 ml Micronic® tubes (ELISA/LOCI/SPA setup) for analysis, using either ELISA or LC-MS.

Plasma is stored frozen at −20° C.

Example 55

Subcutaneous PK/PD Profile of the Insulin Derivative of Example 12 in LYD Pigs

Following the general procedure above, the following PK and PD profiles were obtained for the insulin derivative of Example 12, A22K(N(eps)tetradecanedioyl-4×gGlu), B3E, B26E, B29R, desB30 human insulin.

Formulations Used

The compound Example 12, 608.6 µM; 1.6% (w/vol) glycerol; 16 mM phenol; 16 mM m-cresol; 7 mM phosphate, 10 mM sodium chloride; pH=7.4 (0 Zn/hexamer), 1 nmol/kg.

The results of these determinations are presented in the appended FIGS. 5A and 5B, and in Table 1, below.

FIGS. 5A and 5B shows the PK (pharmacokinetic) profile (insulin concentrations vs. time) of the insulin derivative of Example 12, i.e. A22K(N(eps)tetradecanedioyl-4×gGlu), B3E, B26E, B29R, desB30 human insulin, formulated with 0 zinc per 6 insulin molecules (1 nmol/kg), and the resulting changes in plasma glucose, respectively (1 nmol/kg).

TABLE 1

Pharmacokinetic parameters after sc. dosing of
1 nmol/kg of the compound Example 12 to pigs

| Compound | | AUC/D pM*min/ (pmol/kg) | $T_{max}$ (min) | $C_{max}$/D pM/ (nmol/kg) | MRT (min) | $T_{1/2}{}^a$ (min) |
|---|---|---|---|---|---|---|
| Example 12 | Mean | 54 | 45 | 572 | 91 | 46 |
| 0 Zn/hexamer | SD | 6 | | 71 | 11 | 7 |
| (n = 8) | | | | | | |
| 1 nmol/kg | | | | | | |

$^a T_{1/2}$ given as harmonic mean ± pseudoSD

It is concluded that the insulin derivative of Example 12, in a formulation without zinc, is associated with an attractive profile with an early $T_{max}$ (45 minutes), and both a short MRT (91 minutes) as well as short T½ (46 minutes). This makes this insulin highly useful for prandial use.

Example 56

Subcutaneous PK/PD Profile of the Insulin Derivative of Example 1 in LYD Pigs

Following the general procedure above, the following PK and PD profiles were obtained for the insulin derivative of Example 1, A22K(N(eps)tetradecanedioyl-gGlu-2×OEG), B3E, B27E, B28E, B29R, desB30 human insulin.

Formulations Used

The compound of Example 1, 611.6 µM; 2% (w/vol) glycerol; 16 mM phenol; 16 mM m-cresol; 7 mM phosphate; pH=7.4 (0 Zn/hexamer), 1 nmol/kg.

The results of these determinations are presented in the appended FIGS. 6A and 6B, and in Table 2, below.

FIGS. 6A and 6B shows the PK (pharmacokinetic) profile (insulin concentrations vs. time) of the insulin derivative of Example 1, i.e. A22K(N(eps)tetradecanedioyl-gGlu-2× OEG), B3E, B27E, B28E, B29R, desB30 human insulin, formulated with 0 zinc per 6 insulin molecules (1 nmol/kg), and the resulting changes in plasma glucose, respectively (1 nmol/kg).

TABLE 2

Pharmacokinetic parameters after sc. dosing of
1 nmol/kg of the compound of Example 1 to pigs

| Compound | | AUC/D pM*min/ (pmol/kg) | $T_{max}$ (min) | $C_{max}$/D pM/ (nmol/kg) | MRT (min) | $T_{1/2}{}^a$ (min) |
|---|---|---|---|---|---|---|
| Example 1 | Mean | 71 | 30 | 750 | 113 | 103 |
| 0 Zn/hexamer | SD | 11 | | 261 | 14 | 16 |
| (n = 8) | | | | | | |
| 1 nmol/kg | | | | | | |

$^a T_{1/2}$ given as harmonic mean ± pseudoSD

It is concluded that the insulin derivative of Example 1, in a formulation without zinc, is associated with an attractive profile with an early $T_{max}$ (30 minutes), and both a short MRT (113 minutes) as well as short T½ (103 minutes). This makes this insulin highly useful for prandial use.

Example 57

Subcutaneous PK/PD Profile of the Insulin Derivative of Example 7 in LYD Pigs

Following the general procedure above, the following PK and PD profiles were obtained for the insulin derivative of Example 7, A22K(N(eps)tetradecanedioyl-gGlu-2×OEG), B3E, B28D, B29R, desB30 human insulin.

Formulations Used

The compound of Example 7, 610 µM; 2% (w/vol) glycerol; 16 mM phenol; 16 mM m-cresol; 7 mM phosphate; pH=7.4 (0 Zn/hexamer), 1 nmol/kg.

The results of these determinations are presented in the appended FIGS. 7A and 7B, and in Table 3, below.

FIGS. 7A and 7B shows the PK (pharmacokinetic) profile (insulin concentrations vs. time) of the insulin derivative of Example 7, i.e. A22K(N(eps)tetradecanedioyl-gGlu-2× OEG), B3E, B28D, B29R, desB30 human insulin, formulated with 0 zinc per 6 insulin molecules (1 nmol/kg), and the resulting changes in plasma glucose, respectively (1 nmol/kg).

TABLE 3

Pharmacokinetic parameters after sc. dosing of
1 nmol/kg of the compound of Example 7 to pigs

| Compound | | AUC/D pM*min/ (pmol/kg) | $T_{max}$ (min) | $C_{max}$/D pM/ (nmol/kg) | MRT (min) | $T_{1/2}{}^a$ (min) |
|---|---|---|---|---|---|---|
| Example 7 | Mean | 71 | 30 | 564 | 133 | 86 |
| 0 Zn/hexamer | SD | 10 | | 207 | 20 | 12 |
| (n = 8) | | | | | | |
| 1 nmol/kg | | | | | | |

$^a T_{1/2}$ given as harmonic mean ± pseudoSD

It is concluded that the insulin derivative of Example 7, in a formulation without zinc, is associated with an attractive profile with an early $T_{max}$ (30 minutes), and both a short MRT (133 minutes) as well as short T½ (86 minutes). This makes this insulin highly useful for prandial use.

Example 58

Subcutaneous PK/PD Profile of the Insulin Derivative of Example 10 in LYD Pigs

Following the general procedure above, the following PK and PD profiles were obtained for the insulin derivative of Example 10, A22K(N(eps)tetradecanedioyl-4×gGlu), B3E, B28D, B29R, desB30 human insulin.

Formulations Used

The compound of Example 10, 610 µM; 2% (w/vol) glycerol; 16 mM phenol; 16 mM m-cresol; 7 mM phosphate; pH=7.4 (0 Zn/hexamer), 1 nmol/kg.

The results of these determinations are presented in the appended FIGS. 8A and 8B, and in Table 4, below.

FIGS. 8A and 8B shows the PK (pharmacokinetic) profile (insulin concentrations vs. time) of the insulin derivative of Example 10, i.e. A22K(N(eps)tetradecanedioyl-4×gGlu), B3E, B28D, B29R, desB30 human insulin, formulated with 0 zinc per 6 insulin molecules (1 nmol/kg), and the resulting changes in plasma glucose, respectively (1 nmol/kg).

TABLE 4

Pharmacokinetic parameters after sc. dosing of
1 nmol/kg of the compound of Example 10 to pigs

| Compound | | AUC/D pM*min/ (pmol/kg) | $T_{max}$ (min) | $C_{max}$/D pM/ (nmol/kg) | MRT (min) | $T_{1/2}^a$ (min) |
|---|---|---|---|---|---|---|
| Example 10 | Mean | 66 | 25 | 569 | 118 | 97 |
| 0 Zn/hexamer | SD | 11 | | 179 | 19 | 16 |
| (n = 8) | | | | | | |
| 1 nmol/kg | | | | | | |

$^a T_{1/2}$ given as harmonic mean ± pseudoSD

It is concluded that the insulin derivative of Example 10, in a formulation without zinc, is associated with an attractive profile with an early $T_{max}$ (25 minutes), and both a short MRT (118 minutes) as well as short T½ (97 minutes). This makes this insulin highly useful for prandial use.

Example 59

Subcutaneous PK/PD Profile of an Insulin Derivative of the Prior Art in LYD Pigs Following the general procedure above, the following PK and PD profiles were obtained for the insulin derivative of the prior art (Prior Art Analogue 1), A22K(N(eps)-hexadecanedioyl-gGlu-2×OEG), B29R, desB30 human insulin (WO 2009/022013, Example 45

Formulations Used

The compound of WO 2009/022013, Example 45, 588 µM; 1.6% (w/vol) glycerol; 30 mM phenol; 7 mM tris, pH=7.4 (0 Zn/hexamer), 1 nmol/kg.

The results of these determinations are presented in the appended FIGS. 3A and 3B, and in Table 11, below.

FIGS. 3A and 3B shows the PK (pharmacokinetic) profile (insulin concentrations vs. time) of an insulin derivative of the prior art, i.e. A22K(N(eps)-hexadecanedioyl-gGlu-2× OEG), B29R, desB30 human insulin (WO 2009/022013, Example 45), formulated with 0 zinc per 6 insulin molecules (1 nmol/kg), and the resulting changes in plasma glucose, respectively (1 nmol/kg).

TABLE 11

Pharmacokinetic parameters after sc. dosing of 1 nmol/kg
of the compound of WO 2009/0022013, Example 45 to pigs

| Compound | | AUC/D pM*min/ (pmol/kg) | $T_{max}^a$ (min) | $C_{max}$/D pM/ (nmol/kg) | MRT (min) | $T_{1/2}^b$ (min) |
|---|---|---|---|---|---|---|
| WO 2009/022013 | Mean | 422 | 45 | 736 | 1287 | 987 |
| Ex. 45 | SD | 51 | 17 | 344 | 86 | 36 |
| 0 Zn/hexamer | | | | | | |
| (n = 4) | | | | | | |
| 1 nmol/kg | | | | | | |

$^a T_{max}$ given as median ± SD
$^b T_{1/2}$ given as harmonic mean ± pseudoSD It is concluded that the insulin derivative of the prior art, WO 2009/022013, Example 45, in a formulation without zinc is associated with a protracted tailing, possibly originating from a delayed absorption of a part of the subcutaneous depot. The plasma concentration of this insulin at the 24 hour (1440 minutes) time point is 98 µM. Further, the blood glucose lowering effect is extended to last for at least 8 hours (480 minutes). Mean residence time was 1287 minutes, almost 1 day. This makes this insulin of the prior art inappropriate for prandial use.

Example 60

Subcutaneous PK/PD Profile of a Close Analogue of an Insulin Derivative of the Prior Art in LYD Pigs Following the general procedure above, the following PK and PD profiles were obtained for the C14 diacid analogue (Prior Art Analogue 2), A22K(N(eps)-tetradecanedioyl-gGlu-2×OEG), B29R, desB30 human insulin representative of the prior art as described in WO 2009/022013 (see in particular Example 45 (A22K(N(eps)-hexadecanedioyl-gGlu-2×OEG), B29R, desB30 human insulin).

Formulations Used

A22K(N(eps)-tetradecanedioyl-gGlu-2×OEG), B29R, desB30 human insulin (the 1,14-tetradecanedioyl (C14 diacid) analogue of the 1,16-hexadecanedioyl (C16 diacid) analogue of WO 2009/022013, Example 45), 588 µM; 1.6% (w/vol) glycerol; 30 mM phenol; 7 mM tris, pH=7.4 (0 Zn/hexamer)

The results of these determinations are presented in the appended FIGS. 4A and 4B in Table 12, below.

FIGS. 4A and 4B shows the PK (pharmacokinetic) profile (insulin concentrations vs. time) of Prior Art Analogue 2, a C14 diacid analogue of an insulin derivative representative of the prior art, i.e. A22K(N(eps)-hexadecanedioyl-gGlu-2× OEG), B29R, desB30 human insulin (WO 2009/022013, Example 45, Prior Art Analogue 1), formulated with 0 zinc per 6 insulin molecules (72 nmol/animal), and the resulting changes in plasma glucose, respectively (72 nmol/animal).

TABLE 12

Pharmacokinetic parameters after sc. dosing of 1 nmol/kg of the
C14 diacid analogue of the C16 diacid analogue of the Prior Art
Compound of WO 2009/0022013, Example 45 (72 nmol/animal) to pigs

| Animal No. | Dose pmol/kg | $T_{max}$ Min | $C_{max}$/D pM/ (nmol/kg) | AUC/D pM*min/ (pmol/kg) | % extrap % | $T_{1/2}$ min | MRT min |
|---|---|---|---|---|---|---|---|
| 10107 | 713 | 50 | 450 | 128 | 6 | 182 | 310 |
| 10109 | 1714 | 20 | 241 | 40 | 9 | 148 | 226 |
| 10110 | 720 | 10 | 513 | 104 | 7 | 153 | 261 |
| 10111 | 706 | 50 | 363 | 81 | 8 | 158 | 255 |

TABLE 12-continued

Pharmacokinetic parameters after sc. dosing of 1 nmol/kg of the C14 diacid analogue of the C16 diacid analogue of the Prior Art Compound of WO 2009/0022013, Example 45 (72 nmol/animal) to pigs

| Animal No. | Dose pmol/ kg | $T_{max}$ Min | $C_{max}$/D pM/ (nmol/kg) | AUC/D pM*min/ (pmol/kg) | % extrap % | $T_{1/2}$ min | MRT min |
|---|---|---|---|---|---|---|---|
| 10112 | 1735 | 20 | 344 | 41 | 10 | 219 | 305 |
| N | | 5 | 5 | 5 | 5 | 5 | 5 |
| Mean | | | 382 | 79 | 8 | | 271 |
| SD | | 19 | 104 | 39 | 1 | | 35 |

It is concluded that the C14 diacid version of the insulin derivative of the prior art, WO 2009/022013, Example 45, in a formulation without zinc is associated with a protracted tailing, possibly originating from a delayed absorption of a part of the subcutaneous depot. The plasma concentration of this insulin at the 10 hour (600 minutes) time point is 24 µM. The mean retention time (MRT) of this C14 diacid analogue of the prior art was found to be 271 minutes.

The corresponding results obtained with the C14 diacid analogues of Examples 1 and 2 of the present invention were 165 and 111 minutes, respectively. Further, the blood glucose lowering effect is extended to last for at least 11 hours (660 minutes).

This makes this insulin of the prior art inappropriate for prandial use.

Example 61

Subcutaneous PK/PD Profiles of Insulin Analogues of the Invention and the Prior Art in Sprague Dawley Rats The insulin derivatives of the invention may be tested by subcutaneous administration to rats, e.g. comparing with insulin aspart (NovoRapid) in the commercial formulation or comparing with similar B29K acylated insulin analogues of the prior art according to this protocol. The derivatives may be tested for pharmacokinetic and/or pharmacodynamic parameters.

The insulin derivatives of the prior art are only stable in formulation in presence of zinc ions, whereas the insulin derivatives of the present invention are stable in formulation without added zinc. In order to compare the profiles of the insulin derivatives of the invention to the profiles of the analogues of the prior art, the analogues of the invention are tested in this protocol using zinc-free formulations, and the analogues of the prior art are tested using 3 zinc ions per hexamer. This is to obtain the fastest PK profiles obtainable in clinically useful (i.e. chemically and physically stable) formulations.

In Vivo Protocol

Male Sprague-Dawley rats, 400 grams, are used for these experiments. The rats are not fasted prior to testing. During the three hours study period, the rats have free access to water but not to food. Blood samples are drawn (sublingual vein; 200 µl into Microvette®200 EDTA tubes) and plasma collected from non-anesthetized animals at the time points 0 (before dosing) and 3, 7, 15, 30, 60, 120 and 180 minutes after dosing of the insulin derivative. The rats are dosed subcutaneously (25 nmol/kg; 600 µM formulation of insulin derivative) in the neck using a NovoPen Echo® mounted with a Softfine® 12 mm needle. Plasma concentrations of glucose and insulin derivatives are quantified using a BIO-SEN analyser and immuno assays/LCMS analysis, respectively.

Figure 2A:
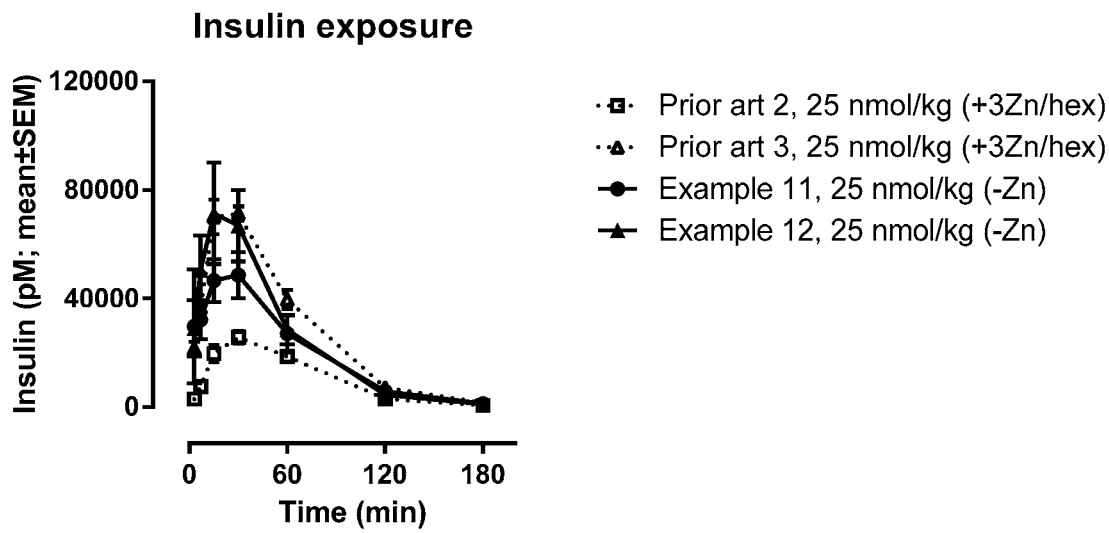
FIGS. 2A and 2B show PK profiles of C14 based analogues of the invention (Examples 11 and 12, and Examples 4 and 10, respectively), and of C14 based analogues of the prior art (Prior Art Analogues 2 and 3, and Prior Art Analogues 2 and 3), respectively, following subcutaneous injection to Sprague Dawley rats.
Figure 2B:
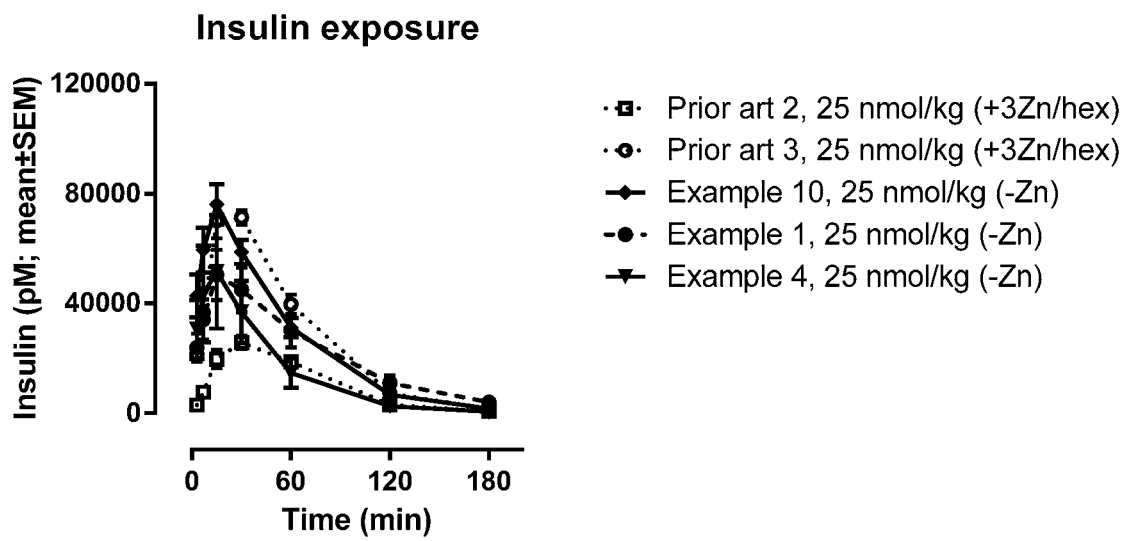
Figure 2C:
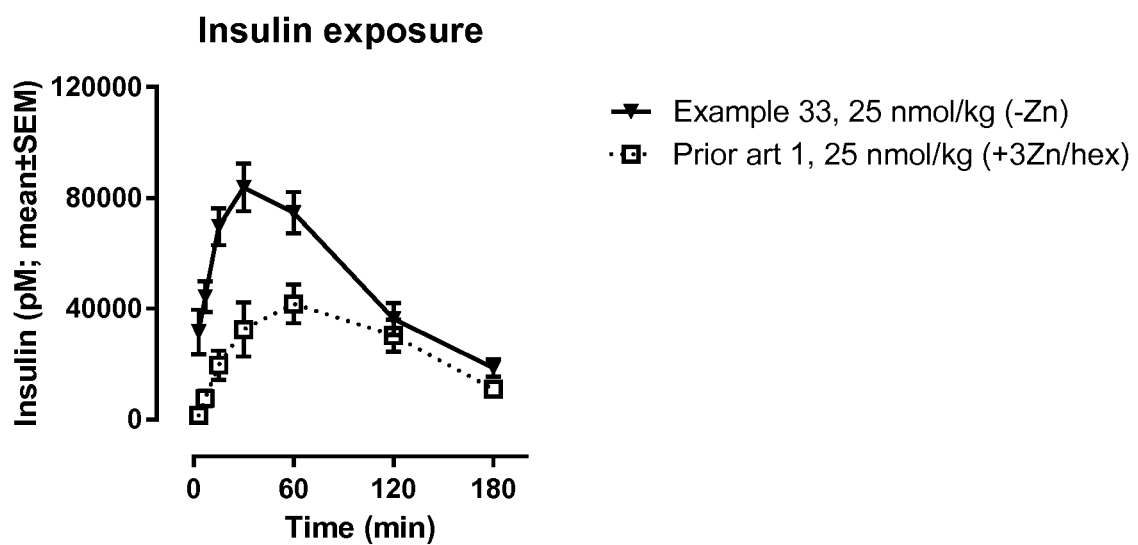
FIG. 2C shows PK profiles of C16 based analogues of the invention (Example 33), and of C16 based analogues of the prior art (Prior Art Analogue 1), following subcutaneous injection to Sprague Dawley rats.

Results from testing analogues of the invention and of the prior art are given in Tables 5 and 6 and in the following figures:

FIGS. 2A and 2B shows PK profiles of C14 based analogues of the invention (Examples 11 and 12, and Examples 4 and 10, respectively), and of C14 based analogues of the prior art (Prior Art Analogue 2 and 3 and Prior Art Analogue 2 and 3), respectively, following subcutaneous injection to Sprague Dawley rats;

FIG. 2C shows PK profiles of C16 based analogues of the invention (Example 33), and of C16 based analogues of the prior art (Prior Art Analogue 1), following subcutaneous injection to Sprague Dawley rats; FIGS. 2D1 and 2D2 shows PD profiles (resulting from PK profiles shown in FIG. 2A) of C14 diacid based analogues of the invention and of C14 diacid based analogues of the prior art following subcutaneous injection to Sprague Dawley rats; and FIGS. 2E1 and 2E2 shows PD profiles (resulting from PK profiles shown in FIG. 2B) of C14 diacid based analogues of the invention and of C14 diacid based analogues of the prior art following subcutaneous injection to Sprague Dawley rats; and FIGS. 2F1 and 2F2 shows PD profiles (resulting from PK profiles shown in FIG. 2C) of C16 diacid based analogues of the invention and of C16 diacid based analogues of the prior art following subcutaneous injection to Sprague Dawley rats.

TABLE 5

Selected PK parameters of C14 diacid acylated insulins of the invention and of similar insulins of the prior art following subcutaneous injection to Sprague Dawley rats SD values are given in parentheses

| Ex. No. | Zn in formu-lation* | HSA bind-er | $T_{max}$ (min) | $C_{max}$ (pmol) | AUC15/ AUC60** | MRT (min) | $T_{1/2}$ (min) |
|---|---|---|---|---|---|---|---|
| 4 | −Zn | C14 | 15 | 51520 (20731) | 0.29 (0.04) | 40 (5) | 24 (1.7) |
| 10 | −Zn | C14 | 15 | 76040 (16591) | 0.30 (0.03) | 48 (5) | 28 (2) |
| 11 | −Zn | C14 | 15 | 52920 (10997) | 0.21 (0.03) | 52 (4.3) | 28 (1.2) |
| 12 | −Zn | C14 | 15 | 74520 (17091) | 0.22 (0.04) | 44 (2.4) | 25 (1) |
| PA 2 | +3Zn/hex | C14 | 30 | 25720 (5323) | 0.12 (0.03) | 56 (6) | 24 (1) |
| PA 3 | +3Zn/hex | C14 | 30 | 66246 (20521) | 0.18 (0.01) | 50 (4) | 26 (1) |

<sup>a</sup>PA refers to Prior Art Compound
*−Zn means no added zinc ions; +3Zn/hex means 3 added zinc ions per hehamer (6 insulin molecules)
**AUC15/AUC60 is the area under the curve (plasma exposure vs. time) for the first 15 minutes divided by the area under the curve for the first 60 minutes It is concluded that the C14 diacid acylated analogues of the invention (in formulations without zinc) are absorbed more rapidly than the analogues of the prior art (in formulations with 3 zinc ions per hexamer) as seen for the $T_{max}$ data. $T_{max}$ of the prior art analogues are about 30 minutes whereas the insulins of the invention have $T_{max}$ around 15 minutes. The ratio AUC15/AUC60 is a measure of the fraction absorbed during the first 15 minutes in relation to the fraction absorbed after 1 hour. Thus the higher the ratio the more insulin is absorbed during the first 15 minutes. It is seen that the insulins of the invention are associated with a higher ratio than similar analogues of the prior art and are thus more rapidly absorbed.

Consequently, the analogues of the invention are better suited for prandial administration than insulins of the prior art.

TABLE 6

Selected PK parameters of C16 diacid acylated insulins of the invention and of similar insulins of the prior art following subcutaneous injection to Sprague Dawley rats SD values are given in parentheses

| Ex. No.[a] | Zn in formu-lation* | HSA bind-er | $T_{max}$ (min) | $C_{max}$ (pmol) | AUC15/ AUC60** | MRT (min) | T½ (min) |
|---|---|---|---|---|---|---|---|
| 33 | −Zn | C16 | 30 | 83680 (19101) | 0.16 (0.01) | 101 (13) | 58 (9) |
| 31 | −Zn | C16 | 30 | 75680 (15869) | 0.16 (0.13) | 128 (13) | 79 (7.8) |
| 41 | −Zn | C16 | 30 | 86280 (18241) | 0.18 (0.03) | 97 (15) | 57 (8) |
| 42 | −Zn | C16 | 15 | 75080 (12292) | 0.20 (0.01) | 73 (12) | 41 (10) |
| PA 1 | +3Zn/hex | C16 | 60 | 41760 (7019) | 0.08 (0.01) | 108 (22) | 41 (18) |

[a]PA refers to Prior Art Compound
*−Zn means no added zinc ions; +3Zn/hex means 3 added zinc ions per hehamer (6 insulin molecules)
**AUC15/AUC60 is the area under the curve (plasma exposure vs. time) for the first 15 minutes divided by the area under the curve for the first 60 minutes It is concluded that the C16 diacid acylated analogues of the invention (in formulations without zinc) are absorbed more rapidly than the the analogues of the prior art (in formulations with 3 zinc ions per hexamer) as seen for the $T_{max}$ data. $T_{max}$ of the prior art analogue is about 60 minutes whereas the insulins of the invention have $T_{max}$ around 30 minutes. The ratio AUC15/AUC60 is a measure of the fraction absorbed during the first 15 minutes in relation to the fraction absorbed after 1 hour. Thus the higher the ratio the more insulin is absorbed during the first 15 minutes. It is seen that the insulins of the invention are associated with a higher ratio than similar analogues of the prior art and are thus more rapidly absorbed.

Consequently, the C16 diacid analogues of the invention are better suited for prandial administration than the C16 diacid insulins of the prior art.

The invention claimed is:

1. An acylated analogue of human insulin, selected from the group consisting of:

A22K(N(eps)tetradecanedioyl-gGlu-2×OEG), B3E, B27E, B28E, B29R, desB30 human insulin;

A14E, A22K(N(eps)tetradecanedioyl-gGlu-2×OEG), B3E, B27E, B28E, B29R, desB30 human insulin;

A22K(N(eps)tetradecanedioyl-4×gGlu), B3E, B27E, B28E, B29R, desB30 human insulin;

A14E, A22K(N(eps)tetradecanedioyl-4×gGlu), B3E, B27E, B28E, B29R, desB30 human insulin;

A22K(N(eps)tetradecanedioyl-gGlu-2×OEG), B3E, B27P, B28E, B29R, desB30 human insulin;

A22K(N(eps)tetradecanedioyl-4×gGlu), B3E, B27E, B29R, desB30 human insulin;

A22K(N(eps)tetradecanedioyl-gGlu-2×OEG), B3E, B28D, B29R, desB30 human insulin;

A14E, A22K(N(eps)tetradecanedioyl-4×gGlu), B3Q, B28D, B29R, desB30 human insulin;

A14E, A22K(N(eps)tetradecanedioyl-4×gGlu), B3Q, B27E, B28E, B29R, desB30 human insulin;

A22K(N(eps)tetradecanedioyl-4×gGlu), B3E, B28D, B29R, desB30 human insulin;

A22K(N(eps)tetradecanedioyl-4×gGlu), B3E, B26E, B28E, B29R, desB30 human insulin;

A22K(N(eps)tetradecanedioyl-4×gGlu), B3E, B26E, B29R, desB30 human insulin;

A22K(N(eps)tetradecanedioyl-4×gGlu), B3E, B26E, B27P, B28R, desB29, desB30 human insulin;

A22K(N(eps)tetradecanedioyl-4×gGlu), B3E, B27E, B28R, desB29, desB30 human insulin;

A8R, A22K(N(eps)tetradecanedioyl-4×gGlu), B3E, B26E, B29R, desB30 human insulin;

A8R, A22K(N(eps)tetradecanedioyl-4×gGlu), B3E, B26E, B27P, B28R, desB29, desB30 human insulin;

A8R, A22K(N(eps)tetradecanedioyl-4×gGlu), B3E, B27E, B28R, desB29, desB30 human insulin;

A22K(N(eps)tetradecanedioyl-4×gGlu), B3E, B26E, B27E, B28R, desB29, desB30 human insulin;

A8R, A22K(N(eps)tetradecanedioyl-4×gGlu), B3E, B26E, B27E, B28R, desB29, desB30 human insulin;

A22K(N(eps)tetradecanedioyl-4×gGlu), B3E, B28E, B29P, B30R human insulin;

A22K(N(eps)tetradecanedioyl-4×gGlu), B3E, B26E, B28E, B29P, B30R human insulin;

A22K(N(eps)tetradecanedioyl-4×gGlu), B3E, B27E, B28E, B29P, B30R human insulin;

A8R, A22K(N(eps)tetradecanedioyl-4×gGlu), B3E, B26E, B28E, B29R, desB30 human insulin;

A8R, A22K(N(eps)tetradecanedioyl-4×gGlu), B3E, B27E, B28E, B29R, desB30 human insulin;

A22K(N(eps)Hexadecanedioyl-gGlu-2×OEG), B3E, B27E, B29R, desB30 human insulin;

A14E, A22K(N(eps)hexadecanedioyl-gGlu-2×OEG), B3E, B27E, B28E, B29R, desB30 human insulin;

A14E, A22K(N(eps)hexadecanedioyl-4×gGlu), B3E, B27E, B28E, B29R, desB30 human insulin;

A22K(N(eps)hexadecanedioyl-4×gGlu), B3E, B27E, B28E, B29R, desB30 human insulin;

A22K(N(eps)hexadecanedioyl-gGlu-2×OEG), B3E, B27P, B28E, B29R, desB30 human insulin;

A22K(N(eps)hexadecanedioyl-4×gGlu), B3E, B27P, B28E, B29R, desB30 human insulin;

A22K(N(eps)hexadecanedioyl-gGlu-2×OEG), B3E, B27E, B28E, B29R, desB30 human insulin;

A22K(N(eps)hexadecanedioyl-4×gGlu), B3E, B27E, B29R, desB30 human insulin;

A22K(N(eps)hexadecanedioyl-gGlu-2×OEG), B3E, B28D, B29R, desB30 human insulin;

A22K(N(eps)tetradecanedioyl-4×gGlu), B3E, B26E, B28D, B29R, desB30 human insulin;

A22K(N(eps)tetradecanedioyl-4×gGlu), B3E, B26E, B27E, B29P, B30R human insulin;

A22K(N(eps)tetradecanedioyl-4×gGlu), B3E, B26E, B27E, B28E, B29R, desB30 human insulin;

A22K(N(eps)hexadecanedioyl-4×gGlu), B3E, B28D, B29R, desB30 human insulin;

A22K(N(eps)tetradecanedioyl-4×gGlu), B3E, B27P, B28E, B29R, desB30 human insulin;

A22K(N(eps)tetradecanedioyl-4×gGlu), B3Q, B26E, B29R, desB30 human insulin;

A22K(N(eps)tetradecanedioyl-4×gGlu), B3Q, B26E, B28E, B29R, desB30 human insulin;

A22K(N(eps)hexadecanedioyl-4×gGlu), B3E, B26E, B29R, desB30 human insulin;

A22K(N(eps)hexadecanedioyl-gGlu-2×OEG), B3E, B26E, B29R, desB30 human insulin;

A22K(N(eps)hexadecanedioyl-gGlu-4×OEG), B3E, B26E, B29R, desB30 human insulin;

A22K(N(eps)hexadecanedioyl-gGlu-6×OEG), B3E, B26E, B29R, desB30 human insulin;

A22K(N(eps)hexadecanedioyl-4×gGlu-2×OEG), B3E, B26E, B29R, desB30 human insulin; and A22K(N(eps)hexadecanedioyl-4xgGlu), B3Q, B26E, B29R, desB30 human insulin, wherein the analogue is prone to dissociation into monomers following subcutaneous injection.

2. A pharmaceutical composition comprising an insulin analogue according to claim 1, and one or more pharmaceutically acceptable carriers or diluents.

3. The pharmaceutical composition according to claim 2, formulated as a low-zinc composition, with no added zinc ions.

4. The pharmaceutical composition according claim 3, formulated as a low-zinc composition, comprising less than 0.2 $Zn^{2+}$ ions per 6 insulin molecules.

5. The low-zinc pharmaceutical composition according to claim 3, wherein no surfactant has been added.

6. The low-zinc pharmaceutical composition according to claim 3, comprising a nicotinic compound.

7. A method of treating diabetes and/or hypoglycaemia comprising administering to a subject in need thereof a pharmaceutical composition comprising a therapeutically effective amount of the acylated insulin analogue according to claim 1.

8. The low-zinc pharmaceutical composition according to claim 6, wherein the nicotinic compound is nicotinamide.

* * * * *